(12) United States Patent
Challenger et al.

(10) Patent No.: US 6,849,649 B2
(45) Date of Patent: Feb. 1, 2005

(54) N-PHENPROPYLCYCLOPENTYL-SUBSTITUTED GLUTARAMIDE DERIVATIVES AS INHIBITORS OF NEUTRAL ENDOPEPTIDASE

(75) Inventors: Stephen Challenger, Sandwich (GB); Andrew Simon Cook, Sandwich (GB); Adam Thomas Gillmore, Sandwich (GB); Donald Stuart Middleton, Sandwich (GB); David Cameron Pryde, Sandwich (GB); Alan Stobie, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/696,021

(22) Filed: Oct. 28, 2003

(65) Prior Publication Data

US 2004/0106611 A1 Jun. 3, 2004

Related U.S. Application Data

(62) Division of application No. 10/096,218, filed on Mar. 12, 2002, now Pat. No. 6,660,756.
(60) Provisional application No. 60/317,777, filed on Sep. 6, 2001, provisional application No. 60/299,031, filed on Jun. 18, 2001, and provisional application No. 60/292,495, filed on May 21, 2001.

(30) Foreign Application Priority Data

| Mar. 28, 2001 | (GB) | ............................................. 0107750 |
| May 30, 2001 | (GB) | ............................................. 0113112 |
| Aug. 17, 2001 | (GB) | ............................................. 0120152 |

(51) Int. Cl.[7] ...................... A61K 31/44; A61K 31/415; A61K 31/335; A01N 43/56; A01N 43/32

(52) U.S. Cl. ...................... 514/357; 514/406; 514/452; 514/465; 514/469; 514/530; 514/563; 546/334; 546/335; 546/336; 548/556.5; 549/366; 549/406; 549/441; 549/467; 560/39; 560/41; 562/444; 562/450

(58) Field of Search ...................... 560/39, 41; 562/444, 562/450; 514/357, 406, 452, 465, 469, 530, 563; 546/334–336; 548/556.5; 549/366, 406, 441, 467

(56) References Cited

FOREIGN PATENT DOCUMENTS

| EP | 0274234 | 11/1991 | |
| EP | 0 644 176 A1 * | 3/1995 | ......... C07C/69/757 |
| EP | 1097719 | 9/2001 | |
| WO | WO 9107386 | 5/1991 | |
| WO | WO 9110644 | 7/1991 | |
| WO | WO 9406756 | 3/1994 | |
| WO | WO 9113054 | 9/2001 | |
| WO | WO 0202513 | 1/2002 | |

OTHER PUBLICATIONS

Challenger, S., Stereoselective Synthesis of a Candoxatril Intermediate via Asymmetric Hydrogenation. Tetrahedron Letters (1999), 40 (11), p. 2187–2190.*

* cited by examiner

*Primary Examiner*—Brian J. Davis
(74) *Attorney, Agent, or Firm*—Peter C. Richardson; Gregg C. Benson; Martha G. Munchhof

(57) ABSTRACT

The invention relates to compounds of formula (I) for treating for example sexual dysfunction, wherein $R^1$ is optionally substituted $C_{1-6}$alkyl, optionally substituted carbocyclyl, optionally substituted heterocyclyl, hydrogen, $C_{1-6}$alkoxy, $-NR^2R^3$ or $-NR^4SO_2R^5$; X is the linkage $-(CH_2)_n-$ or $-(CH_2)_q-O-$ (wherein Y is attached to the oxygen); wherein one or more hydrogen atoms in linkage X may be replaced independently by $C_{1-4}$alkoxy; hydroxy; hydroxy($C_{1-3}$alkyl); $C_{3-7}$cycloalkyl; carbocyclyl; heterocyclyl; or by $C_{1-4}$alkyl optionally substituted by one or more fluoro or phenyl groups; n is 3, 4, 5, 6 or 7; and q is 2, 3, 4, 5 or 6; and Y is phenyl or pyridyl, each of which may be substituted; or two $R^8$ groups on adjacent carbon atoms together with the interconnecting carbon atoms may form a fused optionally substituted 5- or 6-membered carbocyclic or heterocyclyic ring.

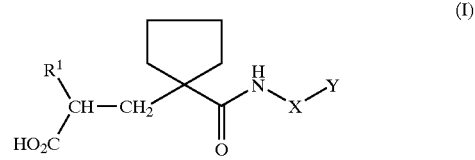

(I)

3 Claims, 1 Drawing Sheet

NEP inhibitors increase Intracavernosal Pressure (ICP)

N-PHENPROPYLCYCLOPENTYL-SUBSTITUTED GLUTARAMIDE DERIVATIVES AS INHIBITORS OF NEUTRAL ENDOPEPTIDASE

This application is a divisional of U.S. application Ser. No. 10/096,218 filed on Mar. 12, 2002, now U.S. Pat. No. 6,660,756, which claims priority from Great Britain Application No. 0107750.2 filed on Mar. 28, 2001, Great Britain Application No. 0113112.7 filed on May 30, 2001, Great Britain Application No. 0120152.4 filed on Aug. 17, 2001, U.S. provisional application Ser. No. 60/292,495, filed on May 21, 2001, U.S. provisional application Ser. No. 60/299,031 filed on Jun. 18, 2001 and U.S. provisional application Ser. No. 60/317,777 filed Sep. 6, 2001.

The invention relates to inhibitors of neutral endopeptidase enzyme (NEP), uses thereof, processes for the preparation thereof, intermediates used in the preparation thereof and compositions containing said inhibitors. These inhibitors have utility in a variety of therapeutic areas including the treatment of male and female sexual dysfunction, particularly female sexual dysfunction (FSD), especially wherein the FSD is female sexual arousal disorder (FSAD).

NEP inhibitors are disclosed in WO 91/07386 and WO 91/10644.

The use of NEP inhibitors for treating FSD is disclosed in EP1 097 719-A1.

SUMMARY OF INVENTION

According to a first aspect, the invention provides a compound of formula (I), a pharmaceutically acceptable salt, solvate, polymorph or prodrug thereof;

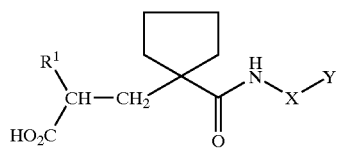

(I)

wherein $R^1$ is $C_{1-6}$alkyl which may be substituted by one or more substituents, which may be the same or different, selected from the list: halo, hydroxy, $C_{1-6}$alkoxy, hydroxy$C_{1-6}$alkoxy, $C_{1-6}$alkoxy$C_{1-6}$alkoxy, carbocyclyl (preferably $C_{3-7}$cycloalkyl, $C_{3-7}$cycloalkenyl or phenyl), carbocyclyloxy (preferably phenoxy), $C_{1-4}$alkoxycarbocyclyloxy (preferably $C_{1-4}$alkoxyphenoxy), heterocyclyl, heterocyclyloxy, —$NR^2R^3$, —$NR^4COR^5$, —$NR^4SO_2R^5$, —$CONR^2R^3$, —$S(O)_pR^6$, —$COR^7$ and —$CO_2(C_{1-4}$alkyl); or $R^1$ is carbocyclyl (preferably $C_{3-7}$cycloalkyl or phenyl) or heterocyclyl, each of which may be substituted by one or more substituents from said list, which substituents may be the same or different, which list further includes $C_{1-6}$alkyl; or $R^1$ is hydrogen, $C_{1-6}$alkoxy, —$NR^2R^3$ or —$NR^4SO_2R^5$;

wherein $R^2$ and $R^3$, which may be the same or different, are carbocyclyl (preferably $C_{3-7}$cycloalkyl or phenyl) or heterocyclyl (each of which may be substituted by $C_{1-4}$alkyl, hydroxy or $C_{1-4}$alkoxy); or are hydrogen or $C_{1-4}$alkyl; or $R^2$ and $R^3$ together with the nitrogen to which they are attached form a pyrrolidinyl, piperidino, morpholino, piperazinyl or N—($C_{1-4}$alkyl)piperazinyl group;

$R^4$ is hydrogen or $C_{1-4}$alkyl;

$R^5$ is $C_{1-4}$alkyl, $CF_3$, carbocyclyl (preferably phenyl), $C_{1-4}$alkylcarbocyclyl (preferably $C_{1-4}$ alkylphenyl), $C_{1-4}$alkoxycarbocyclyl (preferably $C_{1-4}$alkoxyphenyl), heterocyclyl, $C_{1-4}$alkoxy or —$NR^2R^3$;

$R^6$ is $C_{1-4}$alkyl, carbocyclyl (preferably phenyl), heterocyclyl or $NR^2R^3$; and $R^7$ is $C_{1-4}$alkyl, carbocyclyl (preferably $C_{3-7}$cycloalkyl or phenyl) or heterocyclyl;

p is 0, 1, 2 or 3;

X is the linkage —$(CH_2)_n$— or —$(CH_2)_q$—O— (wherein Y is attached to the oxygen); wherein one or more hydrogen atoms in linkage X may be replaced independently by $C_{1-4}$alkoxy; hydroxy; hydroxy$C_{1-3}$alkyl; $C_{3-7}$cycloalkyl; carbocyclyl; heterocyclyl; or by $C_{1-4}$alkyl optionally substituted by one or more fluoro or phenyl groups; n is 3, 4, 5, 6 or 7; and q is 2, 3, 4, 5 or 6; and Y is phenyl or pyridyl, each of which may be substituted by one or more groups $R^8$ which may be the same or different, wherein $R^8$ is hydroxy; mercapto; halogen; cyano; acyl; amino; mono($C_{1-4}$alkyl)amino; di($C_{1-4}$alkyl)amino; carbocyclyl or heterocyclyl (either of which is optionally substituted by $C_{1-6}$alkyl, halo$C_{1-6}$alkyl, $C_{1-6}$alkoxy, halo$C_{1-6}$alkoxy, $C_{1-6}$alkylthio or halogen); $C_{1-6}$alkoxy; phenoxy; $C_{1-6}$alkylthio; phenylthio; or alkyl optionally substituted by $C_{1-6}$alkoxy, halo$C_{1-6}$alkoxy, $C_{1-6}$alkylthio, halogen or phenyl; or two $R^8$ groups on adjacent carbon atoms together with the interconnecting carbon atoms may form a fused 5- or 6-membered carbocyclic or heterocyclyic ring, optionally substituted by $C_{1-6}$alkyl, halo$C_{1-6}$alkyl, $C_{1-6}$alkoxy, halo$C_{1-6}$alkoxy, $C_{1-6}$alkylthio or halogen.

Preferably $R^1$ is hydrogen, $C_{1-6}$alkyl, $C_{1-6}$alkoxy, $C_{1-6}$alkoxy$C_{1-3}$alkyl, $C_{1-6}$alkoxy$C_{1-6}$alkoxy$C_{1-3}$alkyl or $C_{1-6}$alkyl substituted by phenyl.

More preferably $R^1$ is hydrogen, $C_{1-6}$alkyl, $C_{1-6}$alkoxy, $C_{1-6}$alkoxy$C_{1-3}$alkyl (preferably methoxy$C_{1-3}$alkyl) or $C_{1-6}$alkoxy$C_{1-6}$alkoxy$C_{1-3}$alkyl (preferably methoxyethoxymethyl).

More preferably still $R^1$ is $C_{1-4}$alkyl (preferably propyl) or $C_{1-6}$alkoxy$C_{1-3}$alkyl (preferably methoxy$C_{1-3}$alkyl, more preferably methoxyethyl).

A preferred group of compounds are of formula Ia:

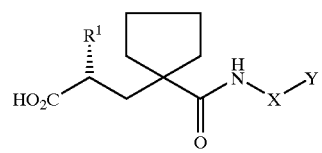

(Ia)

Preferably n is 3 or 4, more preferably 3.
Preferably q is 2 or 3, more preferably 2.
Preferably X is —$(CH_2)_n$— wherein one or more hydrogen atoms in linkage X may be replaced by one or more of the groups defined for X in the first aspect.

Preferably $R^8$ is $C_{1-6}$alkyl, $C_{1-6}$alkoxy, hydroxy, mercapto, halo, cyano, carbocyclyl or heterocyclyl; or two $R^8$ groups on adjacent carbon atoms together with the interconnecting carbon atoms may form a fused 5- or 6-membered carbocyclic or heterocyclyic ring, optionally substituted by $C_{1-6}$alkyl, halo$C_{1-6}$alkyl, $C_{1-6}$alkoxy, halo$C_{1-6}$alkoxy, $C_{1-6}$alkylthio or halogen.

When $R^8$ is carbocyclyl, preferred groups are cyclopentyl, cyclopropyl, cyclohexyl or phenyl.

When $R^8$ is heterocyclyl, preferred groups are pyridyl, oxadiazolyl, pyrazolyl or triazolyl.

When Y is phenyl and two $R^8$ groups on adjacent carbon atoms together with the interconnecting carbon atoms form a fused 5- or 6-membered carbocyclic or heterocyclyic ring, preferred fused ring systems are naphthyl, quinolinyl, isoquinolinyl, indolyl, indazolyl, benzimidazolyl, benzisoxazolyl, dihydrobenzofuranyl, benzoxazolyl, indanyl, benzisothiazolyl and benzothiazolyl.

Preferred compounds of the invention are:
(2R)-2-{[1-({[3-(4-methoxyphenyl)propyl]amino}carbonyl)cyclopentyl]methyl}pentanoic acid (Example 16),
3-{[1-({[3-(4-methoxyphenyl)propyl]amino}carbonyl)cyclopentyl]propanoic acid (Example 18),
3-{[1-({[3-(2,3-dihydro-1-benzofuran-5-yl)propyl]amino}carbonyl)cyclopentyl]propanoic acid (Example 21),
2-{[1-({[3-(4-chlorophenyl)propyl]amino}carbonyl)cyclopentyl]methyl}-4-methoxybutanoic acid (Example 15),
2-{[1-({[3-(4-fluorophenyl)propyl]amino}carbonyl)cyclopentyl]methyl}-4-methoxybutanoic acid (Example 4),
4-methoxy-2-{[1-({[3-(4-methoxyphenyl)propyl]amino}carbonyl)cyclopentyl]-methyl}butanoic acid (Example 1),
2-{[1-({[3-(2,3-dihydro-1-benzofuran-5-yl)propyl]amino}carbonyl)cyclopentyl]-methyl}-4-methoxybutanoic acid (Example 11),
(2S)-2-{[1-({[3-(4-chlorophenyl)propyl]amino}carbonyl)cyclopentyl]methyl}-4-methoxybutanoic acid (Example 22), and
(2S)-2-{[1-({[3-(2,3-dihydro-1-benzofuran-5-yl)propyl]amino}carbonyl)cyclopentyl]-methyl}-4-methoxybutanoic acid (Example 25).

A particularly preferred compound is (2S)-2-{[1-({[3-(4-chlorophenyl)propyl]amino}carbonyl)cyclopentyl]methyl}-4-methoxybutanoic acid (Example 22).

Unless otherwise indicated, any alkyl group may be straight or branched and is of 1 to 6 carbon atoms, preferably 1 to 4 and particularly 1 to 3 carbon atoms.

Unless otherwise indicated, any carbocyclyl group contains 3 to 8 ring-atoms, and may be saturated, unsaturated or aromatic. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Unless otherwise indicated, any heterocyclyl group contains 5 to 7 ring-atoms up to 4 of which may be hetero-atoms such as nitrogen, oxygen and sulfur, and may be saturated, unsaturated or aromatic. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Halo means fluoro, chloro, bromo or iodo.

For the avoidance of doubt, unless otherwise indicated, the term substituted means substituted by one or more defined groups. In the case where groups may be selected from a number of alternatives groups, the selected groups may be the same or different.

For the avoidance of doubt, the term independently means that where more than one substituent is selected from a number of possible substituents, those substituents may be the same or different.

The pharmaceutically or veterinarily acceptable salts of the compounds of formula I which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc, diolamine, olamine, ethylenediamine, tromethamine, chloine, megulamine and diethanolamine salts. For reviews on suitable pharmaceutical salts see Berge et al, J. Pharm, Sci., 66, 1–19, 1977; P L Gould, International Journal of Pharmaceutics, 33 (1986), 201–217; and Bighley et al, Encyclopedia of Pharmaceutical Technology, Marcel Dekker Inc, New York 1996, Volume 13, page 453–497.

Hereinafter, the compounds, their pharmaceutically acceptable salts, their solvates and polymorphs, defined in any aspect of the invention or preferred embodiment (except intermediate compounds in chemical processes) are referred to as "compounds of the invention".

The pharmaceutically acceptable solvates of the compounds of the invention include hydrates thereof.

The compounds of the invention and intermediates may possess one or more chiral centres and so exist in a number of stereoisomeric forms. All stereoisomers and mixtures thereof are included in the scope of the present invention.

Individual enantiomers may be obtained by a variety of techniques known to the skilled chemist, such as by high pressure liquid chromatography (HPLC) of the corresponding racemate using a suitable chiral support or by fractional crystallisation of the diastereoisomeric salts formed by reaction of the corresponding racemate with a suitable optically active base, as appropriate. A preferred optically active base is pseudoephedrine (see Preparation 69).

Separation of diastereoisomers may be achieved by conventional techniques, e.g. by fractional crystallisation, chromatography or H.P.L.C.

The compounds of the invention may exist in one or more tautomeric forms. All tautomers and mixtures thereof are included within the scope of the present invention. For example, a claim to 2-hydroxypyridinyl would also cover its tautomeric form, α-pyridonyl.

It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention.

All protected derivatives and prodrugs of compounds of the invention are included within the scope of the invention. Examples of suitable pro-drugs for the compounds of the present invention are described in Drugs of Today, Volume 19, Number 9, 1983, pp 499–538 and in Topics in Chemistry, Chapter 31, pp 306–316 and in "Design of Prodrugs" by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds of the invention.

Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Drug metabolism studies have shown that in vivo, compounds of formula I may form the following compounds, which compounds also are inhibitors of NEP

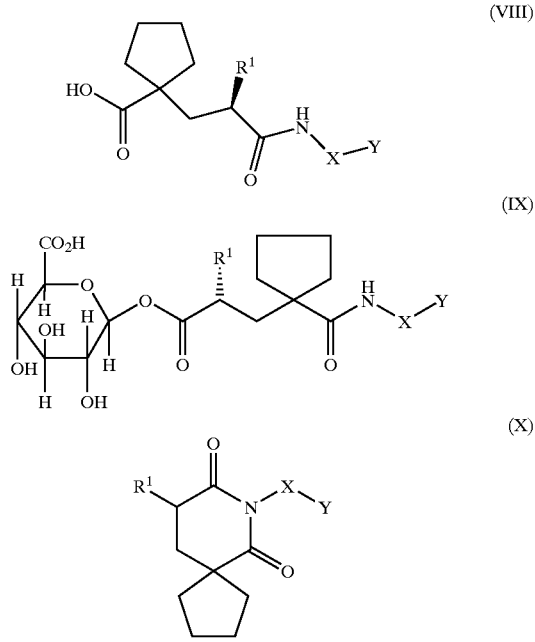

These metabolites are formed in particular when $R^1$ is methoxyethyl and —XY is 3-(4-chlorophenyl)propyl.

The invention also includes all suitable isotopic variations of the compounds of the invention. An isotopic variation is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^3H$ or $^{14}C$ is incorporated, are useful in drug and/or substrate tissue distribution studies. Tritiated, i.e. $^3H$, and carbon-14, i.e. $^{14}C$ isotopes are particularly preferred for their ease of preparation and detectability. Further, substitution with isotopes such as deuterium, i.e. $^2H$, may afford certain therapeutic advantages resulting from greater metabolic stability, for example, increased in vivo half-life and reduced dosage requirements and hence may be preferred in some circumstances. Isotopic variations of the compounds of the invention can generally be prepared by conventional procedures such as by the methods or preparations described in the Examples and Preparations hereafter using appropriate isotopic variations of suitable reagents.

The compounds of the invention are inhibitors of the zinc-dependent, neutral endopeptidase EC.3.4.24.11., and it is proposed that the compounds of the invention will treat the disease states listed below. This enzyme is involved in the breakdown of several bioactive oligopeptides, cleaving peptide bonds on the amino side of hydrophobic amino acid residues. The peptides metabolised include atrial natriuretic peptides (ANP), bombesin, bradykinin, calcitonin gene-related peptide, endothelins, enkephalins, neurotensin, substance P and vasoactive intestinal peptide. Some of these peptides have potent vasodilatory and neurohormone functions, diuretic and natriuretic activity or mediate behaviour effects.

Thus, the compounds of the invention, by inhibiting the neutral endopeptidase EC.3.4.24.11, can potentiate the biological effects of bioactive peptides. Thus, in particular the compounds have utility in the treatment of a number of disorders, including hypertension, pulmonary hypertension, peripheral vascular disease, heart failure, angina, renal insufficiency, acute renal failure, cyclical oedema, Menières disease, hyperaldosteroneism (primary and secondary) and hypercalciuria. In addition, because of their ability to potentiate the effects of ANF the compounds have utility in the treatment of glaucoma. As a further result of their ability to inhibit the neutral endopeptidase E.C.3.4.24.11 the compounds of the invention may have activity in other therapeutic areas including for example the treatment of menstrual disorders, preterm labour, pre-eclampsia, endometriosis, and reproductive disorders (especially male and female infertility, polycystic ovarian syndrome, implantation failure). Also the compounds of the invention should treat asthma, inflammation, leukemia, pain, epilepsy, affective disorders, dementia and geriatric confusion, obesity and gastrointestinal disorders (especially diarrhoea and irritable bowel syndrome), wound healing (especially diabetic and venous ulcers and pressure sores), septic shock, the modulation of gastric acid secretion, the treatment of hyperreninaemia, cystic fibrosis, restenosis, diabetic complications and athereosclerosis. In a preferred embodiment the compounds of the invention are useful in the treatment of male and female sexual dysfunction.

DETAILED DESCRIPTION OF THE INVENTION

Figure 1:
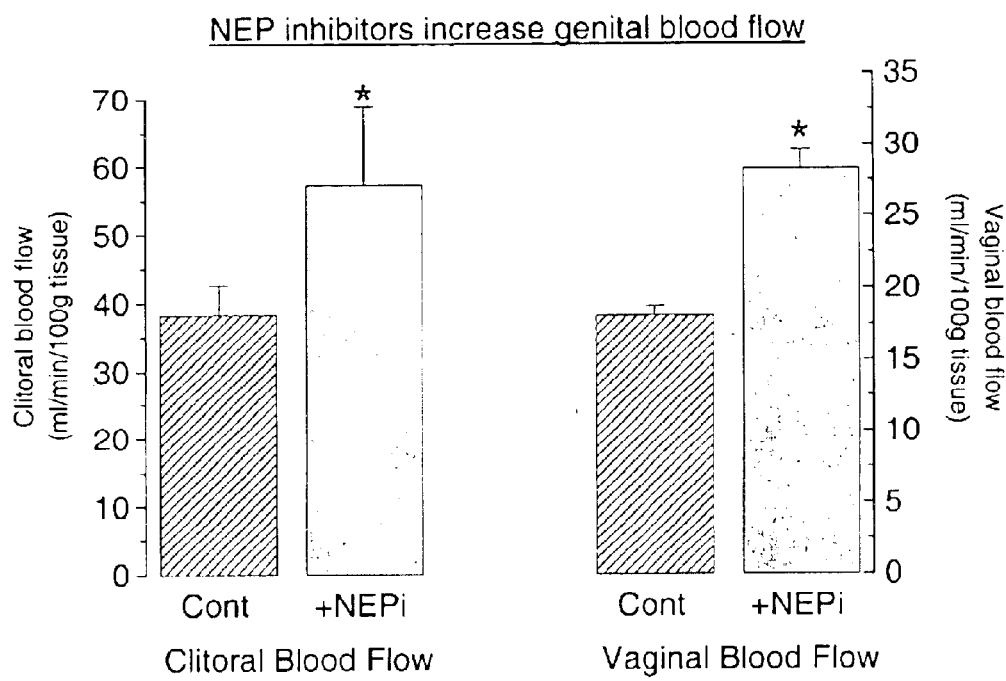
FIG. 1 describes the effect of administering a NEP inhibitor on the genital blood flow in a rabbit.

The compounds of the invention are particularly beneficial for the treatment of FSD (especially FSAD) and male sexual dysfunction (especially male erectile dysfunction (MED)).

In accordance with the invention, FSD can be defined as the difficulty or inability of a woman to find satisfaction in sexual expression. FSD is a collective term for several diverse female sexual disorders (Leiblum, S. R. (1998). Definition and classification of female sexual disorders. *Int. J. Impotence Res.*, 10, S104–S106; , Berman, J. R., Berman, L. & Goldstein, I. (1999). Female sexual dysfunction: Incidence, pathophysiology, evaluations and treatment options. *Urology*, 54, 385–391). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders.

The categories of FSD are best defined by contrasting them to the phases of normal female sexual response: desire, arousal and orgasm (Leiblum, S. R. (1998). Definition and classification of female sexual disorders. *Int. J. Impotence Res.*, 10, S104–S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. Although the compounds of the invention will improve the genital response to sexual stimulation (as in female sexual arousal disorder), in doing so it may also improve the associated pain, distress and discomfort associated with intercourse and so treat other female sexual disorders.

Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

Female sexual arousal disorder (FSAD) is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants (e.g. SSRIs) or antihypertensive agents.

Sexual pain disorders (e.g. dyspareunia and vaginismus) is characterised by pain resulting from penetration and may be caused by medications which reduce lubrication, endometriosis, pelvic inflammatory disease, inflammatory bowel disease or urinary tract problems.

The prevalence of FSD is difficult to gauge because the term covers several types of problem, some of which are difficult to measure, and because the interest in treating FSD is relatively recent. Many women's sexual problems are associated either directly with the female ageing process or with chronic illnesses such as diabetes and hypertension.

Because FSD consists of several subtypes that express symptoms in separate phases of the sexual response cycle, there is not a single therapy. Current treatment of FSD focuses principally on psychological or relationship issues. Treatment of FSD is gradually evolving as more clinical and basic science studies are dedicated to the investigation of this medical problem. Female sexual complaints are not all psychological in pathophysiology, especially for those individuals who may have a component of vasculogenic dysfunction (eg FSAD) contributing to the overall female sexual complaint. There are at present no drugs licensed for the treatment of FSD. Empirical drug therapy includes oestrogen administration (topically or as hormone replacement therapy), androgens or mood-altering drugs such as buspirone or trazodone. These treatment options are often unsatisfactory due to low efficacy or unacceptable side effects.

Since interest is relatively recent in treating FSD pharmacologically, therapy consists of the following:- psychological counselling, over-the-counter sexual lubricants, and investigational candidates, including drugs approved for other conditions. These medications consist of hormonal agents, either testosterone or combinations of oestrogen and testosterone and more recently vascular drugs, that have proved effective in male erectile dysfunction. None of these agents has been demonstrated to be very effective in treating FSD.

The Diagnostic and Statistical Manual (DSM) IV of the American Psychiatric Association defines Female Sexual Arousal Disorder (FSAD) as being: "a persistent or recurrent inability to attain or to maintain until completion of the sexual activity adequate lubrication-swelling response of sexual excitement. The disturbance must cause marked distress or interpersonal difficulty."

The arousal response consists of vasocongestion in the pelvis, vaginal lubrication and expansion and swelling of the external genitalia. The disturbance causes marked distress and/or interpersonal difficulty.

FSAD is a highly prevalent sexual disorder affecting pre-, peri- and post menopausal (±HRT) women. It is associated with concomitant disorders such as depression, cardiovascular diseases, diabetes and UG disorders.

The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

It has recently been hypothesised that there is a vascular basis for at least a proportion of patients with symptoms of FSAD (Goldstein et al., Int. J. Impot. Res., 10, S84–S90, 1998) with animal data supporting this view (Park et al., Int. J. Impot. Res., 9, 27–37, 1997).

Drug candidates for treating FSAD, which are under investigation for efficacy, are primarily erectile dysfunction therapies that promote circulation to the male genitalia. They consist of two types of formulation, oral or sublingual medications (Apomorphine, Phentolamine, phosphodiesterase type 5 (PDE5) inhibitors e.g. Sildenafil), and prostaglandin ($PGE_1$) that are injected or administered transurethrally in men, and topically to the genitalia in women.

The compounds of the invention are advantageous by providing a means for restoring a normal sexual arousal response—namely increased genital blood flow leading to vaginal, clitoral and labial engorgement. This will result in increased vaginal lubrication via plasma transudation, increased vaginal compliance and increased genital sensitivity. Hence, the compounds of the invention provide means to restore, or potentiate, the normal sexual arousal response.

Without being bound by theory, we believe that neuropeptides such as vasoactive intestinal peptide (VIP) are major neurotransmitter candidates in the control of the female sexual arousal response, especially in the control of genital blood flow. VIP and other neuropeptides are degraded/metabolised by NEP EC3.4.24.11. Thus, NEP inhibitors will potentiate the endogenous vasorelaxant effect of VIP released during arousal. This will lead to a treatment of FSAD, such as through enhanced genital blood flow and hence genital engorgement. We have shown that selective inhibitors of NEP EC 3.4.24.11 enhance pelvic nerve-stimulated and VIP-induced increases in vaginal and clitoral blood flow. In addition, selective NEP inhibitors enhance VIP and nerve-mediated relaxations of isolated vagina wall.

Thus the present invention is advantageous as it helps provide a means for restoring a normal sexual arousal response—namely increased genital blood flow leading to vaginal, clitoral and labial engorgement. This will result in increased vaginal lubrication via plasma transudation, increased vaginal compliance and increased vaginal sensitivity. Hence, the present invention provides a means to restore, or potentiate the normal sexual arousal response.

Male sexual dysfunction includes male erectile dysfunction, ejaculatory disorders such as premature ejaculation (PE), anorgasmia (inability to achieve orgasm) and desire disorders such as hypoactive sexual desire disorder (lack of interest in sex).

It is to be appreciated that all references herein to treatment include curative, palliative and prophylactic treatment.

The compounds of the invention find application in the following sub-populations of patients with FSD: the young, the elderly, pre-menopausal, peri-menopausal, post-menopausal women with or without hormone replacement therapy.

The compounds of the invention find application in patients with FSD arising from:

i) Vasculogenic etiologies eg cardiovascular or atherosclerotic diseases, hypercholesterolemia, cigarette smoking, diabetes, hypertension, radiation and perineal trauma, traumatic injury to the iliohypogastric pudendal vacular system.

ii) Neurogenic etiologies such as spinal cord injuries or diseases of the central nervous system including multiple sclerosis, diabetes, Parkinsonism, cerebrovascular accidents, peripheral neuropathies, trauma or radical pelvic surgery.

iii) Hormonal/endocrine etiologies such as dysfunction of the hypothalamic/pituitary/gonadal axis, or dysfunction of the ovaries, dysfunction of the pancreas, surgical or medical castration, androgen deficiency, high circulating levels of prolactin eg hyperprolactinemia, natural menopause, premature ovarian failure, hyper and hypothyroidism.

iv) Psychogenic etiologies such as depression, obsessive compulsive disorder, anxiety disorder, postnatal depression/"Baby Blues", emotional and relational issues, performance anxiety, marital discord, dysfunctional attitudes, sexual phobias, religious inhibition or a traumatic past experiences.

v) Drug-induced sexual dysfunction resulting from therapy with selective serotonin reuptake inhibitors (SSRis) and other antidepressant therapies (tricyclics and major tranquillizers), anti-hypertensive therapies, sympatholytic drugs, chronic oral contraceptive pill therapy.

Patients with mild to moderate MED should benefit from treatment with a compound of the invention and patients with severe MED may also respond. However, early investigations suggest that the responder rate of patients with mild, moderate and severe MED will be greater in combination with a PDE5 inhibitor. Mild, moderate and severe MED will be terms known to the man skilled in the art, but guidance can be found in *The Journal of Urology*, vol 151, 54–61 (January 1994).

The compounds of the invention find application in the following sub-populations of patients with MED: psycogenic, endocrinologic, neurogenic, arteriogenic, drug-induced sexual dysfunction (lactogenic) and sexual dysfunction related to cavernosal factors, particularly venogenic causes. These patient groups are described in more detail in Clinical Andrology vol 23,no.4, p773–782, and chapter 3 of the book by I. Eardley and K. Sethia "Erectile Dysfunction—Current Investigation and Management, published by Mosby-Wolfe.

Compounds of the invention may be prepared in known manner in a variety of ways. In the following reaction schemes and hereafter, unless otherwise stated, $R^1$, n, X and Y are as defined in the first aspect. These processes form further aspects of the invention.

Throughout the specification, general formulae are designated by Roman numerals I, II, III, IV etc. Subsets of these general formulae are defined as Ia, Ib, Ic etc, . . . IVa, IVb, IVc etc.

Compounds of general formula I may be prepared by reacting a compound of formula II (where Prot is a suitable protecting group) with an amine of formula III to give compounds of formula IV followed by deprotection (see Scheme 1). Preferred reaction conditions for the acid/amine coupling step comprise reacting II with III (or its amine salt) in the presence of an activating agent, optionally a catalyst, and an excess of an acid acceptor, in a suitable solvent. Particularly preferred reaction conditions comprise reacting II (1–1.5 equivalents), III (or its salt 1–1.5 equivalents), in the presence of 1-(3-dimethylaminopropyl)-3-ethylcarbodiimide hydrochloride (WSCDI) or N,N'-dicyclohexylcarbodiimide (DCC) (1.1–1.3 equivalents), 1-hydroxybenzotrazole hydrate (HOBT) or dimethylaminopyridine (DMAP) (1.05–1.2 equivalents), N-methyl morpholine (NMM) or triethyamine (2.3–3 equivalents), in dimethylformamide or dichloromethane at between room temperature and 90° C. for 16–18 hours.

Further particularly preferred reaction conditions comprise reacting II (1–1.5 equivalents) and 1,1'-carbonyldiimidazole (1–1.5 equivalents) in a suitable solvent (such as tetrahydrofuran, isopropylacetate or toluene) followed by addition of III (or its amine salt in which case an organic base such as triethylamine or Hunig's base is present) at a reaction temperature between room temperature and 90° C.

Scheme 1

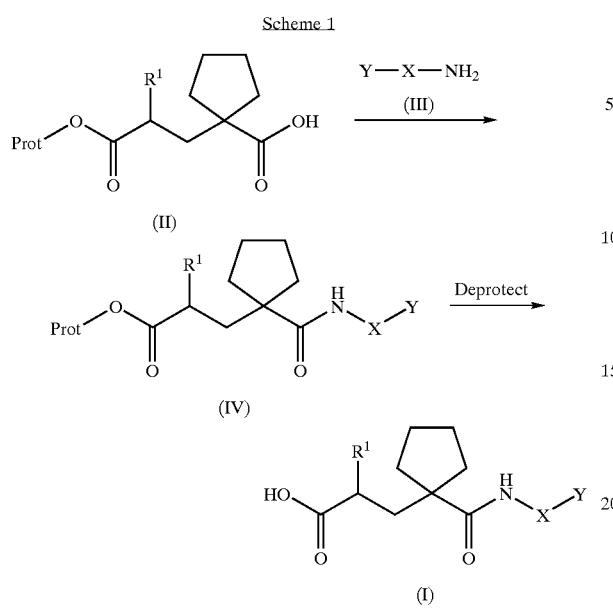

Alternatively, the acid/amine coupling step may be performed via the acid chloride in the presence of an excess of acid acceptor, in a suitable solvent. The acid chloride may be isolated or it may be generated in situ. Preferred reaction conditions comprise reacting the acid chloride of II (1–1.1 equivalents), III (or its salt, 1 to 1.5 equivalents), triethyamine or N-methyl morpholine (1.4–10 equivalents), in dichloromethane at room temperature for 24 hours. Compounds of formula II can be converted to the acid chloride in situ by treatment with oxalyl chloride in dichloromethane in the presence of a catalytic amount of dimethylformamide for 2 hours at room temperature.

Methods for deprotection of an acid group depend on the protecting group. For examples of protection/deprotection methodology see "Protective groups in Organic synthesis", T W Greene and P G M Wutz.

For example, when Prot is a tert-butyl, deprotection conditions comprise reacting IV with trifluoroacetic acid/dichloromethane (1:1–2.5 by volume), at room temperature for 2–18 hours, optionally in the presence of a carbocation scavenger, e.g. anisole (10 equivalents). When X or Y contains a hydroxy group, base hydrolysis of the intermediate trifluoroacetic acid ester may be necessary. Alternative methodology for deprotection when Prot is tert-butyl comprises treating IV with hydrochloric acid in dichloromethane at room temperature for 3 hours. For the avoidance of doubt, Prot as tert-butyl is given by way of example and is not intended to be limited to tert-butyl.

The process according to Scheme 1 forms a further aspect of the invention.

Intermediates of general formula IV are novel. Therefore according to a further aspect, the invention provides a compound of formula IV.

A number of compounds of formula II are known in the art (see EP274234-B1 and WO9113054). Other compounds of formula II can be prepared in analogous fashion.

Compounds of general formula I and II, where $R^1$ is not hydrogen, possess a chiral centre at the carbon attached to $R^1$. Individual enantiomers may be obtained by a variety of methods known to the skilled chemists, such as from a corresponding optically pure intermediate or via resolution. A preferred method of resolution is via the (+)-pseudoephadrine salt (see WO9113054, Example 10 therein).

Alternatively compounds of formula IIa, i.e. chiral compounds of formula II where $R^1$ is optionally substituted $C_{1-6}$alkyl (where Q is the substituent on the $C_{1-6}$alkyl group defined for $R^1$ in the first aspect), may be prepared by asymmetric hydrogenation of compounds of formula XI, XII, or XIII according to reaction scheme 1a.

Scheme 1a

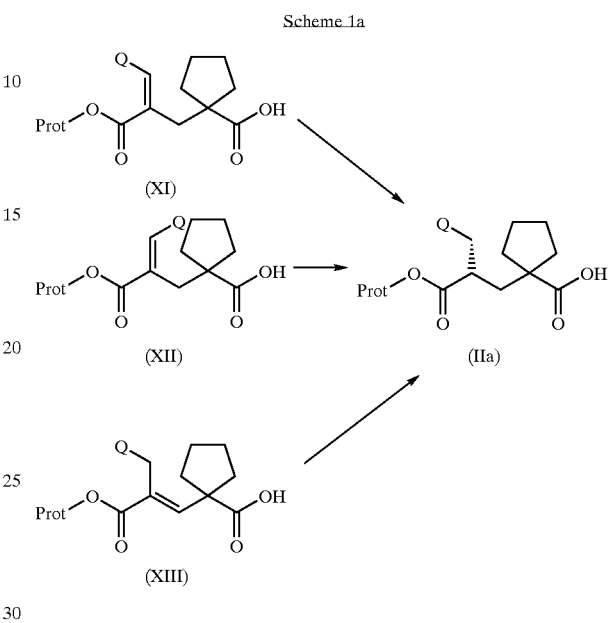

Typical hydrogenating conditions comprise treating compounds of formula XI, XII or XIII [or an organic or inorganic salt (eg sodium salt) thereof] with a suitable asymmetric hydrogenation catalyst under elevated hydrogen pressure in a suitable solvent. Preferred catalysts contain one or more chiral ligands, preferably chiral phosphine ligands, coordinated to a suitable transition metal (for example rhodium, ruthenium, iridium, paladium). Preferred catalysts are:

[(R)-(+)-2,2'-bis(diphenylphosphino)-1,1'-binaphthylchloro (para-cymene)]ruthenium chloride (*J. Org. Chem.* 1994, 59, 3064–76);

[(S)-3,3',4,4',5,5'-hexamethyl(6,6'-diphenyl)-2,2'-diyl]bis (diphenylphosphino)ruthenium bis(trifluoroacetate) (see WO 01/94359);

[(R)-(−)-4,12-bis(diisopropylphosphino)-[2.2]-paracyclophano-(1,5-cyclooctadiene)]rhodium (I) tetrafluoroborate (*J. Am. Chem. Soc.* 1997, 119, 6207–6208);

[bis-((2S,5S)-2,5-dimethyl-1-phenylphospholano)(1,5-cyclooctadiene)]rhodium (I) tetrafluoroborate (*Tetrahedron: Asymm.*, 1991, 2, 569–92); and

[(R)-(6,6'-dimethoxybiphenyl-2,2'-diyl)bis (diphenylphosphino)]ruthenium bis (trifluoroacetate) (EP398132).

Preferred reaction conditions comprise a hydrogen pressure of up to 150 psi and a reaction temperature between 0 and 100° C. (preferably 50 to 60° C.). Preferred solvents are protic, such as methanol or ethanol.

In scheme 1a, compound of formula (XIII) is the preferred starting material.

The process of scheme 1a forms a further aspect of the invention.

Alternatively compounds of formula I and IV may be prepared directly by asymmetric hydrogenation of unsaturated compounds corresponding to XI, XII and XIII.

Compounds of formula IIIa, i.e. compounds of formula III where X is —$(CH_2)_3$—, may be prepared according to reaction Scheme 2. Firstly, compounds of formula V undergo the Heck reaction with acrylonitrile in the presence of a suitable catalyst system such as palladium and excess base such as triethylamine or 4-methylmorpholine to give compounds of formula VI. Typical reaction conditions comprise 1.0–1.5 equivalents of the aryl halide, 3 equivalents of base, 0.1 equivalents of palladium catalyst (preferably palladium (II) acetate), 0.2 equivalents of phosphine ligand (preferably tri-o-tolylphosphine) in 1,4-dioxan, acetonitrile or DMF (preferably acetonitrile) at reflux. Compounds of formula VI are then subjected to catalytic hydrogenation to give compounds of formula IIIa. Typical hydrogenation conditions comprise treating VI with Raney nickel in ethanol or methanol at a pressure of 15 to 150 psig and 25 and 80° C. Preferably in ethanol at 30 psig and 25° C.

Scheme 2

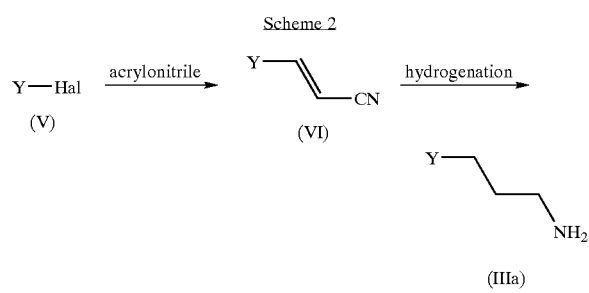

Alternatively compounds of formula VI may be prepared according to reaction scheme 3 by reacting compounds of formula VII with diethylcyanomethyl phosphonate. Typical reaction conditions comprise reacting diethylcyanomethyl phosphonate with a suitable base (for example sodium hydride, lithium chloride/Hunigs base or sodium ethoxide) in a suitable solvent at room temperature (for example dichloromethane, tetrahydrofuran or diethyl ether) followed by addition of compound of formula VII.

Scheme 3

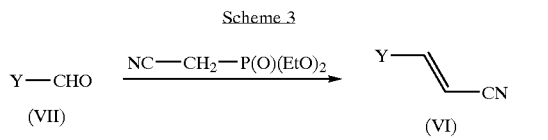

Alternatively compounds of formula IIIa may be prepared according to Scheme 4.

Scheme 4

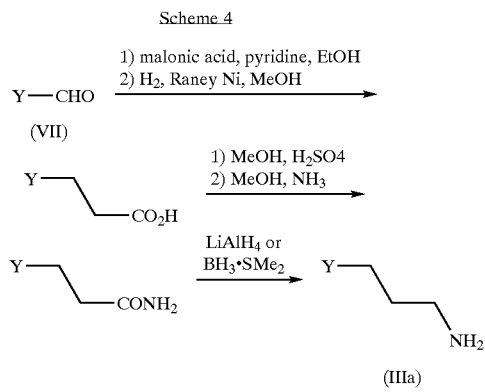

Other compounds of formula (III), (V), (VI) and (VII) are either available from commercial sources; known in the prior art; or can be prepared from compounds known in the prior art by using methods known in the prior art or by using methods described herein (see Examples and Preparations Sections).

All of the above reactions and the preparations of novel starting materials used in the preceding methods are conventional. Appropriate reagents and reaction conditions for their performance or preparation as well as procedures for isolating the desired products will be well-known to those skilled in the art with reference to literature precedents and the Examples and Preparations hereinbelow.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The compounds of the invention [particularly (2S)-2-{[1-({[3-(4-chlorophenyl)propyl]amino}carbonyl)cyclopentyl]methyl}-4-methoxybutanoic acid (Example 22)] may be combined with one or more further active ingredients selected from the list:

1) One or more naturally occurring or synthetic prostaglandins or esters thereof. Suitable prostaglandins for use herein include compounds such as alprostadil, prostaglandin $E_1$, prostaglandin $E_0$, 13,14-dihydroprosta glandin $E_1$, prostaglandin $E_2$, eprostinol, natural synthetic and semi-synthetic prostaglandins and derivatives thereof including those described in WO-00033825 and/or U.S. Pat. No. 6,037,346 issued on 14th Mar. 2000 all incorporated herein by reference, $PGE_0$, $PGE_1$, $PGA_1$, $PGB_1$, $PGF_1\alpha$, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3\alpha$, carboprost tromethamine dinoprost, tromethamine, dinoprostone, lipo prost, gemeprost, metenoprost, sulprostune, tiaprost and moxisylate.

2) One or more α-adrenergic receptor antagonist compounds also known as α-adrenoceptors or α-receptors or α-blockers. Suitable compounds for use herein include: the α-adrenergic receptor blockerss as described in PCT application WO99/30697 published on 14th Jun. 1998, the disclosures of which relating to α-adrenergic receptors are incorporated herein by reference and include, selective $\alpha_1$-adrenoceptor or $\alpha_2$-adrenoceptor blockers and non-selective adrenoceptor blockers, suitable $\alpha_1$-adrenoceptor blockers include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $\alpha_2$-blocker blockers from U.S. Pat. No. 6,037,346 [14th Mar. 2000] dibenamine, tolazoline, trimazosin and dibenamine; α-adrenergic receptors as described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $\alpha_2$-Adrenoceptor blockers include: clonidine, papaverine, papaverine hydrochloride, optionally in the presence of a cariotonic agent such as pirxamine.

3) One or more NO-donor (NO-agonist) compounds. Suitable NO-donor compounds for use herein include organic nitrates, such as mono- di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N- acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates, (NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075.

4) One or more potassium channel openers or modulators. Suitable potassium channel openers/modulators for use herein include nicorandil, cromokalim, levcromakalim, lemakalim, pinacidil, cliazoxide, minoxidil, charybdotoxin, glyburide, 4-amini pyridine, $BaCl_2$.

5) One or more dopaminergic agents, preferably apomorphine or a selective $D_2$, $D_3$ or $D_2/D_3$ agonist such as, pramipexole and ropirinol (as claimed in WO-0023056), PNU95666 (as claimed in WO-0040226).

6) One or more vasodilator agents. Suitable vasodilator agents for use herein include nimodepine, pinacidil, cyclandelate, isoxsuprine, chloroprumazine, halo peridol, Rec 15/2739, trazodone.

7) One or more thromboxane A2 agonists.

8) One or more CNS active agents.

9) One or more ergot alkoloids. Suitable ergot alkaloids are described in U.S. Pat. No. 6,037,346 issued on 14th Mar. 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride.

10) One or more compounds which modulate the action of natruretic factors in particular atrial naturetic factor (also known as atrial naturetic peptide), B type and C type naturetic factors such as inhibitors or neutral endopeptidase.

11) One or more compounds which inhibit angiotensin-converting enzyme such as enapril, and combined inhibitors of angiotensin-converting enzyme and neutral endopeptidase such as omapatrilat.

12) One or more angiotensin receptor antagonists such as losartan.

13) One or more substrates for NO-synthase, such as L-arginine.

14) One or more calcium channel blockers such as amlodipine.

15) One or more antagonists of endothelin receptors and inhibitors or endothelin-converting enzyme.

16) One or more cholesterol lowering agents such as statins (e.g. atorvastatin/Lipitor-trade mark) and fibrates.

17) One or more antiplatelet and antithrombotic agents, e.g. tPA, uPA, warfarin, hirudin and other thrombin inhibitors, heparin, thromboplastin activating factor inhibitors.

18) One or more insulin sensitising agents such as rezulin and hypoglycaemic agents such as glipizide.

19) L-DOPA or carbidopa.

20) One or more acetylcholinesterase inhibitors such as donezipil.

21) One or more steroidal or non-steroidal anti-inflammatory agents.

22) One or more estrogen receptor modulators and/or estrogen agonists and/or estrogen antagonists, preferably raloxifene, tibolone or lasofoxifene, (–)-cis-6-phenyl-5-[4-(2-pyrrolidin-1-yl-ethoxy)-phenyl]-5,6,7,8-tetrahydronaphthalene-2-ol and pharmaceutically acceptable salts thereof the preparation of which is detailed in WO 96/21656.

23) One or more modulators of cannabinoid receptors.

24) One or more of an NPY (neuropeptide Y) inhibitor, more particularly NPY1 or NPY5 inhibitor, preferably NPY1 inhibitor, preferably said NPY inhibitors (including NPY Y1 and NPY Y5) having an IC50 of less than 100 nM, more preferably less than 50 nM. An assay for identifying NPY inhibitors is presented in WO-A-98/52890 (see page 96, lines 2 to 28).

25) One or more of vasoactive intestinal protein (VIP), VIP mimetic, VIP analogue, more particularly mediated by one or more of the VIP receptor subtypes VPAC1, VPAC or PACAP (pituitary adenylate cyclase activating peptide), one or more of a VIP receptor agonist or a VIP analogue (eg Ro-125-1553) or a VIP fragment, one or more of a α-adrenoceptor antagonist with VIP combination (eg Invicorp, Aviptadil).

26) One or more of a melanocortin receptor agonist or modulator or melanocortin enhancer, such as melanotan II, PT-14, PT-141 or compounds claimed in WO-09964002, WO-00074679, WO-09955679, WO-00105401, WO-00058361, WO-00114879, WO-00113112, WO-09954358.

27) One or more of a serotonin receptor agonist, antagonist or modulator, more particularly agonists, antagonists or modulators for 5HT1A (including VML 670), 5HT2A, 5HT2C, 5HT3 and/or 5HT6 receptors, including those described in WO-09902159, WO-00002550 and/or WO-00028993.

28) one or more of an androgen such as androsterone, dehydro-androsterone, testosterone, androstanedione and a synthetic androgen.

29) one or more of an oestrogen, such as oestradiol, oestrone, oestriol and a synthetic estrogen, such as oestrogen benzoate.

30) One or more of a modulator of transporters for noradrenaline, dopamine and/or serotonin, such as bupropion, GW-320659.

31) One or more of a purinergic receptor agonist and/or modulator.

32) One or more of a neurokinin (NK) receptor antagonist, including those described in WO-09964008.

33) One or more of an opioid receptor agonist, antagonist or modulator, preferably agonists for the ORL-1 receptor.

34) One or more of an agonist or modulator for oxytocin/vasopressin receptors, preferably a selective oxytocin agonist or modulator.

35) One or more of a PDE inhibitor, more particularly a PDE 2, 3, 4, 5, 7 or 8 inhibitor, preferably PDE2 or PDE5 inhibitor and most preferably a PDE5 inhibitor (see hereinafter), said inhibitors preferably having an IC50 against the respective enzyme of less than 100 nM. Suitable cGMP PDE5 inhibitors for the use according to the present invention include:
the pyrazolo[4,3-d]pyrimidin-7-ones disclosed in EP-A-0463756; the pyrazolo[4,3-d]pyrimidin-7-ones disclosed in EP-A-0526004; the pyrazolo[4,3- d]pyrimidin-7-ones disclosed in published international patent application WO 93/06104; the isomeric pyrazolo[3,4-d]pyrimidin-4-ones disclosed in published international patent application WO 93/07149; the quinazolin-4-ones disclosed in published international patent application WO 93/12095; the pyrido[3,2-d]pyrimidin-4-ones disclosed in published international patent application WO 94/05661; the purin-6-ones disclosed in published international patent application WO 94/00453; the pyrazolo[4,3-d]pyrimidin-7-ones disclosed in published international patent application WO 98/49166; the pyrazolo[4,3-d]pyrimidin-7-ones disclosed in published international patent application WO 99/54333; the pyrazolo [4,3-d]pyrimidin-4-ones disclosed in EP-A-0995751; the pyrazolo[4,3-d]pyrimidin-7-ones disclosed in published international patent application WO 00/24745; the pyrazolo[4,3-d]pyrimidin-4-ones disclosed in EP-A-0995750; the compounds disclosed in published international application WO95/19978; the compounds disclosed in published international application WO 99/24433 and the compounds disclosed in published international application WO 93/07124. The pyrazolo[4,3-d]pyrimidin-7-ones disclosed in published international application WO 01/27112; the pyrazolo[4,3-d]pyrimidin-7-ones disclosed in published international application WO 01/27113; the compounds disclosed in EP-A-1092718 and the compounds disclose din EP-A-1092719.

Further suitable PDE5 inhibitors for the use according to the present invention include: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl] sulphonyl]-4-methylpiperazine (see EP-A-0463756); 5-(2-ethoxy-5-morpholinoacetylphenyl)-1-methyl-3-n-propyl-1, 6-dihydro-7H-pyrazolo[4,3-d]pyrimidin-7-one (see EP-A-0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8); 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132); (6R,12aR)-2,3,6,7,12,12a-hexahydro-2-methyl-6-(3,4-methylenedioxyphenyl)pyrazino[2',1':6,1] pyrido[3,4-b]indole-1,4-dione (IC-351), i.e. the compound of examples 78 and 95 of published international application WO95/19978, as well as the compound of examples 1, 3, 7 and 8; 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; and the compound of example 11 of published international application WO93/07124 (EISAI); and compounds 3 and 14 from Rotella D P, *J. Med. Chem.*, 2000, 43, 1257.

Still other suitable PDE5 inhibitors include: 4-bromo-5-(pyridylmethylamino)-6-[3-(4-chlorophenyl)-propoxy]-3 (2H)pyridazinone; 1-[4-[(1,3-benzodioxol-5-ylmethyl) amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5] imidazo[2,1-b]purin-4(3H)one; furazlocillin; cis-2-hexyl-5-methyl-3,4,5,6a,7,8,9,9a-octahydrocyclopent[4,5]-imidazo [2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl) amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866.

For treating FSD, the compounds of the invention [particularly (2S)-2-{[1-({[3-(4-chlorophenyl)propyl] amino}carbonyl)cyclopentyl]methyl}-4-methoxybutanoic acid (Example 22)] may preferably be combined with one or more active ingredients selected from the list:

a) a PDE5 inhibitor, more preferably 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil); (6R,12aR)-2,3,6,7,12,12a-hexahydro-2-methyl-6-(3,4-methylenedioxyphenyl)-pyrazino[2', 1':6,1]pyrido[3,4-b]indole-1,4-dione (IC-351); 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d] pyrimidin-7-one; and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and pharmaceutically acceptable salts thereof;

b) an NPY Y1 inhibitor;

c) a dopamine agonist such as apomorphine or a selective $D_2$, $D_3$ or $D_2/D_3$ agonist such as, pramipexole and ropirinol;

d) a melanocortin receptor agonist or modulator or melanocortin enhancer, preferably melanotan II, PT-14, PT-141;

e) an agonist, antagonist or modulator for 5HT2C;

f) an estrogen receptor modulator, estrogen agonists and/ or estrogen antagonists, preferably raloxifene, tibolone or lasofoxifene;

g) an androgen such as androsterone, dehydro-androsterone, testosterone, androstanedione and a synthetic androgen; and h) an oestrogen, such as oestradiol, oestrone, oestriol and a synthetic estrogen, such as oestrogen benzoate.

For treating MED, the compounds of the invention [particularly (2S)-2-{[1-({[3-(4-chlorophenyl)propyl] amino}carbonyl)cyclopentyl]methyl}-4-methoxybutanoic acid (Example 22)] may preferably be combined with one or more active ingredients selected from the list:

a) a PDE5 inhibitor, more preferably 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil); (6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351); 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and pharmaceutically acceptable salts thereof;

b) an NPY Y1 inhibitor;

c) a dopamine agonist (preferably apomorphine) or a selective $D_2$, $D_3$ or $D_2/D_3$ agonist such as, pramipexole and ropirinol;

d) a melanocortin receptor agonist or modulator or melanocortin enhancer, preferably melanotan II, PT-14, PT-141; and e) an agonist, antagonist or modulator for 5HT2C;

Particularly preferred combinations for treating FSD are (2S)-2-{[1-({[3-(4-chlorophenyl)propyl]amino}carbonyl) cyclopentyl]methyl}-4-methoxybutanoic acid (Example 22) and one or more active ingredients selected from the list:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil);

(6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351);

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one;

5-(5-acetyl-2-butoxy-3-pyridinyl)-3-ethyl-2-(1-ethyl-3-azetidinyl)-2,6-dihydro-7H-pyrazolo[4,3-d]pyrimidin-7-one;

apomorphine;
melanotan II;
PT-141;
lasofoxifene;
raloxifene;
tibolone;
an androgen such as androsterone, dehydro-androsterone, testosterone, androstanedione and a synthetic androgen; and
an oestrogen, such as oestradiol, oestrone, oestriol and a synthetic estrogen, such as oestrogen benzoate.

Particularly preferred combinations for treating MED are (2S)-2-{[1-({[3-(4-chlorophenyl)propyl]amino}carbonyl) cyclopentyl]methyl}-4-methoxybutanoic acid (Example 22) and one or more active ingredients selected from the list:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil);

(6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351);

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one;

5-(5-acetyl-2-butoxy-3-pyridinyl)-3-ethyl-2-(1-ethyl-3-azetidinyl)-2,6-dihydro-7H-pyrazolo[4,3-d]pyrimidin-7-one;

apomorphine;
melanotan II; and
PT-141.

If a combination of active agents are administered, then they may be administered simultaneously, separately or sequentially.

The compounds of the invention can be administered alone but, in human therapy will generally be administered in admixture with a suitable pharmaceutical excipient diluent or carrier selected with regard to the intended route of administration and standard pharmaceutical practice.

For example, the compounds of the invention, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via fast dispersing or fast dissolving dosage forms.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used, i.e. where the drug substance is insoluble a fast dispersing dosage form can be prepared and where the drug substance is soluble a fast dissolving dosage form can be prepared.

The compositions of the invention may be administered by direct injection. The composition may be formulated for parenteral, mucosal, intramuscular, intravenous, subcutaneous, ocular, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

The term "administered" includes delivery by viral or non-viral techniques. Viral delivery mechanisms include but are not limited to adenoviral vectors, adeno-associated viral (AAV) vectos, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

In addition or in the alternative the compositions (or component parts thereof) of the present invention may be administered by direct injection. In addition or in the alternative the compositions (or component parts thereof) of the present invention may be administered topically (preferably to the genitalia). In addition or in the alternative the compositions (or component parts thereof) of the present invention may be administered by inhalation. In addition or in the alternative the compositions (or component parts thereof) of the present invention may also be administered by one or more of: a mucosal route, for example, as a nasal spray or aerosol for inhalation or as an ingestable solution such as by an oral route, or by a parenteral route where delivery is by an injectable form, such as, for example, by a rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) transdermal, intraperitoneal, intracranial, intracerebroventricular, intracerebral, intravaginal, intrauterine, or parenteral (e.g., intravenous, intraspinal, subcutaneous, transdermal or intramuscular) route.

By way of example, the pharmaceutical compositions of the invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Hence, the term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intraurethrally intrasternally, intracranially, intramuscularly or subcutaneously, or they may be administered by infusion techniques. In addition, they may be administered in the form of an implant. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art. Parenteral formulations may be formulated for immediate-, delayed-, modified-, sustained-, dual-, controlled-release or pulsatile delivery.

The following dosage levels and other dosage levels herein are for the average human subject having a weight range of about 65 to 70 kg. The skilled person will readily be able to determine the dosage levels required for a subject whose weight falls outside this range, such as children and the elderly.

For oral and parenteral administration to human patients, the daily dosage level of the compounds of the invention or salts or solvates thereof will usually be from 10 to 1000 mg (in single or divided doses).

Thus, for example, tablets or capsules of the compounds of the invention or salts or solvates thereof may contain from 5 to 1000 mg, such as 5 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including FSD and MED), compounds of the invention may be taken as a single dose on an "as required" basis (i.e. as needed or desired).

The compounds of the invention can also be administered intranasally of by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

Alternatively, compounds of the invention can be administered in the form of a suppository or pessary, or they may be applied topically (preferably to the genitalia) in the form of a gel, hydrogel, lotion, solution, cream, ointment or dusting powder. The compounds of the invention may also be dermally administered. The compounds of the invention may also be transdermally administered, for example, by the use of a skin patch. They may also be administered by the ocular, pulmonary or rectal routes.

For ophthalmic use, compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin (preferably to the genitalia), compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

In a preferred embodiment, the compounds of the invention are delivered systemically (such as orally, buccally and sublingually), more preferably orally. Preferably such systemic. (most preferably oral) administration is used, to treat female sexual dysfunction, preferably FSAD.

Thus in a particularly preferred embodiment, there is provided the use of the compounds of the invention in the manufacture of a systemically delivered (preferably orally delivered) medicament for the treatment or prophylaxis of FSD, more preferably FSAD.

A preferred oral formulation uses immediate release tablets; or fast dispersing or dissolving dosage formulations (FDDFs).

In a further preferred embodiment, the compounds of the invention are administered topically, preferably directly to the female genitalia, especially the vagina.

Since NEP is present throughout the body, it is very unexpected that the compounds of the invention can be administered systemically and achieve a therapeutic response in the female genitalia without provoking intolerable (adverse) side effects. In EP 1 097 719-A1 and the animal model hereinafter, we have shown that NEP inhibitors administered to a rabbit model (in vivo) systemically increased genital blood flow, upon sexual arousal (mimiced by pelvic nerve stimulation) without adversely affecting cardiovascular parameters, such as causing a significant hypotensive or hypertensive.

Preferably the compounds of the invention are administered for the treatment of FSD in the sexually stimulated patient (by sexual stimulation we mean to include visual, auditory or tactile stimulation). The stimulation can be before, after or during said administration.

Thus the compounds of the invention enhance the pathways/mechanisms that underlie sexual arousal in the female gentialia restoring or improving the sexual arousal response to sexual stimulation.

Thus a preferred embodiment provides the use of a compound of the invention in the preparation of a medicament for the treatment or prophyaxis of FSD in the stimulated patient.

For veterinary use, a compound of the invention, is administered as a suitably acceptable formulation in accordance with normal veterinary practice and the veterinary surgeon will determine the dosing regimen and route of administration which will be most appropriate for a particular animal.

The following formulation examples are illustrative only and are not intended to limit the scope of the invention. "Active ingredient" means a compound of the invention.

Formulation 1: A tablet is prepared using the following ingredients:

|  | weight/mg |
|---|---|
| Active ingredient | 250 |
| Cellulose, microcrystalline | 400 |
| Silicon dioxide, fumed | 10 |
| Stearic acid | 5 |
| Total | 665 | the components are blended and compressed to form tablets.

Formulation 2: An intravenous formulation may be prepared as follows:

| Active ingredient | 100 mg |
|---|---|
| Isotonic saline | 1,000 ml |

Typical formulations useful for administering the compounds of the invention topically to the genitalia are as follows:

Formulation 3: A spray

Active ingredient (1.0%) in isopropanol (30%) and water.

Formulation 4: A foam

Active ingredient, acetic acid glacial, benzoic acid, cetyl alcohol, methyl parahydroxybenzoate, phosphoric acid, polyvinyl alcohol, propylene glycol, sodium carboxymethylcellulose, stearic acid, diethyl stearamide, van Dyke perfume No. 6301, purified water and isobutane.

Formulation 5: A gel

Active ingredient, docusate sodium BP, isopropyl alcohol BP, propylene glycol, sodium hydroxide, carbomer 934P, benzoic acid and purified water.

Formulation 6: A Cream

Active ingredient, benzoic acid, cetyl alcohol, lavender, compound 13091, methylparaben, propylparaben, propylene glycol, sodium carboxymethylcellulose, sodium lauryl sulfate, stearic acid, triethanolmine, acetic acid glacial, castor oil, potassium hydroxide, sorbic acid and purified water.

Formulation 7: A pessary

Active ingredient, cetomacrogol 1000 BP, citric acid, PEG 1500 and 1000 and purified water.

The invention additionally includes:

(i) A pharmaceutical composition including a compound of the invention, together with a pharmaceutically acceptable excipient, diluent or carrier.

(ii) A compound of the invention for use as a medicament.

(iii) The use of a compound of the invention as a medicament for treating or preventing a condition for which a beneficial therapeutic response can be obtained by the inhibition of neutral endopeptidase.

(iv) The use of a compound of the invention as a medicament for treating or preventing hypoactive sexual desire disorder, sexual arousal disorder, orgasmic disorder or sexual pain disorder, preferably sexual arousal disorder, orgasmic disorder or sexual pain disorder, more preferably sexual arousal disorder.

(v) A method of treating FSD or MED in a mammal including treating said mammal with an effective amount of a compound of the invention.

(vi) An FSD or MED treating pharmaceutical composition comprising a compound of the invention together with a pharmaceutically acceptable excipient, diluent or carrier.

(vii) A compound of the invention for use in treating FSD or MED.

(viii) The use of a compound of the invention in the manufacture of a medicament for treating or preventing FSD or MED.

The invention is illustrated by the following non-limiting examples in which the following abbreviations and definitions are used:

| | |
|---|---|
| Arbacel ® | filter agent |
| br | broad |
| Boc | tert-butoxycarbonyl |
| CDI | carbonyldiimidazole |
| δ | chemical shift |
| d | doublet |
| Δ | heat |
| DCCl | dicyclohexylcarbodiimide |

-continued

| | |
|---|---|
| DCM | dichloromethane |
| DMA | dimethylacetamide |
| DMF | N,N-dimethylformamide |
| DMSO | dimethylsulfoxide |
| ES$^+$ | electrospray ionisation positive scan |
| ES$^-$ | electrospray ionisation negative scan |
| Ex | Example |
| h | hours |
| HOBt | 1-hydroxybenzotriazole |
| HPLC | high pressure liquid chromatography |
| m/z | mass spectrum peak |
| min | minutes |
| MS | mass spectrum |
| NMR | nuclear magnetic resonance |
| Prec | precursor |
| Prep | preparation |
| q | quartet |
| s | singlet |
| t | triplet |
| Tf | trifluoromethanesulfonyl |
| TFA | trifluoroacetic acid |
| THF | tetrahydrofuran |
| TLC | thin layer chromatography |
| TS$^+$ | thermospray ionisation positive scan |
| WSCDI | 1-(3-dimethylaminopropyl)-3-ethylcarbodiimide hydrochloride |

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; DMSO, dimethylsulphoxide. The abbreviation psi means pounds per square inch and LRMS means low resolution mass spectrometry. Where thin layer chromatography (TLC) has been used it refers to silica gel TLC using silica gel 60 F$_{254}$ plates, R$_f$ is the distance travelled by a compound divided by the distance travelled by the solvent front on a TLC plate. Melting points were determined using a Perkin Elmer DSC7 at a heating rate of 20° C./minute).

The powder X-ray diffraction (PXRD) pattern was determined using a SIEMENS D5000 powder X-ray diffractometer fitted with an automatic sample changer, a theta-theta goniometer, automatic beam divergence slits, a secondary monochromator and a scintillation counter. The sample was prepared for analysis by packing the powder on to a silicon wafer specimen mount. The specimen was rotated whilst being irradiated with copper K-alpha$_1$ X-rays (wavelength=1.5406 Ångstroms) with the X-ray tube operated at 40 kV/40 mA. The analysis was performed with the goniometer running in step-scan mode set for a 5 second count per 0.02° step over a two theta range of 3° to 40°. In the results tables "Angle 2-Theta" is related to the interplanar spacing of the crystal, and the intensity is given as a percentage of the greatest peak (I/I$_f$).

The skilled crystallographer will appreciate that the relative intensities of the peaks may vary due to a number of factors such as orientation effects of crystals in the X-ray beam or the purity of the material being analysed or the degree of crystallinity of the sample. The peak positions may vary in sample height but the peak positions will remain substantially as tabulated. In addition, measurements using a different wavelength may result variation in the shift according to the Bragg equation–nλ=2d sin θ. These variations generated by use of alternative wavelengths are within the scope of the present invention.

EXAMPLE 1

4-Methoxy-2-{[1-({[3-(4-methoxyphenyl)propyl]amino}carbonyl)cyclopentyl]-methyl}butanoic acid

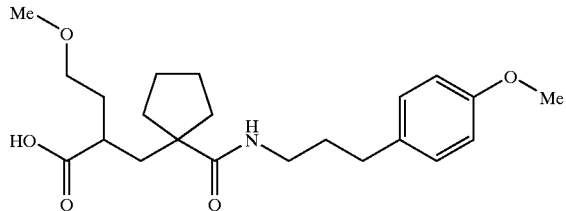

Hydrogen chloride gas was passed through a solution of the tert-butyl ester from preparation 1 (302 mg, 0.72 mmol) in dichloromethane (5 mL) at 0° C. for 30 minutes. The reaction mixture was concentrated in vacuo and the residue azeotroped with dichloromethane to give the title compound as a yellow oil, (233 mg, 0.6 mmol, 82%); $^1$H NMR (CDCl$_3$ 400 MHz) δ: 1.4–1.55 (m, 2H), 1.6–1.75 (m, 6H), 1.75–1.85 (m, 2H), 2.4–2.5 (m, 1H), 2.6 (t, 2H), 3.2 (s, 3H), 3.2–3.3 (m, 2H), 3.4 (t, 2H), 3.8 (s, 3H), 5.9 (t, 1H), 6.8 (d, 2H), 7.1 (d, 2H); LRMS: m/z 390 (M−H$^+$); and HRMS m/z 392.2430 (C$_{22}$H$_{33}$NO$_5$ requires 392.2432).

The following compounds of formula I (see Table 1) may be prepared by methods analogous to those of Example 1 from the tert-butyl ester precursor indicated.

TABLE 1

(I)

| Ex | Prec | R$^1$ | —X—Y | Data |
|---|---|---|---|---|
| 2 | Prep 2 | methoxy ethyl | 4-methoxyphenyl-CH(Me)-CH$_2$-CH$_2$- | $^1$H NMR (CDCl$_3$ 400 MHz) δ: 1.1 (t, 3H), 1.5 (m, 8H), 1.9 (m, 4H), 2.0 (m, 2H), 2.5 (m, 3H), 3.2 (s, 3H), 3.3 (m, 2H), 3.8 (t, 8H), 4.0 (s, 1H), 5.6 (d, 1H), 6.8 (d, 2H), 7.1 (d, 2H). LRMS: m/z 404 (M − H$^+$). |
| 3 | Prep 3 | methoxy ethyl | 2-chlorophenyl-O-CH$_2$-CH(Me)-CH$_2$- | $^1$H NMR (CDCl$_3$ 400 MHz) δ: 1.4 (d, 3H), 1.6 (m, 8H), 2.0 (m, 4H), 2.1 (dd, 1H), 2.5 (m, 1H), 3.2 (d, 3H), 3.4 (m, 2H), 4.0 (q, 2H), 4.4 (bs, 1H), 6.2 (m, 1H), 6.9 d, 2H), 7.2 (t, 1H), 7.4 (d, 1H). LRMS: m/z 410 (M − H$^+$). HRMS m/z 412.1885 (C$_{21}$H$_{30}$NO$_5$Cl requires 412.1813) |
| 4 | Prep 4 | methoxy ethyl | 4-fluorophenyl-CH$_2$-CH$_2$-CH$_2$- | $^1$H NMR (CDCl$_3$ 400 MHz) δ: 1.5 (m, 2H), 1.6 (m, 4H), 1.8 (t, 2H), 1.9 (m, 2H), 2.0 (m, 2H), 2.4 (m, 1H), 3.2 (s, 4H), 3.3 (t, 2H), 6.0 (bs, 1H), 6.9 (t, 2H), 7.1 (t, 2H), 10.4 (bs, 1H). LRMS: m/z 379 (M − H$^+$). |
| 5 | Prep 5 | methoxy ethyl | phenyl-CH$_2$-CH$_2$-CH$_2$-CH$_2$- | $^1$H NMR (CDCl$_3$ 400 MHz) δ: 1.4–1.6 (m, 10H), 1.8–2.0 (m, 4H), 2.4 (m, 1H), 2.6 (t, 2H), 3.2 (s, 4H), 3.3 (t, 2H), 3.3 (t, 2H), 5.9 (bs, 1H), 7.1 (m, 3H), 7.2 (t, 2H), 10.4 (bs, 1H). LRMS: m/z 374 (M − H$^+$). |
| 6 | Prep 6 | methoxy ethyl | phenyl-CH$_2$-CH$_2$-CH$_2$- | $^1$H NMR (CDCl$_3$ 400 MHz) δ: 1.5–1.6 (m, 10H), 1.8 (m, 3H), 1.9 (m, 1H), 2.0 (q, 1H), 2.5 (m, 1H), 2.6 (t, 2H), 3.2 (m, 4H), 3.4 (q, 2H), 5.9 (bs, 1H), 7.1 (d, 3H), 7.3 (m, 2H). LRMS: m/z 362 (M + H$^+$). |
| 7 | Prep 7 | methoxy ethyl | 4-hydroxyphenyl-CH$_2$-CH$_2$-CH$_2$- | $^1$H NMR (CDCl$_3$ 400 MHz) δ: 1.6 (m, 8H), 1.8 (m, 2H), 2.0 (m, 2H), 2.5 (m, 6H), 3.2 (s, 3H), 3.25 (m, 2H), 3.4 (m, 2H), 5.7 (bs, 1H), 6.7 (d, 2H), 7.0 (d, 2H). LRMS: m/z 376 (M − H$^+$). HRMS m/z 378.2288 (C$_{21}$H$_{31}$NO$_5$ requires 378.2275) |

TABLE 1-continued (I)

Structure: HO₂C-CH(R¹)-CH₂-C(cyclopentyl)(C(=O)NH-X-Y)

| Ex | Prec | R¹ | —X—Y | Data |
|---|---|---|---|---|
| 8 | Prep 8 | methoxy ethyl | (CH₂)₃-C₆H₄-CF₃ (para) | ¹H NMR (CDCl₃ 400 MHz) δ: 1.5–2.1 (m, 14H), 2.5 (m, 1H), 2.7 (m, 2H), 3.2 (s, 2H), 3.3 (m, 2H), 3.4 (m, 2H), 6.8 (s, 1H), 7.25 (d, 2H), 7.5 (d, 2H). LRMS: m/z 428 (M − H⁺). HRMS m/z 430.2206 (C₂₂H₃₀NO₄F₃ requires 430.2200) |
| 9 | Prep 9 | methoxy ethyl | (CH₂)₃-C₆H₄-Et (para) | ¹H NMR (CDCl₃ 400 MHz) δ: 1.2 (m, 3H), 1.6 (m, 8H), 1.9 (m, 4H), 2.0 (m, 2H), 2.5 (m, 1H), 2.6 (m, 4H), 3.2 (s, 3H), 3.3 (m, 2H), 3.4 (m, 2H), 5.9 (bs, 1H), 7.0 (d, 4H). LRMS: m/z 388 (M − H⁺). HRMS m/z 390.2639 (C₂₃H₃₅NO₄ requires 390.2643) |
| 10 | Prep 10 | methoxy ethyl | (CH₂)₃-C₆H₃(Me)(OMe) | ¹H NMR (CDCl₃ 400 MHz) δ: 1.5–1.85 (m, 11H), 2.0–2.2 (m, 3H), 2.3 (s, 3H), 2.5 (m, 1H), 2.6 (t, 2H), 3.25 (s, 1H), 3.3 (s, 3H), 3.35–3.5 (m, 3H), 3.8 (s, 3H), 6.7–6.8 (m, 2H), 7.1 (d, 1H), 7.6 (s, 1H). MP 148–150° C. LRMS: m/z 406 (M + H⁺). HRMS m/z 406.2597 (C₂₃H₃₅NO₅ requires 406.2588). Anal. Found C, 67.71; H, 8.74; N, 3.41. C₂₃H₃₄NO₅ 0.15 H₂O requires C, 67.67; H, 8.72; N, 3.43% |
| 11 | Prep 11 | methoxy ethyl | (CH₂)₃-(2,3-dihydrobenzofuran-5-yl) | ¹H NMR (CDCl₃ 400 MHz) δ: 0.9 (t, 2H), 1.3 (m, 2H), 1.6 (m, 8H), 1.8 (m, 3H), 1.9 (m, 1H), 2.0 (dd, 1H), 2.4 (m, 1H), 2.6 (t, 2H), 3.2 (t, 2H), 3.3 (m, 5H), 3.4 (m, 1H), 4.5 (t, 2H), 5.9 (bs, 1H), 6.7 (d, 1H), 6.9 (d, 1H), 7.0 (bs, 1H). LRMS: m/z 404 (M + H⁺). HRMS m/z 404.2434 (C₂₃H₃₄NO₅ requires 404.2431) |
| 12 | Prep 12 | methoxy ethyl | (CH₂)₃-C₆H₄-OH (ortho) | ¹H NMR (CDCl₃ 400 MHz) δ: 1.5–1.6 (m, 3H), 1.6–1.7 (m, 6H), 1.7–1.85 (m, 3H), 1.9–2.05 (m, 4H), 2.5–2.6 (m, 1H), 2.7 (t, 2H), 3.1–3.2 (m, 1H), 3.2–3.3 (t, 1H), 3.3 (s, 3H), 3.4–3.5 (m, 2H), 6.6 (bs, 1H), 6.7 (d, 1H), 6.8 (t, 1H), 7.0–7.1 (m, 2H). LRMS: m/z 376 (M + H⁺). |
| 13 | Prep 13 | methoxy ethyl | (CH₂)₃-C₆H₄-Cl (meta) | ¹H NMR (CDCl₃ 400 MHz) δ: 1.5–1.75 (m, 9H), 1.8–2.0 (m, 5H), 2.1 (dd, 1H), 2.5–2.6 (m, 1H), 2.6 (t, 2H), 3.25 (s, 3H), 3.25–3.3 (m, 2H), 3.35–3.4 (m, 2H), 5.9 (bs, 1H), 7.1 (d, 1H), 7.15–7.25 (m, 3H). LRMS: m/z 396 (M + H⁺). HRMS m/z 396.1949 (C₂₁H₃₁NO₄Cl requires 396.1936) |

TABLE 1-continued (I)

$$\text{HO}_2\text{C}-\overset{R^1}{\underset{}{\text{CH}}}-\text{CH}_2-\overset{\text{cyclopentyl}}{\underset{\underset{O}{\|}}{C}}-\overset{H}{\underset{}{N}}-X-Y$$

| Ex | Prec | R¹ | —X—Y | Data |
|---|---|---|---|---|
| 14 | Prep 14 | methoxy ethyl | -(CH₂)₃-(2-Cl-C₆H₄) | ¹H NMR (CDCl₃ 400 MHz) δ: 1.5–1.75 (m, 9H), 1.75–2.0 (m, 5H), 2.1 (dd, 1H), 2.45–2.55 (m, 1H), 2.75 (t, 2H), 3.25 (s, 3H), 3.20–3.3 (m, 2H), 3.35–3.4 (m, 2H), 6.1 (bs, 1H), 7.1–7.25 (m, 4H). LRMS: m/z 396 (M + H⁺). HRMS m/z 396.1946 (C₂₁H₃₁NO₄Cl requires 396.1936) |
| 15 | Prep 15 | methoxy ethyl | -(CH₂)₃-(4-Cl-C₆H₄) | ¹H NMR (CDCl₃ 400 MHz) δ: 1.5–1.75 (m, 9H), 1.8–1.95 (m, 5H), 2.05 (dd, 1H), 2.4–2.5 (m, 1H), 2.6 (t, 2H), 3.25 (s, 3H), 3.20–3.3 (m, 2H), 3.35–3.4 (m, 2H), 6.1 (bs, 1H), 7.1 (d, 2H), 7.2 (d, 2H). LRMS: m/z 396 (M + H⁺). HRMS m/z 396.1943 (C₂₁H₃₁NO₄Cl requires 396.1936) |
| 16 | Prep 16 | (R)-Pr | -(CH₂)₃-(4-OMe-C₆H₄) | ¹H NMR (CDCl₃ 400 MHz) δ: 0.8 (t, 3H), 1.2-1.95 (m, 16H), 2.3 (m, 1H), 2.55 (m, 2H), 3.25 (m, 2H), 3.7 (s, 3H), 5.7 (s, 1H), 6.8 (d, 2H), 7.1 (d, 2H). LRMS: m/z 374 (M − H⁻). HRMS m/z 376.2485 (C₂₂H₃₅NO₄ requires 376.2482) |
| 17 | Prep 17 | (R)-Me | -(CH₂)₃-(4-OMe-C₆H₄) | ¹H NMR (CDCl₃ 400 MHz) δ: 1.18 (d, 3H), 1.45–1.96 (m, 11H), 2.08 (m, 1H), 2.41 (m, 1H), 2.59 (t, 2H), 3.3 (t, 2H), 3.8 (s, 3H), 5.67 (m, 1H), 6.82 (d, 2H), 7.08 (d, 2H). LRMS: m/z 348 (M + H⁺). |
| 18 | Prep 18 | H | -(CH₂)₃-(4-OMe-C₆H₄) | ¹H NMR (CDCl₃ 400 MHz) δ: 1.47 (m, 2H), 1.73 (m, 4H), 1.77–2.00 (m, 6H), 2.31 (m, 2H), 2.60 (t, 2H), 3.29 (m, 2H), 3.8 (s, 3H), 5.57 (m, 1H), 6.82 (d, 2H), 7.11 (d, 2H). LRMS: m/z 334 (M + H⁺). |
| 19 | Prep 19 | H | -(CH₂)₃-(3-Cl-C₆H₄) | ¹H NMR (CDCl₃ 400 MHz) δ: 1.47 (m, 2H), 1.73 (m, 4H), 1.77–2.00 (m, 6H), 2.31 (m, 2H), 2.60 (t, 2H), 3.29 (m, 2H), 3.8 (s, 3H), 5.57 (m, 1H), 6.82 (d, 2H), 7.11 (d, 2H). LRMS: m/z 338 (M + H⁺). |
| 20 | Prep 20 | H | -(CH₂)₃-(4-Cl-C₆H₄) | ¹H NMR (CDCl₃ 400 MHz) δ: 1.40–1.98 (m, 12H), 2.37 (t, 2H), 2.58 (t, 2H), 3.23 (q, 2H), 5.57 (m, 1H), 7.07 (d, 2H), 7.20 (d, 2H). LRMS: m/z 338 (M + H⁺). |
| 21 | Prep 21 | H | -(CH₂)₃-(2,3-dihydrobenzofuran-5-yl) | ¹H NMR (CDCl₃ 400 MHz) δ: 1.46 (m, 2H), 1.66 (m, 4H), 1.73–1.98 (m, 6H), 2.29 (t, 2H), 2.58 (t, 2H), 3.17 (t, 2H), 3.26 (q, 2H), 4.53 (t, 2H), 6.59 (m, 1H), 6.70 (d, 1H), 6.90 (d, 1H), 7.01 (s, 1H). MP 94.5–97.0° C. LRMS: m/z 346 (M + H⁺). Anal. Found C, 68.50; H, 7.78; N, 4.01. C₂₀H₂₇NO₄ 0.25 H₂O requires C, 68.65; H, 7.92; N, 4.00% |

TABLE 1-continued

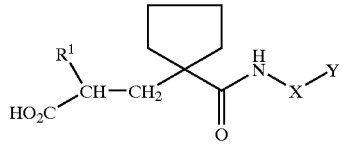

(I)

| Ex | Prec | R¹ | —X—Y | Data |
|---|---|---|---|---|
| 22 | Prep 22 | (S)-methoxy-ethyl | 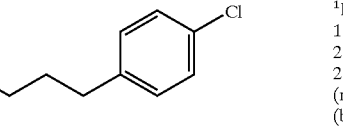 4-Cl-phenyl | ¹H NMR (CDCl₃ 400 MHz) δ: 1.5–1.7 (m, 9H), 1.75–1.95 (m, 5H), 2.05 (dd, 1H), 2.4–2.5 (m, 1H), 2.6 (t, 2H), 3.25 (s, 3H), 3.20–3.3 (m, 2H), 3.35–3.4 (m, 2H), 6.1 (bs, 1H), 7.1 (d, 2H), 7.2 (d, 2H). MP 75–77° C. LRMS: m/z 394 (M − H⁻). |
| 23 | Prep 23 | (S)-methoxy-ethyl | 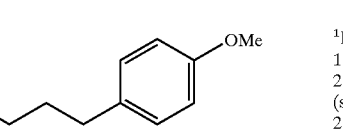 4-F-phenyl | ¹H NMR (CDCl₃ 400 MHz) δ: 1.4–2.1 (m, 14H), 2.45 (m, 1H), 2.55 (m, 2H), 3.2 (s, 3H), 3.25 (m, 2H), 3.35 (m, 2H), 5.9 (bs, 1H), 6.9 (m, 2H), 7.1 (m, 2H), 10.4 (bs, 1H). LRMS: m/z 378 (M − H⁺). [α]_D +0.4 (EtOH, c 1). HRMS m/z 380.2232 (C₂₂H₃₃NO₅ requires 380.2225). Anal. Found C, 63.73; H, 7.92; N, 4.11. C₂₁H₃₀NO₄F 0.6H₂O requires C, 63.62; H, 8.04; N, 3.82% |
| 24 | Prep 24 | (S)-methoxy-ethyl | 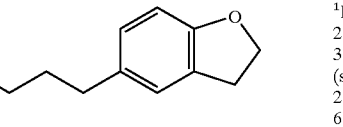 4-OMe-phenyl | ¹H NMR (CDCl₃ 400 MHz) δ: 1.4–1.70 (m, 8H), 1.80–2.05 (m, 6H), 2.4–2.5 (m, 1H), 2.6 (t, 2H), 3.2 (s, 3H), 3.2–3.3 (m, 2H), 3.4 (t, 2H), 3.8 (s, 3H), 5.8 (bs, 1H), 6.8 (d, 2H), 7.1 (d, 2H). LRMS: m/z 390 (M − H⁻). [α]_D −0.01 (EtOH, c 1.87). HRMS m/z 392.2425 (C₂₂H₃₃NO₅ requires 392.2432) |
| 25 | Prep 25 | (S)-methoxy-ethyl | 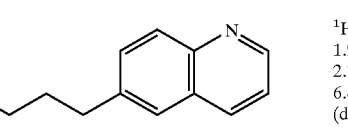 dihydrobenzofuran | ¹H NMR (CDCl₃ 400 MHz) δ: 1.41–2.06 (m, 14H), 2.43–2.60 (m, 2H), 32.57 (t, 2H), 3.18 (t, 2H), 3.33 (s, 3H), 3.24–3.4 (m, 4H), 4.53 (t, 2H), 5.80 (bs, 1H), 6.66 (d, 1H), 6.88 (d, 1H), 7.0 (s, 1H). LRMS: m/z 402 (M − H⁻). [α]_D 0.00 (EtOH, c 0.93). Anal. Found C, 66.85; H, 8.24; N, 3.35. C₂₅H₃₅NO₅ 0.5 H₂O requires C, 66.97; H, 8.31; N, 3.40% |
| 26 | Prep 26 | H | 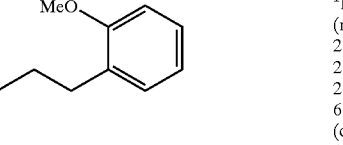 quinolinyl | ¹HNMR (CDCl₃, 400 MHz) δ: 1.13–1.98 (m, 10H), 2.16–2.28 (m, 4H), 2.70–3.03 (m, 4H), 5.60 (brs, 1H), 6.88 (d, 1H), 7.40 (d, 1H), 7.57 (d, 1H), 8.08 (d, 1H), 8.17 (d, 1H), 8.86 (d, 1H). LRMS: ES⁻ m/z 353 (M − H). |
| 27 | Prep 27 | methoxy ethyl | 2-OMe-phenyl | ¹HNMR (CDCl₃, 400 MHz) δ: 1.20 (m, 2H), 1.60 (m, 8H), 1.80 (t, 2H), 1.90 (m, 3H), 2.50 (m, 1H), 2.0 (t, 2H), 3.20 (m, 5H), 3.40 (m, 2H), 3.80 (s, 3H), 6.00 (brs, 1H), 6.90 (m, 2H), 7.10 (d, 2H), 7.20 (d, 2H). LRMS: ES+ m/z 392 (M + H). HRMS: m/z 392.2431 (C₂₂H₃₃NO₅ requires 392.2422) |

TABLE 1-continued (I)
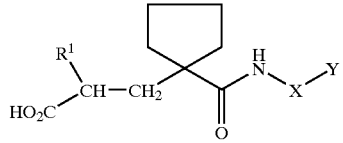

| Ex | Prec | R¹ | —X—Y | Data |
|---|---|---|---|---|
| 28 | Prep 28 | methoxy ethyl | 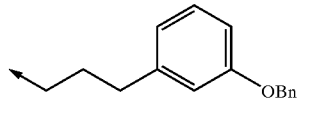 | ¹HNMR (CDCl₃, 400 MHz) δ: 1.30 (m, 2H), 1.40–1.70 (m, 6H), 1.80 (m, 2H), 1.90–2.10 (m, 3H), 2.30 (s, 3H), 2.42 (m, 2H), 2.60 (t, 2H), 3.20 (s, 3H), 3.30 (m, 2H), 3.40 (m, 2H), 5.85 (brs, 1H), 7.15 (brs, 4H). LRMS: ES+ m/z 376 (M + H). HRMS m/z 376.2484 (C₂₂H₃₃NO₄ requires 376.2483). |
| 29 | Prep 29 | methoxy ethyl | 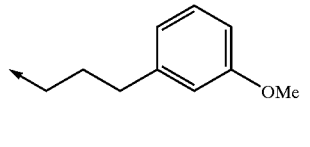 | ¹HNMR (CDCl₃, 400 MHz) δ: 1.60 (m, 8H), 1.90 (m, 4H), 2.00 (m, 2H), 2.50 (m, 1H), 2.60 (t, 2H), 3.20 (m, 5H), 3.30 (q, 2H), 5.00 (s, 2H), 5.80 (brs, 1H), 6.90 (m, 3H), 7.20 (t, 2H), 7.40 (m, 5H). LRMS: ES+ 468 (M + H). |
| 30 | Prep 30 | methoxy ethyl | 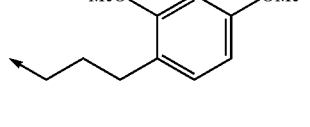 | ¹HNMR (CDCl₃, 400 MHz) δ: 1.43–1.76 (m, 10H), 1.80–2.15 (m, 4H), 2.50 (m, 1H), 2.60 (t, 2H), 3.25 (s, 3H), 3.30 (m, 2H), 3.35 (m, 2H), 3.78 (d, 2H), 4.01 (t, 1H), 5.75–5.95 (brm, 1H), 6.10–6.45 (brm, 1H), 6.70 (m, 1H), 6.90 (m, 1H), 7.18 (m, 1H). LRMS: ES+ 392.2 (M + H). |
| 31 | Prep 31 | methoxy ethyl | 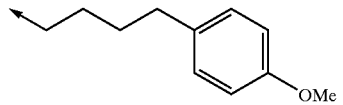 | ¹HNMR (CDCl₃, 400 MHz) 1.50–1.70 (m, 8H), 2.00 (m, 3H), 2.10 (dd, 1H), 2.30 (m, 1H), 2.60 (t, 2H), 3.20 (m, 2H), 3.30(s, 3H), 3.40 (q, 2H), 3.8 (d, 6H), 6.10 (brs, 1H), 6.30 (brd, 2H), 7.00 (d, 1H). LRMS: ES+ 422.3 (M + H). Anal. Found C 65.16; H 8.46; N 3.17%. (C₂₃H₃₅NO₆ Requires: C 65.53; H 8.36; N 3.32%) |
| 32 | Prep 32 | (S)-methoxy ethyl | 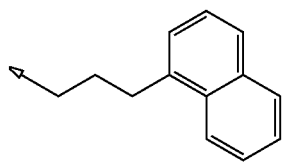 | ¹HNMR (CDCl₃, 300 MHz) 1.50–1.78 (m, 12H), 1.91–2.13 (m, 4H), 1.48–1.62 (m, 3H), 3.20–3.47 (m, 7H), 3.80 (s, 3H), 5.82 (t, 1H), 6.83 (d, 2H), 7.10 (d, 2H). LRMS: TS⁺ m/z 406 (M + H). |
| 33 | Prep 33 | H | 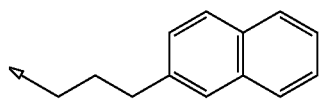 | ¹HNMR (CDCl₃, 400 MHz) δ: 1.40 (m, 2H), 1.55 (m, 4H), 1.80 (m, 4H), 1.90 (m, 2H), 2.2 (m, 2H), 3.1 (t, 2H), 3.3 (q, 2H), 5.60 (brs, 1H), 7.25 (m, 1H), 7.35 (m, 1H), 7.45 (m, 2H), 7.70 (d, 1H), 7.80 (d, 1H), 7.95 (d, 1H). LRMS: ES⁻ m/z 352 (M − H), 705 (2 M − H). |
| 34 | Prep 34 | H |  | ¹HNMR (CDCl₃, 400 MHz) δ: 1.40 (m, 2H), 1.50 (m, 4H), 1.70–1.90 (m, 6H), 2.20 (m, 2H), 2.80 (t, 2H), 3.30 (q, 2H), 5.60 (brs, 1H), 7.25 (d, 1H), 7.40 (m, 2H), 7.55 (s, 1H), 7.70 (m, 3H). LRMS: ES⁻ m/z 352 (M − H), 705 (2M − H). |

TABLE 1-continued

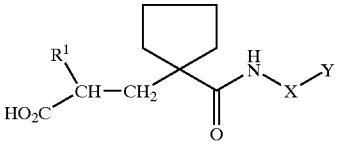

(I)

| Ex | Prec | R¹ | —X—Y | Data |
|---|---|---|---|---|
| 35 | Prep 35 | (S)-methoxy ethyl | 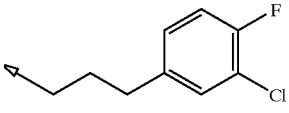 | ¹HNMR (CD₃OD, 300 MHz) δ: 1.45–1.88 (m, 8H), 2.0–2.12 (m, 3H), 2.45 (c, 1H), 2.65 (t, 2H), 3.20 (t, 2H), 3.25 (s, 3H), 3.35 (t, 2H), 7.10–7.20 (m, 2H), 7.35 (d, 1H). LRMS: ES⁻ m/z 412 (M − H). CHN: 0.15 CH₂Cl₂ |
| 36 | Prep 36 | (S)-methoxy ethyl | 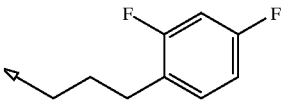 | ¹HNMR (CDCl₃, 400 MHz) δ: 1.45–1.70 (m, 10H), 1.75–1.83 (m, 1H), 1.85–1.96 (m, 3H), 2.05–2.15 (m, 2H), 2.43–2.52 (m, 1H), 2.57 (t, 2H), 3.21 (s, 3H), 3.35 (bs, 2H), 5.80 (bs, 1H), 6.89 (d, 1H), 6.95 (d, 1H), 7.23–7.30 (m, 1H). LRMS: ES⁺ m/z 436 (M + Na). Found: C, 59.36, 59.17; H, 7.30, 7.27; N, 2.68, 2.69. Requires: C, 58.96; H, 7.46; N, 3.03 (M + 0.29 pentane + 0.11 TFA + 0.80 water) |
| 37 | Prep 37 | (S)-methoxy ethyl | 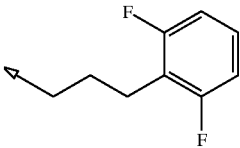 | ¹HNMR (CD₃OD, 400 MHz) δ: 1.25 (m, 1H), 1.40–1.82 (m, 11H), 2.0 (m, 3H), 2.38 (c, 1H), 2.60 (t, 2H), 3.08–3.18 (m, 7H), 5.46 (brs, 1H), 6.80 (d, 2H), 7.25 (s, 1H). LRMS: ES⁻ m/z 396 (M − H). CHN: 0.36 CH₂Cl₂ 0.6 H₂O |
| 38 | Prep 38 | H | 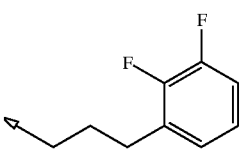 | ¹HNMR (CD₃OD, 400 MHz) δ: 1.23 (d, 2H), 1.32–1.45 (m, 4H), 1.72 (t, 2H), 1.81 (t, 2H), 1.93 (m, 2H), 2.16 (t, 2H), 2.60 (t, 2H), 3.15 (t, 2H), 6.77 (m, 2H), 7.08 (t, 1H). LRMS: ES⁻ m/z 338 (M − H). CHN: 0.51 CH₂Cl₂ |
| 39 | Prep 39 | H | 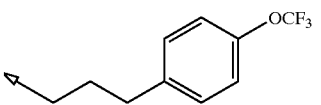 | ¹HNMR (CD₃OD, 400 MHz) δ: 1.45 (m, 2H), 1.51–1.65 (m, 4H), 1.75 (t, 2H), 1.80 (t, 2H), 1.95 (m, 2H), 2.15 (t, 2H), 2.61 (t, 2H), 3.18 (t, 2H), 6.85–7.95 (m, 3H). LRMS: ES⁻ m/z 338 (M − H). CHN: 0.08 H₂O) |
| 40 | Prep 40 | H | 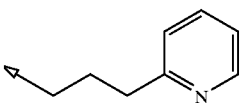 | ¹HNMR (CD₃OD, 400 MHz) δ: 1.47 (m, 2H), 1.52–1.69 (m, 4H), 1.75 (t, 2H), 1.88 (t, 2H), 2.0 (m, 2H), 2.17 (t, 2H), 2.60 (t, 2H), 3.18 (t, 2H), 7.1 (d, 2H), 7.23 (d, 2H), 7.68 (brs, 1H). LRMS: ES⁻ m/z 386 (M − H). CHN: 0.1 H₂O |
| 41 | Prep 41 | (S)-methoxy ethyl | | ¹HNMR (CDCl₃, 300 MHz) δ: 1.40–2.80 (m, 12H), 2.16–2.43 (m, 2H), 2.90–3.08 (m, 2H), 3.18–3.50 (m, 7H), 6.18 (s, 1H), 7.20–7.31 (m, 2H), 7.77 (t, 1H), 8.50 (d, 1H). |

TABLE 1-continued (I)

Structure: cyclopentane ring with substituent $-C(R^1)H-CH_2-$ connected to $HO_2C$ on one side, and $-C(=O)-NH-X-Y$ on the other side.

| Ex | Prec | R¹ | —X—Y | Data |
|---|---|---|---|---|
| 42 | Prep 42 | H | (propyl linker to indane) | ¹HNMR (CDCl₃, 400 MHz) δ: 1.35–1.43 (m, 2H), 1.55–1.65 (m, 4H), 1.66–1.90 (m, 6H), 1.97–2.05 (m, 2H), 2.20–2.29 (m, 2H), 2.58 (t, 2H), 2.80–2.90 (m, 4H), 3.24–3.30 (m, 2H), 5.49 (bs, 1H), 6.90 (d, 1H), 6.92 (s, 1H), 7.10 (d, 1H). LRMS: ES⁻ m/z 342 (M − H). Found: C, 73.71, 73.77; H, 9.08, 9.18; N, 3.36, 3.36. Requires: C, 73.81; H, 9.06; N, 3.75 (M + 0.06 EtOAc + 0.34 pentane) |
| 43 | Prep 43 | (S)-methoxy ethyl | (propyl linker to 2,3-dihydro-1,4-benzodioxine) | ¹HNMR (CDCl₃, 300 MHz) δ: 1.50–2.12 (m, 14H), 2.48–2.62 (m, 3H), 3.23–3.47 (m, 7H), 4.25 (s, 3H), 5.77 (t, 1H), 6.65–6.75 (m, 2H), 6.81 (d, 2H). LRMS: TS⁺ m/z 420 (M + H). |
| 44 | Prep 44 | (S)-methoxy ethyl | (propyl linker to 4-(pyridin-2-yl)phenyl) | ¹HNMR (CDCl₃, 300 MHz) δ: 1.37–2.02 (m, 14H), 2.40–2.51 (m, 1H), 2.68–2.83 (q, 2H), 3.23–3.50 (m, 7H), 5.61 (s, 1H), 7.22–7.38 (m, 3H), 7.67–7.90 (m, 3H), 8.72 (d, 1H). LRMS: TS⁺ m/z 439 (M + H). |
| 45 | Prep 45 | H | (propyl linker to 4-bromophenyl) | ¹HNMR (CD₃OD, 400 MHz) δ: 1.42–1.51 (m, 2H), 1.55–1.68 (m, 4H), 1.72–1.79 (m, 2H), 1.83–1.90 (m, 2H), 1.98–2.05 (m, 2H), 2.17 (t, 2H), 2.55 (t, 2H), 3.17 (t, 2H), 7.06 (d, 2H), 7.35 (d, 2H). LRMS: ES⁻ m/z 380 (M − H). Found: C, 57.52, 57.59; H, 6.65, 6.66; N, 3.37, 3.35. Requires: C, 57.19; H, 6.58; N, 3.58 (M + 0.13 pentane) |
| 46 | Prep 46 | H | (propyl linker to 1-methyl-1H-indazol-5-yl) | ¹HNMR (CDCl₃, 400 MHz) δ: 1.41–1.55 (m, 2H), 1.57–1.73 (m, 4H), 1.82–2.00 (m, 6H), 2.33 (t, 2H), 2.78 (t, 2H), 3.33 (q, 2H), 4.07 (s, 3H), 5.59 (t, 1H), 7.22–7.36 (m, 2H), 7.51 (s, 1H), 7.91 (s, 1H). |
| 47 | Prep 67 | H | (propyl linker to 4-cyanophenyl) | ¹HNMR (CDCl₃, 400 MHz) δ: 1.45–1.52 (m, 2H), 1.58–1.65 (m, 4H), 1.75–1.90 (m, 4H), 1.93–1.95 (m, 2H), 2.25–2.29 (m, 2H), 2.66 (t, 2H), 3.22–3.30 (m, 2H), 5.67 (bs, 1H), 7.27 (d, 2H), 7.51 (d, 2H). ES⁻ m/z 327 (M − H). Found: C, 58.78, 58.89; H, 6.96, 6.96; N, 6.40, 6.41. Requires: C, 58.57; H, 6.58; N, 6.80 (M + 1.17 water + 0.55 TFA). |
| 48 | Prep 47 | H | (propyl linker to 2-methyl-2H-indazol-5-yl) | ¹HNMR (CDCl₃, 400 MHz) δ: 1.49 (m, 2H), 1.65 (m, 4H), 1.90 (m, 6H), 2.30 (t, 2H), 2.77 (t, 2H), 3.35 (q, 2H), 4.27 (s, 3H), 5.63 (brs, 1H), 7.23 (d, 2H), 7.45 (s, 1H), 7.70 (d, 2H), 7.87 (s, 1H). LRMS: m/z 358 (M + H), TS. |

TABLE 1-continued (I)

| Ex | Prec | R¹ | —X—Y | Data |
|----|------|-----|------|------|
| 49 | Prep 48 | H | (4-(chroman-6-yl)butyl) | ¹HNMR (CDCl₃, 400 MHz) δ: 1.40–1.53 (m, 2H), 1.74–2.03 (m, 12H), 2.28 (t, 2H), 2.56 (t, 2H), 2.77 (t, 2H), 3.27 (t, 2H), 4.14 (t, 2H), 5.56 (brs, 1H), 6.71 (d, 1H), 6.82 (s, 1H), 6.88 (d, 1H). LRMS: m/z 358 (M − H), ES⁻. Anal. Found C, 69.81; H, 8.09; N, 3.88%. C₂₁H₂₉NO₄ requires C, 70.17; H, 8.13; N, 3.90%. |
| 50 | Prep 49 | H | (3-(4-methylthiophenyl)propyl) | ¹HNMR (CDCl₃, 400 MHz) δ: 1.37–1.45 (m, 2H), 1.56–1.59 (m, 4H), 1.73–1.90 (m, 6H), 2.23 (t, 2H), 2.40 (s, 3H), 2.55 (t, 2H), 3.24 (dt, 2H), 5.60 (brs, 1H), 7.05 (d, 2H), 7.14 (d, 2H). LRMS: m/z 348 (M − H), ES⁻. Anal. Found C, 63.68; H, 7.66; N, 3.67%. C₁₉H₂₇NO₃S. 0.09 TFA requires C, 64.04; H, 7.59; N, 3.89%. |
| 51 | Prep 50 | H | (3-(2,3-dihydrobenzofuran-5-yl)butyl) with Me | ¹HNMR (CDCl₃, 400 MHz) δ: 1.20 (d, 3H), 1.40 (m, 2H), 1.50–1.90 (m, 10H), 2.20 (m, 2H), 2.60 (m, 1H), 3.05 (m, 1H), 3.15 (t, 2H), 3.25 (m, 1H), 4.50 (t, 2H), 5.50 (brs, 1H), 6.70 (d, 1H), 6.90 (d, 1H), 7.0 (s, 1H). LRMS: m/z 358 (M − H), ES⁻. |
| 52 | Prep 51 | H | (3-(2,3-dihydrobenzofuran-5-yl)-2-methylpropyl) | ¹HNMR (CDCl₃, 400 MHz) δ: 1.10 (d, 3H), 1.40 (m, 2H), 1.60 (m, 6H), 1.90 (m, 4H), 2.30 (m, 2H), 2.50 (t, 2H), 3.10 (t, 2H), 4.00 (m, 1H), 4.50 (t, 2H), 5.40 (d, 1H), 6.65 (d, 1H), 6.85 (d, 1H), 6.95 (s, 1H). LRMS: m/z 358 (M − H), ES⁻. |
| 53 | Prep 52 | (S)-methoxy ethyl | (3-(4-methylthiophenyl)propyl) | ¹HNMR (CDCl₃, 400 MHz) δ: 1.45–1.64 (m, 8H), 1.78–1.94 (m, 6H), 2.41 (s, 3H), 2.45–2.50 (m, 1H), 2.58 (t, 2H), 3.22–3.27 (m, 5H), 3.32–3.37 (m, 2H), 5.72 (brs, 1H), 7.07 (d, 2H), 7.15 (d, 2H). LRMS: m/z 406 (M − H), ES⁻. Anal. Found C, 65.02; H, 8.54; N, 2.87%. C₂₂H₃₃NO₄S. 0.26 EtOAc requires C, 64.84; H, 8.46; N, 3.16%. |
| 54 | Prep 53 | H | (3-(2,3-dihydrobenzofuran-3-yl)propyl) | ¹HNMR (CDCl₃, 400 MHz) δ: 1.43–1.53 (m, 3H), 1.58–1.69 (m, 8H), 1.70–1.82 (m, 1H), 1.83–2.01 (m, 4H), 2.28 (t, 2H), 3.33 (t, 2H), 3.42 (m, 1H), 4.23 (t, 1H), 4.60 (t, 1H), 5.70 (brs, 1H), 6.78 (dd, 1H), 6.88 (t, 1H), 7.11 (t, 1H), 7.18 (dd, 1H). LRMS: m/z 330 (M − H) ES⁻ 332 MH⁺ 354 MNa⁺ ES⁺. Anal. Found C, 69.81; H, 8.09; N, 3.88%. C₂₁H₂₉NO₄ requires C, 70.17; H, 8.13; N, 3.90%. |

TABLE 1-continued (I)

| Ex | Prec | R¹ | —X—Y | Data |
|---|---|---|---|---|
| 55 | Prep 54 | (S)-methoxy ethyl | (4-(2,3-dihydrobenzofuran-7-yl)butyl) | ¹HNMR (CDCl₃, 400 MHz) δ: 1.47–1.70 (m, 8H), 1.73–1.79 (m, 2H), 1.94–2.06 (m, 5H), 2.45–2.51 (m, 1H), 2.55 (t, 2H), 3.15–3.18 (m, 4H), 3.23 (s, 3H), 3.33–3.36 (m, 2H), 4.53 (t, 2H), 6.26 (brs, 1H), 6.75 (dd, 1H), 6.89 (d, 1H), 7.02 (d, 1H). LRMS: m/z 402 (M − H), ES⁻. Anal. Found C, 66.36; H, 8.20; N, 3.29%. $C_{23}H_{33}NO_5$. 0.14 TFA requires C, 66.66; H, 7.96; N, 3.34%. |
| 56 | Prep 55 | (S)-methoxy ethyl | (4-(7-methyl-2,3-dihydrobenzofuran-5-yl)butyl) | ¹HNMR (CDCl₃, 400 MHz) δ: 1.50–1.70 (m, 6H), 1.80 (t, 2H), 1.90–2.05 (m, 5H), 2.20 (s, 3H), 2.50 (m, 2H), 2.55 (t, 2H), 3.15 (t, 2H), 3.30 (m, 5H), 3.40 (m, 2H), 4.50 (t, 2H), 5.80 (brs, 1H), 6.70 (s, 1H), 6.85 (s, 1H). LRMS: m/z 432 M − H), ES⁻. |
| 57 | Prep 56 | (S)-methoxy ethoxy methyl | (4-(2,3-dihydrobenzofuran-5-yl)butyl) | ¹HNMR (CDCl₃, 400 MHz) δ: 1.43–2.06 (m, 12H), 2.57 (t, 2H), 2.63 (brm, 1H), 3.18 (t, 2H), 3.27 (q, 2H), 3.34 (s, 3H), 3.44–3.53 (m, 3H), 3.58 (t, 2H), 3.64 (brt, 1H), 4.53 (t, 2H), 5.90 (brs, 1H), 6.68 (d, 1H), 6.89 (d, 1H), 7.00 (s, 1H). LRMS: m/z 432 (M − H), ES⁻. Anal. Found C, 64.90; H, 8.16; N, 2.99%. $C_{24}H_{35}NO_6$. 0.5 H₂O requires C, 65.14; H, 8.20; N, 3.16%. |
| 58 | Prep 57 | (S)-methoxy-ethoxy methyl | (4-(2,2-dimethyl-2,3-dihydrobenzofuran-5-yl)butyl) | ¹HNMR (CDCl₃, 400 MHz) δ: 1.42 (s, 6H), 1.47–1.67 (m, 7H), 1.76–1.86 (m, 4H), 2.04 (dd, 1H), 2.55 (t, 2H), 2.59–2.65 (m, 1H), 2.94 (s, 2H), 3.23–3.28 (m, 2H), 3.32 (s, 3H), 3.46–3.50 (m, 3H), 3.55–3.62 (m, 3H), 6.00 (brs, 1H), 6.60 (d, 1H), 6.87 (d, 1H), 6.92 (s, 1H). LRMS: m/z 460 (M − H), ES⁻. Anal. Found C, 56.62; H, 6.93; N, 2.41%. $C_{26}H_{39}NO_6$. 1.2 TFA requires C, 57.00; H, 6.77; N, 2.34%. |
| 59 | Prep 58 | (R)-methyl | (4-(2,2-difluoro-1,3-benzodioxol-5-yl)butyl) | ¹HNMR (CDCl₃, 400 MHz) δ: 1.08 (s, 3H), 1.42–1.76 (m, 7H), 1.80 (t, 2H), 1.88–2.0 (m, 2H), 2.10 (m, 1H), 2.45 (m, 1H), 2.60 (t, 2H), 3.28 (m, 2H), 5.80 (brs, 1H), 6.82–6.92 (m, 2H), 6.95 (dd, 1H). LRMS: m/z 396 (M − H) ES⁻ 398 MH⁺ 420 MNa⁺ ES⁺. Anal. Found C, 55.84; H, 6.20; N, 3.01%. $C_{20}H_{25}F_2NO_5$. 1 H₂O. 0.21 CH₂Cl₂ requires C, 56.03; H, 6.38; N, 3.23%. |

TABLE 1-continued (I)

| Ex | Prec | R¹ | —X—Y | Data |
|---|---|---|---|---|
| 60 | Prep 59 | (S)-methoxy ethyl | [benzofuran-5-yl with CH(Me)CH₂CH₂ linker] | ¹HNMR (CDCl₃, 300 MHz) δ: 1.20 (d, 3H), 1.40–1.85 (m, 12H), 1.95 (m, 2H), 2.45 (m, 1H), 2.65 (m, 1H), 3.05 (m, 1H), 3.15 (t, 2H), 3.25 (s, 3H), 3.30 (m, 3H), 4.50 (t, 2H), 5.60 (brs, 1H), 6.70 (d, 1H), 6.90 (d, 1H), 7.00 (s, 1H). LRMS: m/z 416 (M − H), ES⁻. |
| 61 | Prep 60 | (S)-methoxy ethyl | [6-methylbenzofuran-5-yl with CH₂CH₂CH₂ linker] | ¹HNMR (CDCl₃, 300 MHz) δ: 1.50–1.70 (m, 8H), 1.75 (t, 2H), 1.90–2.10 (m, 4H), 2.21 (s, 3H), 2.50 (m, 1H), 2.60 (t, 2H), 3.25 (s, 3H); 3.30 (m, 2H), 3.35 (m, 2H), 4.50 (m, 2H), 5.80 (brs, 1H), 6.60 (s, 1H), 6.95 (s, 1H). LRMS: m/z 416 (M − H), ES⁻. |
| 62 | Prep 61 | (S)-methoxy ethoxy methyl | [4-chlorophenyl with CH₂CH₂CH₂ linker] | ¹HNMR (CDCl₃, 300 MHz) δ: 1.50 (m, 2H), 1.60–2.00 (m, 10H), 2.60 (m, 3H), 3.20 (t, 2H), 3.30 (s, 3H), 3.45 (m, 3H), 3.55 (m, 2H), 3.60 (m, 1H), 6.0 (brs, 1H), 7.02 (d, 2H), 7.19 (d, 2H). LRMS: m/z 424 (M − H), ES⁻. |
| 63 | Prep 62 | (S)-methoxy ethyl | [6-methylbenzofuran-5-yl with C(Me)₂CH₂CH₂ linker] | ¹HNMR (CDCl₃, 400 MHz) δ: 1.3 (s, 6H), 1.4–1.79 (m, 10H), 1.8 (t, 2H), 1.93 (m, 2H), 2.42 (m, 1H), 3.17 (m, 4H), 3.3 (s, 3H), 3.38 (m, 2H), 4.55 (t, 2H), 5.5 (brs., 1H), 6.7 (d, 1H), 7.1 (d, 1H), 7.2 (s, 1H). LRMS: M − H, 430. (ES⁻) |
| 64 | Prep 63 | (S)-methoxy ethyl | [4-chlorophenyl with CH(CH₂OH)CH₂CH₂ linker] | ¹HNMR (CDCl₃, 300 MHz) δ: 1.40–2.23 (m, 15H), 2.43–2.63 (m, 1H), 2.80–2.95 (m, 1H), 3.29 (s, 3H), 3.03–3.57 (m, 3H), 3.60–3.83 (m, 2H), 5.99 (br.s, 1H), 7.19 (d, 2H), 7.30 (d, 2H). LRMS: M + H, 426. (TS⁺) |
| 65 | Prep 64 | (S)-methoxy ethyl | [4-chlorophenyl with C(Me)(CH₂OH)CH₂CH₂ linker] | ¹HNMR (CDCl₃, 300 MHz) δ: 1.17–2.17 (m, 17H), 2.40–2.58 (m, 1H), 2.98–3.57 (m, 7H), 3.61–3.77 (m, 2H), 5.93 (br.s, 1H), 7.20–7.43 (m, 4H). LRMS: M + H, 440. (TS⁺) |
| 66 | Prep 65 | (S)-methoxy ethyl | [3-chloro-4-methoxyphenyl with CH₂CH₂CH₂ linker] | ¹HNMR (CDCl₃, 300 MHz) δ: 1.40–2.18 (m, 16H), 2.43–2.68 (m, 3H), 3.30 (s, 3H), 3.26–3.48 (m, 2H), 3.88 (s, 3H), 5.83 (brs, 1H), 6.83 (d, 1H), 7.04 (d, 1H), 7.20 (s, 1H). Anal. Found C, 60.01; H, 7.60; N, 3.00%. C₂₂H₃₂ClNO₅. 0.75 H₂O requires C, 60.13; H, 7.68; N, 3.19%. |

TABLE 1-continued

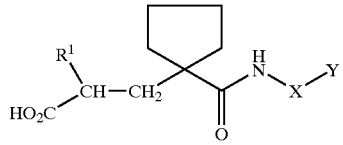

(I)

| Ex | Prec | R[1] | —X—Y | Data |
|---|---|---|---|---|
| 67 | Prep 66 | (S)-methoxy ethyl | | $^1$HNMR (CDCl$_3$, 400 MHz) δ: 1.42 (d, 3H), 1.45–1.66 (8H), 1.74–1.80 (m, 2H), 1.82–1.95 (m, 3H), 1.97–2.02 (1H), 2.42–2.55 (m, 3H), 2.75 (dd, 1H), 3.20–3.27 (m, 6H), 3.31–3.36 (m, 2H), 4.80–4.87 (m, 1H), 5.77 (brs, 1H), 6.61 (d, 1H), 6.85 (d, 1H), 6.93 (s, 1H). LRMS: M + Na, 440. (ES$^+$). |

Alternatively Example 22 may be prepared as follows:

(2S)-2-{[1-({[3-(4-Chlorophenyl)propyl]amino}carbonyl)cyclopentyl]methyl}-4-methoxybutanoic Acid To a solution of the product from Preparation 22 (9.6 g, 21.2 mmol) in dichloromethane (52 ml) was added trifluoroacetic acid (16.3 ml, 212 mmol) and the resultant solution was stirred at room temperature for 3.75 hours under an atmosphere of N$_2$. To the reaction was then added aqueous sodium carbonate solution (95 ml of a 10% w/v solution) with stirring until the pH of the aqueous layer was between pH 2 and 3. The layers were then separated and the organic layer was extracted with aqueous sodium carbonate solution (2×20 ml of a 10% w/v solution). The aqueous layers were combined and saturated brine (80 ml) was then added, followed by 2-butanone (40 ml). The layers were separated and the aqueous layer was extracted again with 2-butanone (2×50 ml). The combined organic layers were then dried by azeotropic distillation at atmospheric pressure to a volume of 70 ml whereupon crystallisation occurred and the mixture was diluted with 2-butanone (70 ml). The product was then collected by filtration and dried at 50° C. for 65 hours under vacuum to give the crude sodium salt of the title compound as a white solid (5.76 g) that was then purified by recrystallisation as follows. To the crude product was added ethyl acetate (87 ml) and ethanol (13 ml) and the remaining insoluble material was removed by filtration. The ethanol was then removed by azeotropic distillation at atmospheric pressure (to remove 110 ml of solvent) and replaced with ethyl acetate (145 ml) whereupon crystallisation occurred. The resultant crystallised product was then collected by filtration under vacuum to give the pure sodium salt of the title product as a white crystalline solid (4.51 g, 10.8 mmol, 51%); m.p. (ethyl acetate) 214–216° C.; $^1$H NMR (DMSO-d$_6$ 300 MHz) δ: 1.26–1.58 (m, 8H), 1.62–1.74 (m, 3H), 1.74–1.86 (m, 1H), 1.91–2.07 (m, 3H), 2.57 (t, 2H), 3.03 (q, 2H), 3.10 (s, 3H), 3.13–3.27 (m, 2H), 7.22 (d, 2H), 7.29 (d, 2H), 9.16 (t, br, 1H); LRMS (ES negative); 789 [2M–H]$^-$ ($^{35}$Cl), 394 [M–H]$^-$ ($^{35}$Cl). For analytical purposes the title product (i.e. the free acid) was obtained by dissolving this sodium salt in water, acidified with 5 M hydrochloric acid and extracted with dichloromethane. Removal of the solvent by blowing a stream of nitrogen over the sample gave the title product; $^1$H NMR (DMSO-d$_6$ 300 MHz) δ: 1.22–1.80 (m, 11H), 1.81–1.96 (m, 2H), 1.96–2.08 (m, 1H), 2.93–2.27 (m, 1H), 2.53 (t, 2H), 3.03 (q, 2H), 3.11 (s, 3H), 3.16–3.25 (m, 2H), 7.20 (d, 2H), 7.30 (d, 2H), 7.51 (t, 1H); LRMS (ES negative); 789 [2M–H]$^-$ ($^{35}$Cl), 394 [M–H]$^-$ ($^{35}$Cl); HPLC (column: ChiralPak AS (25×0.46 cm); mobile phase: hexane/IPA/acetic acid (95/5/0.5 v/v/v); flow rate: 1.0 ml/min; temperature: ambient; injection volume: 20 µl; detection: UV @ 220 nm; Sample concentration: 1.0 mg/ml prepared in mobile phase) Retention Time: minor enantiomer 11.4 min (5.7%), major enantiomer 14.3 min (94.3%).

Sodium Salts of Example 22 a) Mono-Hydrate

To the sodium salt of Example 22 (200 mg) was added to 1 ml of a 3.9% water in isopropanol solution. The resulting slurry was stirred for 12 days whereupon it was isolated by filtration. The product gave the following PXRD pattern.

| Angle 2-Theta° | Intensity % % |
|---|---|
| 3.552 | 30.8 |
| 7.154 | 8 |
| 9.526 | 3.1 |
| 10.359 | 15.7 |
| 10.608 | 14.3 |
| 11.03 | 5 |
| 12.369 | 3.7 |
| 12.939 | 13.2 |
| 13.233 | 12.3 |
| 13.835 | 14.2 |
| 14.345 | 37.9 |
| 14.887 | 16 |
| 15.16 | 16.8 |
| 16.372 | 24.9 |
| 16.813 | 6.9 |
| 17.203 | 22.1 |
| 17.408 | 32.7 |
| 17.708 | 13.5 |
| 17.93 | 29 |
| 18.313 | 12 |
| 18.545 | 23.9 |
| 18.811 | 14 |
| 19.7 | 34.2 |
| 19.978 | 100 |
| 20.273 | 90.6 |
| 20.627 | 51.9 |
| 20.829 | 29.4 |
| 20.926 | 28.4 |
| 21.443 | 52.7 |
| 21.611 | 41.6 |
| 21.881 | 21.2 |

-continued

| Angle 2-Theta° | Intensity % % |
|---|---|
| 22.174 | 24.3 |
| 22.472 | 47.1 |
| 22.881 | 35 |
| 23.141 | 23.2 |
| 23.478 | 15.1 |
| 24.088 | 13.9 |
| 24.313 | 12.6 |
| 24.588 | 22.7 |
| 25.013 | 25.8 |
| 25.514 | 29.9 |
| 25.987 | 25.5 |
| 27.107 | 18.2 |
| 27.395 | 30.6 |
| 27.869 | 19.2 |
| 28.716 | 21 |
| 28.788 | 19 |
| 28.989 | 27.2 |
| 30.232 | 13.4 |
| 30.672 | 15 |
| 30.952 | 17.5 |
| 31.437 | 15.7 |
| 31.788 | 13.9 |
| 32.114 | 24.6 |
| 32.998 | 13.3 |
| 33.375 | 18.8 |
| 33.815 | 14 |
| 34.266 | 14.4 |
| 35.705 | 15.7 |
| 35.989 | 14.1 |
| 36.514 | 16.7 |
| 38.151 | 14.6 |
| 38.925 | 17 |
| 39.091 | 19 |
| 39.961 | 13 |

Differential scanning calorimetry (DSC) was performed using a Perkin Elmer DSC-7 instrument fitted with an automatic sample changer. Approximately 3 mg of the sample was accurately weighed into a 50 microliter aluminium pan and crimp sealed with a perforated lid. The samples were heated at 20° C./minute over the range 40° C. to 300° C. with a nitrogen gas purge. Dehydration events occurred at between 50 and 150° C. and a main melt between 212 and 225° C. The skilled person will appreciate that the melting point may vary outside this range as a result of sample impurity.

b) Anhydrous Salt

The sodium salt of Example 22 gave the following PXRD pattern.

| Angle 2-Theta° | Intensity % % |
|---|---|
| 5.463 | 12.2 |
| 6.654 | 100 |
| 7.546 | 66 |
| 9.336 | 31.3 |
| 10.953 | 9.7 |
| 11.571 | 55.9 |
| 12.56 | 10.9 |
| 13.287 | 22.9 |
| 15.125 | 33.6 |
| 15.667 | 60.3 |
| 16.403 | 17.2 |
| 17.024 | 62.2 |
| 17.714 | 95.6 |
| 18.083 | 31.7 |
| 18.64 | 28.8 |
| 18.902 | 82.4 |

-continued

| Angle 2-Theta° | Intensity % % |
|---|---|
| 19.696 | 40.1 |
| 20.406 | 33.9 |
| 20.502 | 31.8 |
| 20.683 | 45.4 |
| 20.942 | 31.5 |
| 21.559 | 92.6 |
| 21.898 | 66.2 |
| 22.274 | 36.6 |
| 22.735 | 30 |
| 23.36 | 56.5 |
| 24.126 | 31.9 |
| 24.388 | 45.2 |
| 24.72 | 25.8 |
| 25.298 | 26.7 |
| 25.579 | 20.4 |
| 26.718 | 17.6 |
| 27.151 | 24.2 |
| 27.46 | 22.7 |
| 27.737 | 20.2 |
| 28.56 | 27.1 |
| 28.926 | 23.8 |
| 29.802 | 23.5 |
| 30.454 | 30.7 |
| 30.885 | 29.2 |
| 31.48 | 21 |
| 32.66 | 16.8 |
| 34.027 | 23.1 |
| 34.494 | 17.6 |
| 36.011 | 19 |
| 36.997 | 17.4 |
| 38.704 | 21.2 |
| 39.961 | 18.7 |

PREPARATIONS

Preparation 1 tert-Butyl 4-methoxy-2-{[1-({[3-(4-methoxyphenyl)propyl]amino}carbonyl)-cyclopentyl]methyl}butanoate

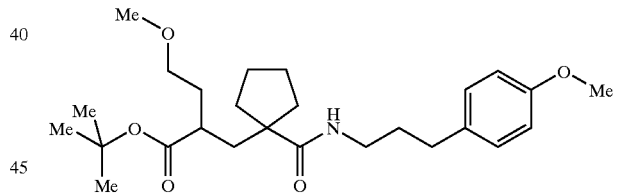

The product from Preparation 68 (325 mg, 1.08 mmol), the product of Preparation 73 (178 mg, 1.08 mmol), HOBt (146 mg, 1.08 mmol), WSCDI (207 mg, 1.08 mmol) and triethylamine (0.3 ml, 2.16 mmol) were stirred together in dichloromethane (5 ml) at room temperature for 14 hours. The reaction mixture was diluted with dichloromethane (10 ml) and washed with water (2×20 ml). The organic layer was dried over magnesium sulphate, filtered and concentrated in vacuo. The product was purified by column chromatography using dichloromethane, then 99:1 dichloromethane:methanol, then 98:2 dichloromethane:methanol ($R_f$ 0.2) to give the product as a yellow oil (267 mg, 0.6 mmol); $^1$H NMR (CDCl$_3$ 400 MHz) δ: 1.4 (s, 9H), 1.6 (m, 5H), 1.8 (m, 4H), 2.0 (m, 1H), 2.3 (m, 1H), 2.6 (t, 2H), 3.2 (s, 3H), 3.3 (m, 2H), 3.7 (s, 3H), 5.7 (t, 1H), 6.8 (d, 2H), 7.0 (d, 2H); LRMS: m/z 448 (M−H$^+$).

The following Examples of formula (IVa), i.e. compounds of general formula IV where prot is tert-butyl, were prepared by methods similar to Preparation 1, from the precursors indicated (see Table 2).

TABLE 2

(IVa)

| Prep | Prec. acid | Prec. amine | R¹ | –X–Y | Analytical Data |
|---|---|---|---|---|---|
| 2 | Prep 68 | Commercially available from ICN Biomedicals Inc | methoxyethyl |  | ¹H NMR (CDCl₃, 400 MHz) δ: 1.4 (s, 9H), 1.6–2.0 (m, 16H), 2.3 (m, 1H), 2.6 (t, 2H), 3.2 (d, 3H), 3.3 (m, 3H), 3.7 (s, 3H), 4.0 (m, 1H), 5.5 (bs, 1H), 6.8 (d, 2H), 7.1 (d, 2H). LRMS: m/z 462 (M − H⁺). |
| 3 | Prep 68 | Prep 120 | methoxyethyl |  | ¹H NMR (CDCl₃, 400 MHz) δ: 1.4–1.45 (m, 10H), 1.5–1.7 (m, 6H), 1.7–1.8 (m, 2H), 1.9–2.1 (m, 4H), 2.3–2.4 (m, 1H), 3.1 (d, 3H), 3.1–3.35 (m, 3H), 3.9–4.0 (m, 2H), 4.3–4.4 (m, 1H), 6.1–6.2 (m, 1H), 6.8–6.9 (s, 2H), 7.2 (t, 1H), 7.3 (d, 1H). |
| 4 | Prep 68 | U.S. 4533655, Example 7A | methoxyethyl |  | ¹H NMR (CDCl₃, 400 MHz) δ: 1.4 (s, 9H), 1.5 (m, 2H), 1.6 (m, 4H), 1.7 (dd, 3H), 1.8 (m, 2H), 1.9 (m, 3H), 2.3 (m, 1H), 2.6 (t, 2H), 3.1 (m, 1H), 3.2 (s, 3H), 3.3 (t, 2H), 5.9 (m, 1H), 6.9 (t, 2H), 7.1 (t, 2H). LRMS: m/z 436 (M − H⁺). |
| 5 | Prep 68 | Commercially available from Aldrich Chemical Company | methoxyethyl |  | ¹H NMR (CDCl₃, 400 MHz) δ: 1.4 (s, 9H), 1.5–1.6 (m, 10H), 1.7 (m, 2H), 2.0 (m, 4H), 2.3 (m, 1H), 2.6 (t, 2H), 3.2 (s, 5H), 3.3 (t, 2H), 5.9 (bs, 1H), 7.1 (m, 3H), 7.2 (t, 2H), 10.4 (bs, 1H). LRMS: m/z 432 (M − H⁺). |
| 6 | Prep 68 | Commercially available from Aldrich Chemical Company | methoxyethyl |  | ¹H NMR (CDCl₃, 400 MHz) δ: 1.4 (s, 9H), 1.45 (m, 2H), 1.6 (m, 8H), 1.8 (m, 4H), 2.3 (m, 1H), 2.6 (t, 2H), 3.2 (s, 3H), 3.3 (m, 4H), 3.8 (bs, 1H), 7.1 (d, 3H), 7.2 (d, 2H). LRMS: m/z 418 (M − H⁺). |
| 7 | Prep 68 | Bioorg. Med. Chem., 1997, 5, 1675–83 | methoxyethyl | | ¹H NMR (CDCl₃, 400 MHz) δ: 1.4 (s, 10H), 1.6 (m, 10H), 1.8 (m, 2H), 2.3 (m, 1H), 2.6 (t, 2H), 3.2 (s, 3H), 3.3 (m, 4H), 5.7 (bs, 1H), 6.7 (d, 2H), 7.0 (d, 2H). LRMS: m/z 434 (M − H⁺). |

TABLE 2-continued (IVa)

Structure: cyclopentane core with R¹ substituent, connected via C(=O)O-C(Me)₂-Me ester and C(=O)NH-X-Y amide.

| Prep | Prec. acid | Prec. amine | R¹ | –X–Y | Analytical Data |
|---|---|---|---|---|---|
| 8 | Prep 68 | Bioorg. Med. Chem., 1997, 5, 1675–83 | methoxyethyl | 4-(trifluoromethyl)phenyl-propyl | ¹H NMR (CDCl₃, 400 MHz) δ: 1.5 (s, 9H), 1.5–2.4 (m, 15H), 2.7 (m, 2H), 3.25 (s, 2H), 3.3 (m, 4H), 5.9 (s, 1H), 7.3 (m, 2H), 7.3 (m, 2H). LRMS: m/z 486 (M – H⁺). |
| 9 | Prep 68 | Prep 74 | methoxyethyl | 4-ethylphenyl-propyl | ¹H NMR (CDCl₃, 400 MHz) δ: 1.2 (t, 3H), 1.4 (s, 11H), 1.6 (m, 9H), 1.8 (m, 3H), 1.9 (m, 2H), 2.3 (q, 1H), 2.6 (q, 4H), 3.2 (s, 3H), 3.3 (m, 2H), 3.35 (t, 2H), 5.8 (bs, 1H), 7.1 (s, 4H). LRMS: m/z 446 (M – H⁺). |
| 10 | Prep 68 | Prep 75 | methoxyethyl | 4-methoxy-3-methylphenyl-propyl | ¹H NMR (CDCl₃, 400 MHz) δ: 1.4 (s, 9H), 1.45 (m, 2H), 1.5–2.03 (m, 12H), 2.28 (s, 3H), 2.38 (m, 1H), 2.59 (t, 2H), 3.25 (s, 3H), 3.33 (m, 4H), 3.78 (s, 3H), 5.79 (s, 1H), 6.7 (m, 2H), 7.03 (d, 1H). LRMS: m/z 462 (M + H⁺). |
| 11 | Prep 68 | Prep 76 | methoxyethyl | 2,3-dihydrobenzofuran-5-yl-propyl | ¹H NMR (CDCl₃, 400 MHz) δ: 1.40 (s, 9H), 1.6 (m, 10H), 1.8 (m, 3H), 1.9 (m, 2H), 2.3 (m, 1H), 2.6 (t, 2H), 3.1 (t, 2H), 3.2 (s, 3H), 3.3 (q, 2H), 4.5 (t, 2H), 5.7 (m, 1H), 6.9 (d, 1H), 7.0 (s, 1H). LRMS: m/z 460 (M – H⁺). |
| 12 | Prep 68 | Commercially available from Xenobiotica | methoxyethyl | 2-hydroxyphenyl-propyl | ¹H NMR (CDCl₃, 400 MHz) δ: 1.4 (s, 10H), 1.5–1.7 (m, 6H), 1.7–1.85 (m, 4H), 1.9–2.0 (m, 3H), 2.3–2.4 (m, 1H), 2.6–2.7 (m, 2H), 3.2 (d, 2H), 3.3 (s, 3H), 3.3–3.4 (m, 2H), 6.3 (bs, 1H), 6.9 (t, 2H), 7.0.5 (dd, 2H). LRMS: m/z 434 (M + H⁺). |
| 13 | Prep 68 | J. Med. Chem., 1996, 39(20), 4017 | methoxyethyl | 3-chlorophenyl-propyl | ¹H NMR (CDCl₃, 400 MHz) δ: 1.4 (s, 10H), 1.5–2.0 (m, 14H), 2.3–2.4 (m, 1H), 2.6 (t, 2H), 3.2 (s, 3H), 3.2–3.3 (m, 3H), 3.4–3.5 (m, 2H), 5.8 (bs, 1H), 7.0 (d, 1H), 7.1–7.2 (m, 3H). LRMS: m/z 452 (M + H⁺). |
| 14 | Prep 68 | Tet. Lett., 1999, 40, 2033–4 | methoxyethyl | 2-chlorophenyl-propyl | ¹H NMR (CDCl₃, 400 MHz) δ: 1.4–1.45 (m, 10H), 1.5–2.0 (m, 13H), 2.3–2.4 (m, 1H), 2.7 (t, 2H), 3.2 (s, 3H), 3.25–3.35 (m, 4H), 5.8 (bs, 1H), 7.05–7.3 (m, 4H). LRMS: m/z 452 (M + H⁺). |

TABLE 2-continued (IVa)

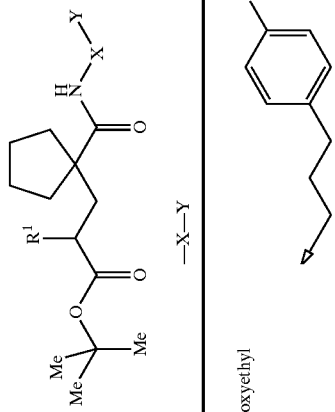

| Prep | Prec. acid | Prec. amine | R¹ | —X—Y | Analytical Data |
|---|---|---|---|---|---|
| 15 | Prep 68 | J. Med. Chem., 1996, 39, 4942–51 | methoxyethyl | 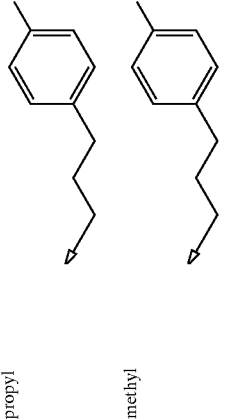 | ¹H NMR (CDCl₃, 400 MHz) δ: 1.4 (s, 10H), 1.5–2.05 (m, 13H), 2.3–2.4 (m, 1H), 2.6 (t, 2H), 3.25 (s, 3H), 3.20–3.35 (m, 4H), 5.8 (bs, 1H), 7.1 (d, 2H), 7.2 (d, 2H). LRMS: m/z 452 (M + H⁺). |
| 16 | Prep 71 | Prep 73 | (R)-propyl | 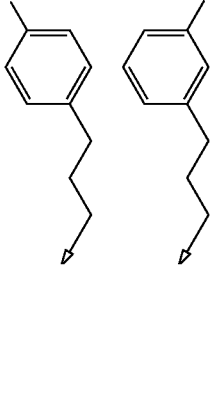 | ¹H NMR (CDCl₃, 400 MHz) δ: 0.8 (t, 3H), 1.2 (m, 6H), 1.4 (s, 9H), 1.4–1.9 (m, 10H), 2.2 (m, 1H), 2.5 (t, 2H), 3.2 (m, 2H), 3.7 (s, 3H), 5.6 (s, 1H), 6.8 (d, 2H), 7.1 (d, 2H). LRMS: m/z 432 (M − H⁻). |
| 17 | Prep 70 | Prep 73 | (R)-methyl | 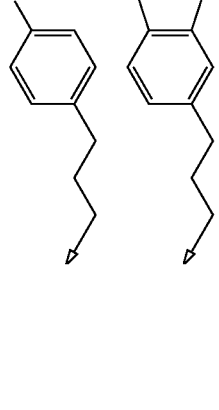 | ¹H NMR (CDCl₃, 400 MHz) δ: 1.11 (t, 3H), 1.38–2.10 (m, 21H), 2.03 (m, 2H), 2.33 (m, 1H), 2.62 (t, 2H), 3.28 (m, 2H), 3.80 (s, 3H), 5.73 (m, 1H), 6.83 (d, 2H), 7.12 (d, 2H). |
| 18 | EP274234B1, Example 35 | Prep 73 | H |  | ¹H NMR (CDCl₃, 400 MHz) δ: 1.43 (m, 9H), 1.48 (m, 2H), 1.65 (m, 4H), 1.83 (m, 4H), 1.99 (m, 2H), 2.19 (m, 2H), 2.61 (t, 2H), 3.29 (q, 2H), 3.8 (s, 3H), 5.59 (m, 1H), 6.84 (d, 2H), 7.11 (d, 2H). |
| 19 | EP274234B1, Example 35 | J. Med. Chem., 1996, 39(20), 4017 | H |  | ¹H NMR (CDCl₃, 400 MHz) δ: 1.36–1.50 (m, 11H), 1.62 (m, 4H), 1.80 (m, 4H), 1.94 (m, 2H), 2.13 (m, 2H), 2.59 (t, 2H), 3.25 (q, 2H), 5.61 (m, 1H), 7.03 (d, 1H), 7.15 (m, 3H). |
| 20 | EP274234B1, Example 35 | J. Med. Chem., 1996, 39, 4942–51 | H | | ¹H NMR (CDCl₃, 400 MHz) δ: 1.61–1.78 (m, 11H), 1.66 (m, 4H), 1.85 (m, 4H), 2.00 (m, 2H), 2.20 (m, 2H), 2.63 (t, 2H), 3.29 (q, 2H), 5.64 (m, 1H), 7.13 (d, 2H), 7.26 (d, 2H). |
| 21 | EP274234B1, Example 35 | Prep 76 | H | | ¹H NMR (CDCl₃, 400 MHz) δ: 1.35–1.45 (m, 11H), 1.61 (m, 4H), 1.78 (m, 4H), 1.92 (m, 2H), 2.14 (t, 2H), 2.53 (t, 2H), 3.14 (t, 2H), 3.24 (q, 2H), 4.50 (t, 2H), 5.53 (m, 1H), 6.66 (d, 1H), 6.84 (d, 1H), 6.98 (s, 1H). |

TABLE 2-continued (IVa)

| Prep | Prec. acid | Prec. amine | R¹ | –X–Y | Analytical Data |
|---|---|---|---|---|---|
| 22 | Prep 69 | J. Med. Chem., 1996, 39, 4942–51 | (S)-methoxyethyl | 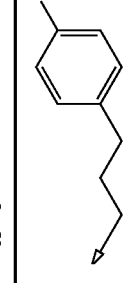 | ¹H NMR (CDCl₃, 400 MHz) δ: 1.4 (s, 10H), 1.5–2.05 (m, 13H), 2.3–2.4 (m, 1H), 2.6 (t, 2H), 3.25 (s, 3H), 3.20–3.35 (m, 4H), 5.8 (bs, 1H), 7.1 (d, 2H), 7.2 (d, 2H). LRMS: m/z 452 (M – H⁻). [α]$_D$ + 0.0 (MeOH, c 0.35). Anal. Found C, 65.95; H, 8.66; N, 3.25. C$_{25}$H$_{38}$NO$_4$Cl 0.18 H$_2$O requires C, 65.95; H, 8.49; N, 3.08% |
| 23 | Prep 69 | U.S. 4533655, Example 7A | (S)-methoxyethyl | 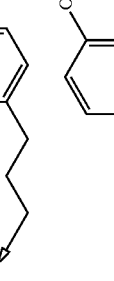 | ¹H NMR (CDCl₃, 400 MHz) δ: 1.4 (s, 9H), 1.5–2.0 (m, 14H), 2.2 (m, 1H), 2.5 (m, 2H), 3.2 (s, 3H), 3.2–3.3 (m, 4H), 5.8 (bs, 1H), 6.9 (m, 2H), 7.1 (m, 2H). LRMS: m/z 436 (M – H⁺). |
| 24 | Prep 69 | Prep 73 | (S)-methoxyethyl | 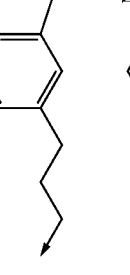 | ¹H NMR (CDCl₃, 400 MHz) δ: 1.4 (s, 9H), 1.5–2.0 (m, 15H), 2.3 (m, 1H), 2.6 (t, 2H), 3.2 (s, 3H), 3.2–3.3 (m, 3H), 3.3 (t, 2H), 3.7 (s, 3H), 5.7 (bs, 1H), 6.8 (d, 1H), 7.0 (d, 2H). LRMS: m/z 448 (M – H⁺). HRMS m/z 448.3048 (C$_{26}$H$_{41}$NO$_5$ requires 448.3058) |
| 25 | Prep 69 | Prep 76 | (S)-methoxyethyl | 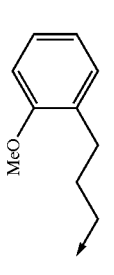 | ¹H NMR (CDCl₃, 400 MHz) δ: 1.40 (s, 9H), 1.50–2.03 (m, 16H), 2.30–2.39 (m, 1H), 2.57 (t, 2H), 3.16 (t, 2H), 3.24 (s, 3H), 3.32 (t, 2H), 4.55 (t, 2H), 5.78 (bs, 1H), 6.68 (d, 1H), 6.90 (d, 1H), 7.0 (s, 1H). LRMS: m/z 460 (M – H⁻). HRMS m/z 460.3064 (C$_{27}$H$_{42}$NO$_5$ requires 460.3057). |
| 26 | EP272234B1, Example 35 | Prep 99 | H |  | ¹HNMR (CDCl₃, 400 MHz) δ: 1.41 (s, 9H), 1.23–1.78 (m, 5H), 1.80–2.03 (m, 4H), 2.07–2.28 (m, 4H), 2.83 (dt, 2H), 3.00 (brs, 2H), 3.33 (q, 1H), 5.63 (brs, 1H), 7.37 (dd, 1H), 7.52–7.60 (m, 2H), 8.03 (dd, 2H), 8.84 (d, 1H). LRMS: ES⁺ m/z 411 (M + H). |
| 27 | Prep 68 | | methoxyethyl |  | ¹HNMR (CDCl₃, 400 MHz) δ: 1.40 (s, 10H), 1.60 (m, 6H), 1.80 (m, 2H), 2.01 (m, 4H), 2.45 (m, 1H), 2.6 (t, 2H), 3.21 (m, 2H), 3.25 (s, 3H), 3.30 (s, 3H), 3.41 (m, 2H), 5.86 (brs, 1H), 6.90 (brm, 2H), 7.10 (m, 2H). LRMS: ES⁺ m/z 448.8 (M + H) |

TABLE 2-continued (IVa)

| Prep | Prec. acid | Prec. amine | R¹ | —X—Y | Analytical Data |
|---|---|---|---|---|---|
| 28 | Prep 68 | Prep 83 | methoxyethyl | 4-methylphenyl-butyl | ¹HNMR (CDCl₃, 400 MHz) δ: 1.40 (s, 9H), 1.60 (m, 4H), 1.80 (m, 4H), 2.10 (m, 4H), 2.31 (s, 3H), 2.42 (m, 1H), 2.60 (t, 2H), 3.21 (s, 3H), 3.40 (m, 4H), 5.81 (brs, 1H), 7.10 (s, 4H). |
| 29 | Prep 68 | Prep 84 | methoxyethyl | 3-benzyloxyphenyl-butyl | ¹HNMR (CDCl₃, 400 MHz) δ: 1.61 (m, 10H), 1.90 (m, 4H), 2.01 (m, 2H), 2.53 (m, 1H), 2.60 (t, 3H), 3.20 (m, 5H), 3.30 (q, 2H), 5.01 (s, 2H), 5.80 (brs, 1H), 6.90 (m, 3H), 7.21 (t, 1H), 7.40 (m, 5H). LRMS: ES⁺ m/z 468 (M + H). |
| 30 | Prep 68 | Prep 85 | methoxyethyl | 3-methoxyphenyl-butyl | ¹HNMR (CDCl₃, 400 MHz) δ: 1.40 (m, 10H), 1.60 (m, 6H), 1.80 (m, 4H), 2.01 (m, 2H), 2.30 (m, 2H), 2.59 (t, 2H), 3.21 (s, 3H), 3.30 (m, 2H), 3.80 (d, 3H), 5.91 (brs, 1H), 6.21–6.39 (dd, 1H), 6.72 (dd, 1H), 6.90 (d, 1H), 7.11 (q, 1H). LRMS: ES⁺ m/z 448 (M + H). |
| 31 | Prep 68 | Prep 86 | methoxyethyl | 3,4-dimethoxyphenyl-butyl | ¹HNMR (CDCl₃, 400 MHz) δ: 1.39 (s, 10H), 1.55–1.61 (m, 4H), 1.63–1.81 (m, 6H), 1.95 (m, 2H), 2.05 (dd, 2H), 2.55 (t, 2H), 3.20 (q, 2H), 3.22 (s, 3H), 3.30 (t, 2H), 3.78 (d, 6H), 5.88 (brt, 1H), 6.40 (m, 2H), 6.95 (d, 1H). LRMS: ES⁺ m/z 478 (M + H). |
| 32 | Prep 69 | Prep 107 | (S)-methoxyethyl | 4-methoxyphenyl-butyl | ¹HNMR (CDCl₃, 300 MHz) δ: 1.39–2.08 (25H, m), 2.34 (1H, m), 2.57 (2H, t), 3.20–3.28 (5H, m), 3.33 (2H, t), 3.78 (3H, s), 5.74 (1H, m), 6.81 (2H, d), 7.07 (2H, d). |
| 33 | EP274234B1, Example 35 | Prep 79 | H | naphthyl-butyl | ¹HNMR (CDCl₃, 400 MHz) δ: 1.20 (s, 9H), 1.60 (m, 4H), 1.75 (m, 2H), 1.80–2.00 (m, 6H), 2.10 (m, 2H), 3.05 (t, 2H), 3.30 (m, 2H), 5.60 (brs, 1H), 7.25 (m, 1H), 7.35 (m, 1H), 7.45 (m, 2H), 7.65 (d, 1H), 7.80 (d, 1H), 7.95 (d, 1H). LRMS: ES⁺ m/z 410.2 (M + H). |

TABLE 2-continued (IVa)

[Structure: cyclopentane with -C(=O)NH-X-Y substituent and -CH(R¹)-C(=O)-O-C(Me)₂-Me ester group]

| Prep | Prec. acid | Prec. amine | R¹ | —X—Y | Analytical Data |
|---|---|---|---|---|---|
| 34 | EP274234B1, Example 35 | Prep 78 | H | 2-naphthyl-(CH₂)₄- | ¹HNMR (CDCl₃, 400 MHz) δ: 1.40 (s, 9H), 4.42 (m, 2H), 1.60 m, 4H), 1.80 (m, 3H), 1.90 (m, 4H), 2.10 (m, 2H), 2.80 (t, 2H), 3.30 ,(q, 2H), 5.60 (brs, 1H), 7.30 (d, 1H), 7.40 (m, 2H), 7.60 (s, 1h), 7.75 (m, 3H). LRMS: ES⁺ m/z 410.2 (M + H). |
| 35 | Prep 69 | Prep 95 | (S)-methoxyethyl | 4-F,3-Cl-phenyl-(CH₂)₄- | ¹HNMR (CDCl₃, 400 MHz) δ: 1.4 (s, 9H), 1.55≈1.81 (m, 11H), 1.8–2.0 (m, 3H), 2.35 (m, 1H), 2.55 (t, 2H), 3.21 (s, 3H), 3.22 (t, 2H), 3.30 (t, 2H), 5.82 (brs, 1H), 7.0 (dd, 2H), 7.18 (d, 1H). LRMS: ES⁺ m/z 471 (M + H). |
| 36 | Prep 69 | Prep 94 | (S)-methoxyethyl | 3-Cl,4-F-phenyl-(CH₂)₄- | ¹HNMR (CDCl₃, 400 MHz) δ: 1.41 (s, 9H), 1.55–2.06 (m, 13H), 2.15–2.21 (m, 1H), 2.32–2.38 (m, 1H), 3.22 (s, 3H), 3.25–3.35 (m, 4H), 5.81 (brs, 1H), 6.90 (d, 1H), 6.95 (d, 1H), 7.22–7.24 (m, 1H). LRMS: TSP⁺ m/z 470 (M + H). |
| 37 | Prep 69 | Prep 77 | (S)-methoxyethyl | 2,4-diF-phenyl-(CH₂)₄- | ¹HNMR (CDCl₃, 400 MHz) δ: 1.4 (s, 9H), 1.55–1.80 (m, 11H), 1.85–2.05 (m, 3H), 2.36 (m, 1H), 2.60 (t, 2H), 3.21 (s, 3H), 3.25 (t, 2H), 3.30 (t, 2H), 5.85 (brs, 1H), 6.75 (q, 2H), 7.10 (q, 1H). LRMS: ES⁺ m/z 454 (M + H). |
| 38 | EP274234B1, Example 35 | Prep 97 | H | 2,6-diF-phenyl-(CH₂)₄- | ¹HNMR (CDCl₃, 300 MHz) δ: 1.41 (s, 9H), 1.50 (m, 2H), 1.67 (m, 4H), 1.75–1.90 (m, 4H), 2.0 (m, 2H), 2.20 (t, 2H), 2.72 (t, 2H), 3.28 (q, 2H), 5.80 (brs, 1H), 6.85 (t, 2H), 7.16 (m, 1H). LRMS: ES⁺ m/z 396 (M + H). |
| 39 | EP274234B1, Example 35 | Prep 96 | H | 2,3-diF-phenyl-(CH₂)₄- | ¹HNMR (CDCl₃, 300 MHz) δ: 1.42 (s, 9H), 1.50 (m, 2H), 1.67 (m, 4H), 1.78–1.90 (m, 4H), 2.0 (m, 2H), 2.20 (t, 2H), 2.70 (t, 2H), 3.30 (q, 2H), 5.85 (brs, 1H), 6.92–7.05 (m, 3H). LRMS: ES⁺ m/z 396 (M + H). |

TABLE 2-continued (IVa)

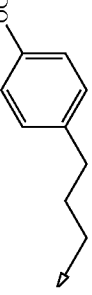

| Prep | Prec. acid | Prec. amine | R¹ | —X—Y | Analytical Data |
|---|---|---|---|---|---|
| 40 | EP274234B1, Example 35 | Prep 98 | H | 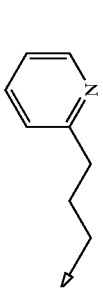 | ¹HNMR (CDCl₃, 300 MHz) δ: 1.41 (s, 9H), 1.48 (m, 2H), 1.53 (m, 4H), 1.75–1.90 (m, 4H), 2.0 (m, 2H), 2.18 (t, 2H), 2.63 (t, 2H), 3.28 (q, 2H), 5.71 (brs, 1H), 7.10 (dd, 2H), 7.20 (dd, 2H). LRMS: ES⁺ m/z 444 (M + H). |
| 41 | Prep 69 | Prep 108 | (S)-methoxyethyl | 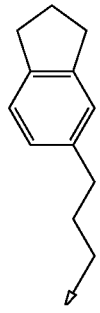 | ¹HNMR (CDCl₃, 300 MHz) δ: 1.38–2.10 (23H, m), 2.38 (1H, m), 2.88 (2H, t), 3.27–3.38 (7H, m), 6.45 (1H, s), 7.10–7.22 (2H, m), 7.61 (1H, m), 8.54 (1H, d). |
| 42 | EP274234B1, Example 35 | Prep 117 | H | 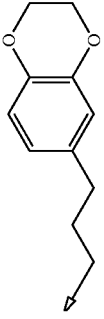 | ¹HNMR (CDCl₃, 400 MHz) δ: 1.41 (s, 9H), 1.58 (bs, 4H), 1.72–1.82 (m, 4H), 1.86–1.92 (m, 2H), 1.96–2.05 (m, 2H), 2.10 (t, 2H), 2.54 (t, 2H), 2.83 (brs, 4H), 3.20–3.30 (m, 2H), 5.52 (brs, 1H), 6.90 (d, 1H), 7.00 (s, 1H), 7.07 (d, 1H). LRMS: TSP⁺ m/z 400 (M + H). |
| 43 | Prep 69 | Prep 81 | (S)-methoxyethyl |  | ¹HNMR (CDCl₃, 300 MHz) δ: 1.39–2.08 (23H, m), 2.38 (1H, m), 2.58 (2H, t), 3.23–3.39 (7H, m), 4.23 (3H, s), 5.78 (1H, m), 6.63–6.72 (2H, m), 6.79 (1H, d). |
| 44 | Prep 69 | Prep 80 | (S)-methoxyethyl | 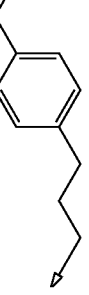 | ¹HNMR (CDCl₃, 300 MHz) δ: 1.38–2.10 (23H, m), 2.39 (1H, m), 2.73 (2H, t), 3.06–3.41 (7H, m), 5.83 (1H, m), 7.19–7.35 (3H, m), 7.69–7.78 (2H, m), 7.94 (2H, d), 8.68 (1H, d). |
| 45 | EP274234B1, Example 35 | Prep 119 | H |  | ¹HNMR (CDCl₃, 400 MHz) δ: 1.40 (s, 9H), 1.42–1.44 (m, 2H), 1.58–1.63 (m, 4H), 1.72–1.81 (m, 4H), 1.95–1.98 (m, 2H), 2.15 (t, 2H), 2.55 (t, 2H), 3.20–3.26 (m, 2H), 5.57 (brs, 1H), 7.02 (d, 2H), 7.35 (d, 2H). LRMS: ES⁺ m/z 461 (M + Na). |

TABLE 2-continued (IVa)

[Structure: cyclopentane with -C(=O)NH-X-Y group and -CH(R¹)-C(=O)-O-C(Me)₂-Me group]

| Prep | Prec. acid | Prec. amine | R¹ | —X—Y | Analytical Data |
|---|---|---|---|---|---|
| 46 | EP274234B1, Example 35 | Prep 113 | H | [4-(1-methyl-1H-indazol-5-yl)butyl] | ¹HNMR (CDCl₃, 400 MHz) δ: 1.39–1.52 (11H, m), 1.63 (4H, m), 1.79–2.01 (6H, m), 2.18 (2H, t), 2.78 (2H, t), 3.32 (2H, q), 4.06 (3H, s), 5.61 (1H, m), 7.23 (1H, d), 7.33 (1H, d), 7.52 (1H, s), 7.90 (1H, s). |
| 47 | EP274234B1, Example 35 | Prep 90 | H | [4-(2-methyl-2H-indazol-5-yl)butyl] | ¹HNMR (CDCl₃, 400 MHz) δ: 1.35-1.50 (m, 11H), 1.62 (m, 4H), 1.72–2.02 (m, 6H), 2.18 (t, 2H), 2.72 (t, 2H), 3.31 (q, 2H), 4.21 (s, 3H), 5.60 (m, 1H), 7.12 (d, 1H), 7.41 (s, 1H), 7.63 (d, 1H), 7.80 (s, 1H). |
| 48 | EP274234B1, Example 35 | Prep 88 | H | [4-(chroman-6-yl)butyl] | ¹HNMR (CDCl₃, 400 MHz) δ: 0.83 (t, 2H), 1.40 (s, 9H), 1.18–1.49 (m, 4H), 1.70–1.84 (m, 4H), 1.85–2.01 (m, 4H), 2.03–2.18 (m, 2H), 2.50 (t, 2H), 2.72 (t, 2H), 3.22 (q, 2H), 4.11 (t, 2H), 5.60 (brs., 1H), 6.65 (d, 1H), 6.80 (s, 1H), 6.84 (d, 1H). LRMS: M + H, 416 (ES⁺). |
| 49 | EP274234B1, Example 35 | Prep 100 | H | [4-(4-methylthiophenyl)butyl] | ¹HNMR (CDCl₃, 400 MHz) δ: 1.39 (s, 9H), 1.40–1.45 (m, 2H), 1.58–1.63 (m, 4H), 1.76–1.80 (m, 4H), 1.89–1.95 (m, 2H), 2.05–2.12 (m, 2H), 2.44 (s, 3H), 2.66 (t, 2H), 3.25 (dt, 2H), 5.56 (brs, 1H), 7.07 (d, 2H), 7.15 (d, 2H). LRMS: M + Na, 428 (ES⁺). |
| 50 | EP274234B1, Example 35 | Prep 133 | H | [4-(2,3-dihydrobenzofuran-5-yl)pentyl with Me branch] | ¹HNMR (CDCl₃, 400 MHz) δ: 1.20 (d, 3H), 1.40 (s, 9H), 1.50–1.80 (m, 12H), 2.10 (m, 2H), 2.60 (m, 1H), 3.05 (m, 1H), 3.1 (t, 2H), 3.20 (m, 1H), 4.50 (t, 2H), 5.40 brs, 1H), 6.65 (d, 1H), 6.90 (d, 1H), 7.0 (s, 1H). LRMS: M + H, 415.8 (TS⁺). |
| 51 | EP274234B1, Example 35 | Prep 141 | H | [4-(2,3-dihydrobenzofuran-5-yl)pentyl, Me branch] | ¹HNMR (CDCl₃, 400 MHz) δ: 1.10 (d, 3H), 1.40 (s, 9H), 1.45 (m, 2H), 1.60 (m, 4H), 1.65 (m, 2H), 1.80 (m, 2H), 1.90 (m, 2H), 2.10 (m, 2H), 2.50 (t, 2H), 3.10 (t, 2H), 4.00 (m, 1H), 4.50 (t, 2H), 5.40 (d, 1H), 6.60 (d, 1H), 6.85 (d, 1H), 6.95 (s, 1H). LRMS: M + H, 415.8 (TS⁺). |

TABLE 2-continued (IVa)

| Prep | Prec. acid | Prec. amine | R¹ | —X—Y | Analytical Data |
|---|---|---|---|---|---|
| 52 | Prep 69 | Prep 100 | (S)-methoxy ethyl | 4-SMe-phenyl-butyl | ¹HNMR (CDCl₃, 400 MHz) δ: 1.40 (s, 9H), 1.41–1.43 (m, 2H), 1.56–2.00 (m, 12H), 2.26–2.36 (m, 1H), 2.42 (s, 3H), 2.58 (t, 2H), 3.21–3.28 (m, 5H), 3.30 (t, 2H), 5.73 (brs, 1H), 7.07 (d, 2H), 7.15 (d, 2H). LRMS: M + Na, 486 (ES⁺). |
| 53 | EP274234B1, Example 35 | Prep 131 | H | isobenzofuran-butyl | ¹HNMR (CDCl₃, 400 MHz) δ: 1.42 (s, 9H), 1.44–1.55 (m, 2H), 1.58–1.70 (m, 3H), 1.75–1.88 (m, 4H), 1.90–2.01 (m, 4H), 2.18 (t, 2H), 3.35 (m, 2H), 4.27 (t, 1H), 4.62 (t, 1H), 5.72 (brs, 1H), 6.79 (dd, 1H), 6.88 (t, 1H), 7.12 (t, 1H), 7.18 (dd, 1H). LRMS: MNa⁺, 410 (ES⁺). |
| 54 | Prep 69 | Prep 100 | (S)-methoxy ethyl | dihydrobenzofuran-butyl | ¹HNMR (CDCl₃, 400 MHz) δ: 1.40 (s, 9H), 1.42–1.48 (m, 2H), 1.54–1.80 (m, 9H), 1.88–2.03 (m, 4H), 2.29–2.35 (m, 1H), 2.57–2.60 (m, 2H), 3.15–3.21 (m, 4H), 3.23 (s, 3H), 3.30 (t, 2H), 4.53 (t, 2H), 6.11 (brs, 1H), 6.75 (dd, 1H), 6.90 (d, 1H), 7.01 (d, 1H). LRMS: M + Na, 482 (ES⁺). |
| 55 | Prep 69 | Prep 90a | (S)-methoxy ethyl | 7-Me-dihydrobenzofuran-butyl | ¹HNMR (CDCl³, 400 MHz) δ: 1.40 (s, 9H), 1.50–2.00 (m, 14H), 2.10 (s, 3H), 2.30 (m, 1H), 2.50 (t, 2H), 3.10 (t, 2H), 3.20 (s, 3H), 3.30 (m, 4H), 4.50 (t, 2H), 5.70 (brs., 1H), 6.70 (s, 1H), 6.80 (s, 1H). LRMS: M + H, 474.6 (TS⁺). |
| 56 | EP0342850, see also Tet. Letts., 1999, 40, 2187 | Prep 76 | (S)-methoxy ethoxy methyl | dihydrobenzofuran-butyl | ¹HNMR (CDCl₃, 400 MHz) δ: 1.41 (s, 9H), 1.57–2.03 (m, 16H), 2.58 (t, 3H), 3.32 (s, 3H), 3.11–3.57 (m, 8H), 4.53 (t, 2H), 5.98 (brs., 1H), 6.68 (d, 1H), 6.90 (d, 1H), 7.01 (s, 1H), LRMS: M + H, 490 (ES⁺). |

TABLE 2-continued (IVa)

[Structure: R¹ substituted cyclopentane with ester group (OC(Me)₂Me) and amide (NH-X-Y)]

| Prep | Prec. acid | Prec. amine | R¹ | —X—Y | Analytical Data |
|---|---|---|---|---|---|
| 57 | EP0342850, see also Tet. Letts., 1999, 40, 2187 | Prep 87 | (S)-methoxy-ethoxy methyl | 2,2-dimethyl-benzodioxole with propyl chain | ¹HNMR (CDCl₃, 400 MHz) δ: 1.36 (s, 9H), 1.40 (s, 6H), 1.56–1.62 (m, 4H), 1.67–1.79 (m, 3H), 1.86–1.99 (m, 3H), 2.50–2.56 (m, 3H), 2.94 (s, 2H), 3.19–3.27 (m, 2H), 3.30 (s, 3H), 3.38 (dd, 1H), 3.43–3.45 (m, 2H), 3.50–3.54 (m, 3H), 5.92 (brs, 1H), 6.59 (d, 1H), 6.85 (d, 2H), 6.91 (s, 1H). LRMS: M + Na, 540 (ES⁺). |
| 58 | Prep 70 | Prep 89 | (R)-methyl | 2,2-difluoro-benzodioxole with propyl chain | ¹HNMR (CDCl₃, 300 MHz) δ: 1.10 (d, 3H), 1.35–1.52 (m, 13H), 1.53–1.63 (m, 5H), 1.65–1.95 (m, 3H), 1.96–2.15 (m, 2H), 2.33 (m, 1H), 3.25 (m, 2H), 5.85 (brs, 1H), 6.82–6.98 (m, 3H). LRMS: M + H (454) MNa⁺ (476) ES⁺. |
| 59 | Prep 69 | Prep 133 | (S)-methoxy ethyl | 2,3-dihydrobenzofuran with propyl chain (with Me) | ¹HNMR (CDCl₃, 400 MHz) δ: 1.20 (d, 3H), 1.40 (s, 9H), 1.50–1.90 (m, 14H), 2.30 (m, 1H), 2.65 (m, 3H), 3.05 (m, 1H), 3.15 (t, 2H), 3.20 (m, 1H), 3.25 (s, 3H), 3.30 (t, 2H), 4.50 (t, 2H), 5.65 (brs, 1H), 6.70 (d, 1H), 6.90 (d, 1H), 7.0 (s, 1H). LRMS: M + H, 474.3 (TS⁺). |
| 60 | Prep 69 | Prep 91 | (S)-methoxy ethyl | 2,3-dihydrobenzofuran with propyl chain | ¹HNMR (CDCl₃, 400 MHz) δ: 1.40 (s, 9H), 1.50–2.00 (m, 14H), 2.20 (s, 3H), 2.40 (m, 1H), 2.55 (t, 2H), 3.10 (m, 2H), 3.30 (m, 7H), 4.50 (t, 2H), 5.80 (brs, 1H), 6.60 (s, 1H), 6.90 (s, 1H). LRMS: M + H, 474.4 (TS⁺). |
| 61 | EP0342850, see also Tet. Letts., 1999, 40, 2187 | J. Med. Chem., 1996, 39, 4942–4951. | (S)-methoxy ethoxy methyl | 4-chlorophenyl with propyl chain | ¹HNMR (CDCl₃, 300 MHz) δ: 1.40 (s, 9H), 1.42 (m, 2H), 1.60 (m, 4H), 1.70 (m, 2H), 1.90 (m, 4H), 2.50 (m, 1H), 2.55 (t, 2H), 3.20 (m, 2H), 3.25 (s, 3H), 3.35 (m, 1H), 3.40 (m, 2H), 3.50 (m, 3H), 6.05 (brs., 1H), 7.05 (d, 2H), 7.17 (d, 2H). LRMS: M + H, 483.8 (TS⁺). |
| 62 | Prep 69 | Prep 146 | (S)-methoxy ethyl | 2,3-dihydrobenzofuran with gem-dimethyl propyl chain | ¹HNMR (CDCl₃, 400 MHz) δ: 1.35 (s, 6H), 1.4 (s, 9H), 1.5–1.65 (m, 8H), 1.7–1.9 (m, 6H), 2.3 (m, 1H), 3.1 (q, 2H), 3.2 (t, 2H), 3.25 (s, 3H), 3.35 (t, 2H), 4.53 (t, 2H), 5.45 (brs., 1H), 6.7 (d, 1H), 7.1 (d, 1H), 7.2 (s, 1H). |

TABLE 2-continued
(IVa)
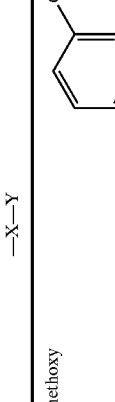
| Prep | Prec. acid | Prec. amine | R¹ | —X—Y | Analytical Data |
|---|---|---|---|---|---|
| 63 | Prep 69 | Prep 148 | (S)-methoxy ethyl | 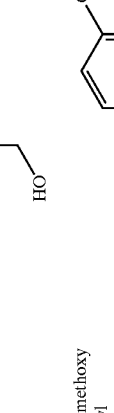 | ¹HNMR (CDCl₃, 400 MHz) δ: 1.30–2.20 (m, 23H), 2.38 (m, 1H), 2.81 (m, 1H), 3.11–3.39 (m, 7H), 3.72 (m, 2H), 5.90 (m, 1H), 7.18 (d, 2H), 7.26 (d, 2H). |
| 64 | Prep 69 | Prep 152 | (S)-methoxy ethyl | 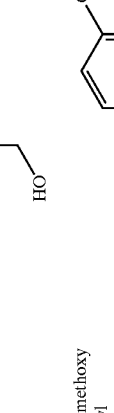 | ¹HNMR (CDCl₃, 400 MHz) δ: 1.41 (s, 9H), 1.26–2.02 (m, 17H), 2.26–2.38 (m, 1H), 3.00–3.11 (m, 1H), 3.12–3.22 (m, 1H), 3.26 (s, 3H), 3.27–3.39 (m, 2H), 3.65–3.73 (m, 2H), 5.97 (br.s, 1H), 7.26–7.37 (m, 4H). |
| 65 | Prep 69 | Prep 123 | (S)-methoxy ethyl | 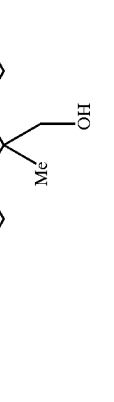 | ¹HNMR (CDCl₃, 400 MHz) δ: 1.20–2.00 (m, 23H), 2.34 (brm, 1H), 2.57 (t, 2H), 3.22 (s, 3H), 3.24–3.37 (m, 2H), 3.81 (s, 3H), 4.10 (q, 2H), 5.80 (brs., 1H), 6.81 (d, 1H), 7.02 (d, 1H), 7.18 (s, 1H). |
| 66 | Prep 69 | Prep 92 | (S)-methoxy ethyl |  | ¹HNMR (CDCl₃, 400 MHz) δ: 1.39–1.46 (m, 14H), 1.56–2.02 (m, 12H), 2.30–2.46 (m, 1H), 2.55 (dd, 2H), 2.76 (dd, 1H), 3.23–3.32 (m, 8H), 4.83–4.93 (m, 1H), 5.76 (brs, 1H), 6.63 (d, 1H), 6.90 (d, 1H), 6.97 (s, 1H), LRMS: M + Na, 496 (ES⁺). |

Alternatively Preparation 22 was prepared as follows:

To a solution of 1,1'-carbonyl diimidazole (73.9 g, 0.45 mol) in azeotropically dried isopropyl acetate (339 ml) was added the isopropyl acetate solution of the product from Preparation 69 with stirring at 60° C. under an atmosphere of $N_2$ over a period of 1.5 hours. The transfer lines were then washed with dry isopropyl acetate (50 ml). The resultant solution was then stirred at 60° C. for a further 4.5 hours and then the reaction mixture was allowed to cool to room temperature and stirred for 15 hours. To the resultant solution was then added triethylamine (46.1 g, 0.46 mol), followed by 3-(4-chlorophenyl)propylamine hydrochloride (J. Med. Chem., 1996, 39, 4942–51)(94.3 g, 0.46 mol). The resultant mixture was then heated to 60° C. for 7 hours before cooling to room temperature. Deionised water (100 ml) was then added to the reaction mixture with stirring, followed by aqueous hydrochloric acid (190 ml of a 5 M solution) until the pH of the aqueous layer was between pH 2 and 3. The aqueous layer was then separated, and the organic layer was washed with aqueous potassium carbonate (50 ml of a 0.5 M solution). The aqueous phase was separated and organic phase was washed with saturated brine solution (100 ml). The aqueous layer was then separated and the organic phase was concentrated by distillation under vacuum to give the title compound as a yellow oil (200.3 g, 443 mmol, 98% yield); $^1$H NMR (CDCl$_3$ 300 MHz) δ: 1.45 (s, 9H), 1.45–1.56 (m, 1H), 1.56–1.74 (m, 6H), 1.74–2.11 (m, 7H), 2.32–2.43 (m, 1H), 2.64 (t, 2H), 3.22–3.30 (m, 2H), 3.27 (s, 3H), 3.30–3.38 (m, 2H), 5.75–5.85 (m, br, 1H), 7.13 (d, 2H), 7.26 (d, 2H); LRMS (ES positive): m/z 452 [M+H]$^+$ ($^{35}$Cl).

Alternatively 3-(4-chlorophenyl)propylamine was prepared as follows:

To a stirred solution of the staring material from stage b) below (11.3 g, 62 mmol) in tetrahydrofuran (500 ml) was added borane dimethylsulphide complex (30 ml) and the whole was refluxed for 12 h. The reaction mixture was quenched with methanol (100 ml), concentrated in vacuo and refluxed for 4 h in 3M HCl (200 ml). The aqueous layer was concentrated to 50 ml in vacuo, the precipitate was filtered off and dried under reduced pressure to give the title product as a white powder (10.1 g, 59.7 mmol, 96%); $^1$HNMR (400 MHz, MeOD) δ: 1.9 (quin, 2H), 2.65 (t, 2H), 2.9 (t, 2H), 7.2 (d, 2H), 7.25 (d, 2H).

Preparation of Starting Materials
  a) Methyl 3-(4-chlorophenyl)propanoate

To a stirred solution of 3-(4-chlorophenyl)propanoic acid (commercially available from Maybridge) (14.5 g, 77.1 mmol) in methanol (400 ml) was added acetyl chloride (50 ml) and the reaction mixture was refluxed for 20 h. After this time the reaction mixture was left to cool before being concentrated under reduced pressure. The residue was then dissolved in DCM (200 ml) and washed with 1M sodium hydroxide solution (100 ml). The organic layer was dried with magnesium sulphate and concentrated in vacuo to give the title product as a brown oil (15.7 g, 77 mmol, 100%); $^1$HNMR (400 MHz, CDCl$_3$) δ: 2.55 (t, 2H), 2.9 (t, 2H), 3.6 (s, 3H), 7.1 (d, 2H), 7.2 (d, 2H).

b) 3-(4-chlorophenyl)propanamide

The product from stage a) above (15 g, 75.7 mmol) was dissolved in methanol (400 ml) before being cooled to 0° C. Ammonia gas was then bubbled through the reaction mixture for 4 hours and the reaction was left to stir for 3 days. The solvent was removed under reduced pressure and the residue was triturated with hot pentane. The remaining solid was dried in vacuo to give the title product as a white powder (11.32 g, 61.8 mmol, 82%); $^1$HNMR (400 MHz, CDCl$_3$) δ: 2.45 (t,2H), 2.9 (t, 2H), 5.3 (bs, 1H), 5.5 (bs, 1H), 7.1 (d, 2H), 7.2 (d, 2H).

Preparation 67
tert-Butyl-[1-({[3-(4-cyanophenyl)propyl]amino}carbonyl)cyclopentyl]acetate

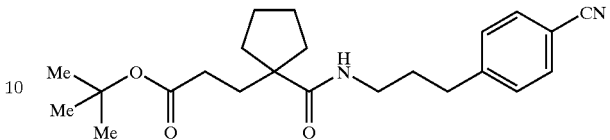

The product from Preparation 45 (44 mg, 0.1 mmol) and Cu(I)CN (13.4 mg, 0.15 mmol) were taken up in DMF (0.5 ml) under nitrogen and stirred at ca. 130° C. for 16 h. After this time, a further 13 mg of Cu(I)CN were added and the temperature raised to 145° C. for 16 h. After this time, a final 26 mg of Cu(I)CN were added to the solution and the whole heated at 160° C. for 24 h. The reaction was quenched by the addition of water and the organics extracted with EtOAc (50 ml), washed with brine and dried (MgSO$_4$) and evaporated to a yellow oil. This oil was subjected to preparative TLC purification using 7:3 pentane:EtOAc as eluant to give the title product, 6 mg (16%); $^1$HNMR (400 MHz, CDCl$_3$) δ: 1.40 (s, 9H), 1.45–1.49 (m, 2H), 1.62–1.64 (m, 4H), 1.79–1.83 (m, 4H), 1.94–2.00 (m, 2H), 2.12–2.17 (m, 2H), 2.65 (t, 2H), 3.22–3.35 (m, 2H), 5.65 (brs, 1H), 7.23 (d, 2H), 7.54 (d, 2H); LRMS: m/z (ES$^+$) 407 (M+Na).

Preparations 68
1-[2-(tert-Butoxycarbonyl)-4-methoxybutyl]cyclopentanecarboxylic acid

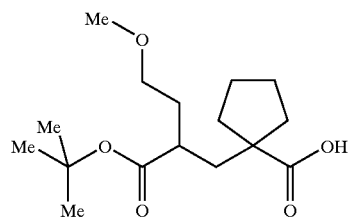

A solution of tert-butyl 3-(1-carboxycyclopentyl) propanoate (12 g, 49.5 mmol) (see EP274234B1, Example 35) in dry tetrahydrofuran (100 ml) was added to a stirred solution of lithium diisopropylamide (130 ml) in a mixture of hexane (52 ml) and tetrahydrofuran (200 ml) at −78° C. under nitrogen. After 1 hour a solution of 2-bromoethyl methyl ether in tetrahydrofuran (100 ml) was added maintaining the temperature at −78° C. The reaction mixture was allowed to warm up to room temperature overnight. The mixture was quenched with water (100 ml) and acidified to pH 1 with 2M hydrochloric acid, and extracted with ethyl acetate (2×150 ml). The combined organic extracts were dried over magnesium sulfate and concentrated in vacuo to give the crude acid which was chromatographed on silica. Elution with increasing proportions of methanol in dichloromethane (neat dichloromethane to 1:50) gave an oil (7.7 g, 25.6 mmol, 52%); Rf 0.3 methanol, dichloromethane 1:20; $^1$H NMR (CDCl$_3$ 400 MHz) δ: 1.4 (s, 9H), 1.4–1.7 (m, 7H), 1.75–1.95 (m, 2H), 2.0–2.15 (m, 3H), 2.3–2.4 (m, 1H), 3.3 (s, 3H), 3.3–3.4 (m, 2H); LRMS: m/z 299 (M−H$^+$).

Alternatively the compound of Preparation 68 was prepared as follows:

To a mixture of heptane (41.2 L) and water (30.9 L) was added the product from stage b) below (5.15 kg, 12.9 mol).

Dilute aqueous hydrochloric acid (2.6 L of a 5 M solution) was then added with stirring until the pH of the aqueous layer was between pH 2 and 3. The layers were separated and the aqueous phase was then extracted with heptane (20.6 L). The combined organic layers were then washed with saturated brine solution (15.5 L) and were then concentrated by distillation at atmospheric pressure to give the title compound (3.90 kg, 13.0 mol, 100% yield) as a solution in heptane (total solution weight 44.0 kg). An aliquot can be taken and the solvent removed under vacuum to give an analytical sample; 1H NMR (CDCl3 300 MHz) δ: 1.42 (s, 9H), 1.45–1.58 (m, 2H), 1.58–1.70 (m, 5H), 1.70–1.90 (m, 2H), 2.03–2.18 (m, 3H), 2.32–2.46 (m, 1H), 3.27 (s, 3H), 3.35 (t, 2H); LRMS (EI): m/z 244 [M−C4H8]+, 227 [M−C4H9O]+, 199 [M−C4H9O2C]+; GC (injector program: initial temp. 0° C., rate 150° C./min, final temp. 230° C.; oven program: initial temp. 100° C., rate 10° C./min, final temp. 230° C., final time 10 min; column, BP-21 25 m×0.25 mm ID×0.25 um FT; detector FID) RT 16.1 min.

Preparation of Starting Materials a) Crude 1-[2-(tert-butoxycarbonyl)-4-methoxybutyl]cyclopentanecarboxylic acid To a solution of commercially supplied lithium diisopropylamide (9.63 kg of a 2M solution in tetrahydrofuran/n-heptane/ethylbenzene, 23.7 mol) in 1,2-dimethoxyethane (25 L) at −10° C. under an atmosphere of N$_2$ was added a solution of 1-(3-tert-butoxy-3-oxopropyl)cyclopentane carboxylic acid (EP274234B1—see Example 35) (2.5 kg, 10.3 mol) in 1,2-dimethoxyethane (12.5 L) with stirring over a period of 4 hours whilst maintaining the reaction temperature at −10° C. The header tank was washed with 1,2-dimethoxyethane (2.5 L) and this was added to the reaction. The reaction mixture was then allowed to stir at −10° C. for 1.75 hours. To the resultant solution was added a solution of 2-iodoethyl methyl ether (2.73 kg, 14.4 mol) in 1,2-dimethoxyethane (10 L) over a period of 1.75 hours. The reaction was then stirred at this temperature for 4 hours before warming to 20° C. over a period of 4 hours. After stirring at this temperature for 8 hours the reaction was quenched by the addition of aqueous ammonium chloride (25 L of a 2.8 M solution), ethyl acetate (12.5 L) was then added. Aqueous hydrochloric acid (10 L of 5 M solution) was then added with stirring to adjust the pH to between 2 and 3. The two phases were mixed and then separated. The organic phase was then extracted three times with aqueous potassium carbonate solution (0.3 M solution; 37.5 L, 12.5 L and then 6.25 L). To the combined aqueous phases was then added n-heptane (15.6 L), and aqueous hydrochloric acid (14.5 L of a 5 M solution) with stirring until the pH of the aqueous layer was between 2 and 3. The layers were then separated and the aqueous phase was extracted with n-heptane (15.6 L). The combined organic phases were then washed with saturated brine (3.1 L) and were then concentrated under vacuum to give the crude title compound (2.50 kg, 8.32 mol, 81% yield) as a solution in n-heptane (21.8 kg total solution weight).

b) Cyclohexanaminium 1-[2-(tert-butoxycarbonyl)-4-methoxybutyl]cyclopentane carboxylate A solution of the crude product from stage a) above in n-heptane (5.51 kg, 18.3 mol in a total solution weight of 41.4 kg) was concentrated by distillation at atmospheric pressure to remove 20 L of n-heptane To the resultant solution was added cyclohexylamine (1.82 kg, 18.4 mol) as a solution in n-heptane (9.9 L) over a period of 0.5 hours. The transfer lines were then washed with n-heptane (1.1 L) and this was added to the reaction. The resultant slurry was then granulated with agitation at 22° C. for a period of 19.5 hours. The product was collected by filtration and washed with n-heptane (2×11.0 L) and the resultant solid was dried under vacuum at 50° C. for 20 hours. The resultant off-white solid (6.2 kg, 15.5 mol) was suspended in isopropyl acetate (37.2 L) and the resultant suspension was heated to 80° C. until a clear solution was obtained. The resultant solution was then cooled to 50° C. and a sample of authentic crystallised title compound (1.0 g) was added to seed the crystallisation. The crystallising slurry was then cooled to 20° C. over 4 hours and was then granulated at this temperature for 0.5 hours. The product was then collected by filtration and was washed with n-heptane (2×6.2 L) before being dried under vacuum at 45° C. for 11 hours. The resultant white solid (5.5 kg, 13.8 mol) was then suspended in isopropyl acetate (55.0 L) and was heated to 80° C. until a clear solution was obtained. The resultant solution was then cooled to 50° C. and a sample of authentic crystallised title compound (1.0 g) was added to seed the crystallisation. The crystallising slurry was then cooled to 20° C. over 4 hours and then granulated at this temperature for 22.5 hours. The product was then collected by filtration and was washed with n-heptane (2×5.5 L) before being dried under vacuum at 45° C. for 16.5 hours to give the title product (5.15 kg, 12.9 mol, 94% yield); m.p. (heptane) 121° C.; 1H-NMR (CDCl3, 300 MHz), δ: 1.06–1.37 (m, 7H), 1.42 (s, 9H), 1.50–1.67 (m, 5H), 1.67–1.86 (m, 5H), 1.86–2.18 (m, 5H), 2.30–2.58 (m, 1H), 2.80–2.93 (m, 1H), 3.29 (s, 3H), 3.35 (q, 2H), 7.29 (s, br, 3H); Anal. found C, 66.20; H, 10.26; N, 3.50; C22H41NO5 requires C, 66.13; H, 10.34; N, 3.51%.

Preparation 69

1-[(2S)-2-(tert-Butoxycarbonyl)-4-methoxybutyl]cyclopentanecarboxylic acid

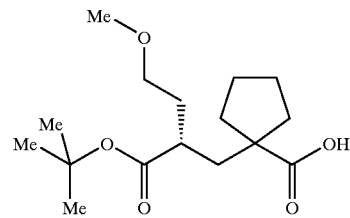

The product from Preparation 68 and (+)-pseudoephedrine were recrystallised nine times from hexane to give a white crystaline solid. The salt was dissolved in ethyl acetate washed with 0.5M hydrochloric acid dried over magnesium sulphate and concentrated in vacuo the (S)-acid was obtained in 31% yield as a pale yellow oil in >90% ee by NMR analysis of the δ 3.3 peak of the (+)-pseudoephedrine salt; $^1$H NMR (CDCl$_3$ 400 MHz) δ: 1.4 (s, 9H), 1.4–1.7 (m, 7H), 1.75–1.9 (m, 2H), 2.0–2.15 (m, 3H), 2.35–2.45 (m, 1H), 3.3 (s, 3H), 3.3–3.4 (m, 2H); [α]$_D$ −5.2 (EtOH, c 1.2).

Alternatively Preparation 69 was prepared as follows:

To a solution of the product from Preparation 68 (3.90 kg, 13.0 mol) in heptane (58.5 L, total solution weight 44.0 kg) was added (1S, 2S)-(+)-pseudoephedrine (2.13 kg, 12.9 mol) under an atmosphere of nitrogen at 20° C. The suspension was then heated to 70° C. with stirring until a clear solution was obtained. The solution was then cooled to 40° C. and a sample of authentic crystallised title compound (0.8 g) was added to seed the crystallisation. The temperature of the mixture was maintained at 40° C. for 2 hours and then the slurry was cooled to 20° C. over 6 hours. The product was then collected by filtration and was washed with heptane (2×2.3 L) then dried under vacuum for 22 hours at 50° C. to give (1S,2S)-1-hydroxy-N-methyl-1-phenyl-2-propanaminium 1-[(2S)-2-(tert-butoxy carbonyl)-4-methoxybutyl]cyclopentane carboxylate (3.20 kg, 6.87 mol, 53% yield as an 86:14 mixture of diastereoisomeric salts as measured by $^1$H NMR). The product (3.20 kg, 6.87 mol) was then suspended in heptane (30 L) and heated to 70° C. until a clear solution was obtained. The resultant solution was then cooled to 58° C. and a sample of authentic crystallised title compound (1.0 g) was added to seed the crystallisation. The solution was then held at 58° C. for 1 hour and was then cooled to 20° C. over 6 hours. The slurry was then granulated at 20° C. for 12 hours. The product was then collected by filtration and was washed with heptane (2×2 L). Drying in a vacuum oven at 50° C. for 22.5 hours gave (1S,2S)-1-hydroxy-N-methyl-1-phenyl-2-propanaminium 1-[(2S)-2-(tert-butoxycarbonyl)-4-methoxybutyl]cyclopentane carboxylate as a white crystalline solid (2.35 kg, 5.0 mol, 73% yield). m.p. (heptane); 95° C.; $^1$H-NMR (CDCl$_3$, 300 MHz) δ: 1.08 (d, 3H), 1.48 (s, 10H), 1.56–1.74 (m, 4H), 1.74–1.90 (m, 2H), 1.90–2.03 (m, 2H), 2.03–2.27 (m, 2H), 2.4–2.53 (m, 1H), 2.66 (s, 3H), 3.08 (dq, 1H), 3.24 (s, 3H), 3.38 (q, 2H), 4.58 (d, 1H), 7.27–7.45 (m, 5H), 7.70 (s, br, 3H); Anal. found C, 67.06; H, 9.35; N, 3.04; C$_{26}$H$_{43}$NO$_6$ requires C, 67.07; H, 9.31; N, 3.01%. The title compound was obtained by breaking the salt as follows. To a stirred suspension of (1S,2S)-1-hydroxy-N-methyl-1-phenyl-2-propanaminium 1-[(2S)-2-(tert-butoxycarbonyl)-4-methoxybutyl] cyclopentane carboxylate (210 g, 0.45 mol) in deionised water (1.26 L) and isopropyl acetate (1.47 L) was added aqueous hydrochloric acid (99.5 ml of a 5 M solution, 0.50 mol) until the pH of the aqueous layer was between pH 2 and 3. The layers were then separated, and the aqueous phase was extracted with isopropyl acetate (630 ml). The organic extracts were then combined and washed with saturated brine solution (420 ml). The organic phase was then concentrated by distillation at atmospheric pressure (to remove 1.4 L of isopropyl acetate) to give the title compound as a solution in isopropyl acetate which was used directly in the next step. An aliquot can be taken and the solvent removed to give an analytical sample; $^1$H NMR (CDCl$_3$ 300 MHz) δ: 1.44 (s, 9H), 1.48–1.59 (m, 2H), 1.59–1.72 (m, 5H), 1.72–1.93 (m, 2H), 2.03–2.18 (m, 3H), 2.35–2.46 (m, 1H), 3.31 (s, 3H), 3.38 (t, 2H); LRMS (EI): m/z 244 [M−C$_4$H$_8$]$^+$, 227 [M−C$_4$H$_9$O]$^+$, 199 [M−C$_4$H$_9$O$_2$C]$^+$; GC (injector program: initial temp. 0° C., rate 150° C./min, final temp. 230° C.; oven program: initial temp. 100° C., rate 10° C./min, final temp. 230° C., final time 20 min; column, BP-21 25 m×0.25 mm ID×0.25 um FT; detection FID) Retention Time 16.0 min; HPLC (column: ChiralPak AD (25×0.46 cm); mobile phase: hexane/IPA/acetic acid (98/2/0.1 v/v/v); Rinsing mobile phase: hexane/IPA/DEA (80/20/0.5 v/v/v); flow rate: 1.0 ml/min; temperature: ambient; injection volume: 20 μl; detection: ELSD) Run time: 20 mins followed by 10 mins rinse with hexane/IPA/acetic acid (98/2/0.1 v/v/v), followed by 10 mins rinse with hexane/IPA/acetic acid (98/2/0.1 v/v/v); Retention Time: minor enantiomer 15.5 min (3.3%), major enantiomer 17.5 min (96.7%).

Alternatively the product from Preparation 69 was prepared by asymmetric hydrogenation using a number of catalysts and conditions as follows.

i) Hydrogenation 1

The starting material from stage c) below (62 mg, 0.21 mmol) and [(R)-(+)-2,2'-bis(diphenylphosphino)-1,1'-binaphthylchloro(para-cymene)]ruthenium chloride (J. Org. Chem. 1994, 59, 3064–76) (2.0 mg, 0.0021 mmol) were charged to the pressure vessel. The vessel was purged with nitrogen by pressurising to 10 bar and then venting. This purging procedure was then repeated a further 4 times. Degassed methanol (2 ml) was then added. The vessel was pressurised with hydrogen (10 bar), then vented and pressurised again with hydrogen (10 bar). The mixture was stirred at 65° C. (oil bath temperature) for 18 h. After cooling to room temperature, the pressure was released and the solvent was removed under reduced pressure to give the title compound as an oil, HPLC (column: ChiralPak AD (25× 0.46 cm); mobile phase: hexane/IPA/acetic acid (98/2/0.1 v/v/v); rinsing mobile phase: hexane/IPA/DEA (80/20/0.5 v/v/v); flow rate: 1.0 ml/min; temperature: ambient; injection volume: 20 μl; detection: ELSD) Run time: 20 mins followed by 10 mins rinse with hexane/IPA/acetic acid (98/2/0.1 v/v/v), followed by 10 mins rinse with hexane/IPA/acetic acid (98/2/0.1 v/v/v); retention Time: R enantiomer 15.5 min, S enantiomer 17.5 min; 91% conversion, S-enantiomer, ee 97%.

ii) Hydrogenation 2

The starting material from stage c) below (82 mg, 0.27 mmol), sodium tert-butoxide (25 mg, 0.26 mmol) and [(S)-3,3',4,4',5,5'-hexamethyl(6,6'-diphenyl)-2,2'-diyl]bis (diphenylphosphino)ruthenium bis(trifluoroacetate) (see WO01/94359) (2.5 mg, 0.0027 mmol) were charged to the pressure vessel. The vessel was purged with nitrogen by pressurising to 10 bar and then venting. This purging procedure was then repeated a further 4 times. Degassed methanol (2 ml) was then added. The vessel was pressurised with hydrogen (10 bar), then vented and pressurised again with hydrogen (10 bar). The mixture was then stirred at 65° C. for 18 h. The vessel was then allowed to cool to room temperature and the pressure was then released. To the reaction mixture was then added ethyl acetate/heptane (1:1, 10 ml) and hydrochloric acid (1M, 5 ml). The organic phase was separated and dried over magnesium sulfate and the solvent was removed under reduced pressure to give the title compound as an oil, HPLC (column: ChiralPak AD (25× 0.46 cm); mobile phase: hexane/IPA/acetic acid (98/2/0.1 v/v/v); Rinsing mobile phase: hexane/IPA/DEA (80/20/0.5 v/v/v); flow rate: 1.0 ml/min; temperature: ambient; injection volume: 20 μl; detection: ELSD) Run time: 20 mins followed by 10 mins rinse with hexane/IPA/acetic acid (98/2/0.1 v/v/v), followed by 10 mins rinse with hexane/IPA/acetic acid (98/2/0.1 v/v/v); Retention Time: R enantiomer 15.5 min, S enantiomer 17.5 min; >98% conversion, R-enantiomer, ee 91%.

iii) Hydrogenation 3

Using the same method as described for Hydrogenation 2 above but using [(R)-(6,6'-dimethoxybiphenyl-2,2'-diyl)bis (diphenylphosphino)]ruthenium bis(trifluoroacetate) (EP398132) as the pre-catalyst gave the title compound as an oil, HPLC (column: ChiralPak AD (25×0.46 cm); mobile phase: hexane/IPA/acetic acid (98/2/0.1 v/v/v); Rinsing mobile phase: hexane/IPA/DEA (80/20/0.5 v/v/v); flow rate: 1.0 ml/min; temperature: ambient; injection volume: 20 μl; detection: ELSD) Run time: 20 mins followed by 10 mins rinse with hexane/IPA/acetic acid (98/2/0.1 v/v/v), followed by 10 mins rinse with hexane/IPA/acetic acid (98/2/0.1 v/v/v); Retention Time: R enantiomer 15.5 min, S-enantiomer 17.5 min; 57% conversion, S-enantiomer, ee>98%.

iv) Hydrogenation 4

The starting material from stage i) below (80 mg, 0.25 mmol) and [(R)-(−)-4,12-bis(diisopropylphosphino)-[2.2]-paracyclophano-(1,5-cyclooctadiene)]rhodium (I) tetrafluoroborate (J. Am. Chem. Soc. 1997, 119, 6207–6208) (1.8 mg, 0.0025 mmol) were charged to a pressure vessel. The vessel was then purged with nitrogen by pressurising to 10.5 bar and then venting. This purging procedure was then repeated a further 4 times. Degassed methanol (2 ml) was then added. The vessel was pressurised with hydrogen (10.5 bar), then vented and pressurised again with hydrogen (10.5 bar). The mixture was then stirred at room temperature for 18 h and the pressure was then released. To the reaction mixture was added tert-butyl methyl ether and 2M hydrochloric acid and the phases were mixed. The organic phase was separated, dried over magnesium sulfate, and the solvent was removed under reduced pressure to give the title compound as an oil, HPLC (column: ChiralPak AD (25×0.46 cm); mobile phase: hexane/IPA/acetic acid (98/2/0.1 v/v/v); Rinsing mobile phase: hexane/IPA/DEA (80/20/0.5 v/v/v); flow rate: 1.0 ml/min; temperature: ambient; injection volume: 20 µl; detection: ELSD) Run time: 20 mins followed by 10 mins rinse with hexane/IPA/acetic acid (98/2/0.1 v/v/v), followed by 10 mins rinse with hexane/IPA/acetic acid (98/2/0.1 v/v/v); Retention Time: R enantiomer 15.5 min, S enantiomer 17.5 min; >98% conversion, R-enantiomer, ee 91%.

v) Hydrogenation 5

The starting material from stage i) below (80 mg, 0.25 mmol) and [(S)-3,3',4,4',5,5'-hexamethyl(6,6'-diphenyl)-2,2'-diyl]bis(diphenylphosphino)ruthenium bis(trifluoroacetate) (see WO 01/94359) (2.3 mg, 0.0025 mmol) were charged to the pressure vessel. The vessel was purged with nitrogen by pressurising to 10.5 bar and then venting. This purging procedure was then repeated a further 4 times. Degassed methanol (2 ml) was then added. The vessel was pressurised with hydrogen (10.5 bar), then vented and pressurised again with hydrogen (10.5 bar). The mixture was stirred at 45° C. for 18 h and then allowed to cool to room temperature. The pressure was then released and to the reaction mixture was added tert-butyl methyl ether and 2M hydrochloric acid and the phases were mixed. The organic phase was separated and dried over magnesium sulfate, and the solvent was then removed under reduced pressure to give the title compound as an oil, HPLC (column: ChiralPak AD (25×0.46 cm); mobile phase: hexane/IPA/acetic acid (98/2/0.1 v/v/v); Rinsing mobile phase: hexane/IPA/DEA (80/20/0.5 v/v/v); flow rate: 1.0 ml/min; temperature: ambient; injection volume: 20 µl; detection: ELSD) Run time: 20 mins followed by 10 mins rinse with hexane/IPA/acetic acid (98/2/0.1 v/v/v), followed by 10 mins rinse with hexane/IPA/acetic acid (98/2/0.1 v/v/v); Retention Time: R enantiomer 15.5 min, S enantiomer 17.5 min; >98% conversion, R-enantiomer, ee 97%.

vi) Hydrogenation 6

The starting material from stage i) below (80 mg, 0.25 mmol) and [(R)-(+)-2,2'-bis(diphenylphosphino)-1,1'-binaphthyl]ruthenium bis(trifluoroacetate)] (2.4 mg, 0.0025 mmol) or [(R)-(+)-2,2'-bis(diphenylphosphino)-1,1'-binaphthylchloro(para-cymene)]ruthenium chloride (*J. Org. Chem.* 1994, 59, 3064–76) (2.4 mg, 0.0025 mmol) were charged to the pressure vessel. Using the same procedure as described in preparation 6 gave the title compound as an oil; HPLC (column: ChiralPak AD (25×0.46 cm); mobile phase: hexane/IPA/acetic acid (98/2/0.1 v/v/v); Rinsing mobile phase: hexane/IPA/DEA (80/20/0.5 v/v/v); flow rate: 1.0 ml/min; temperature: ambient; injection volume: 20 ∞l; detection: ELSD) Run time: 20 mins followed by 10 mins rinse with hexane/IPA/acetic acid (98/2/0.1 v/v/v), followed by 10 mins rinse with hexane/IPA/acetic acid (98/2/0.1 v/v/v); Retention Time: R enantiomer 15.5 min, S enantiomer 17.5 min; >98% conversion, S-enantiomer, ee>98%.

vii) Hydrogenation 7

The starting material from stage i) below (80 mg, 0.25 mmol) and [(R)-(6,6'-dimethoxybiphenyl-2,2'-diyl)bis(diphenylphosphino)]ruthenium bis(trifluoroacetate) (EP398132) (2.3 mg, 0.0025 mmol) were charged to the pressure vessel. Using the same procedure as described in hydrogenation 6 gave the title compound as an oil HPLC (column: ChiralPak AD (25×0.46 cm); mobile phase: hexane/IPA/acetic acid (98/2/0.1 v/v/v); Rinsing mobile phase: hexane/IPA/DEA (80/20/0.5 v/v/v); flow rate: 1.0 ml/min; temperature: ambient; injection volume: 20 µl; detection: ELSD) Run time: 20 mins followed by 10 mins rinse with hexane/IPA/acetic acid (98/2/0.1 v/v/v), followed by 10 mins rinse with hexane/IPA/acetic acid (98/2/0.1 v/v/v); Retention Time: R enantiomer 15.5 min, S enantiomer 17.5 min; >98% conversion, S-enantiomer, ee>98%.

Preparation of Starting Materials a) 1-(2-tert-Butoxycarbonyl-4-methoxy-3-oxo-butyl)-cyclopentane carboxylic acid A solution of diisopropylamine (35.0 ml, 250 mmol) in THF (70 ml) was cooled to −15° C. under nitrogen. n-Butyllithium (2.5 M, 100 ml, 250 mmol) was then added dropwise, whilst maintaining the temperature below −10° C. To the resultant solution was added a solution of 1-(3-tert-butoxy-3-oxopropyl)cyclopentane carboxylic acid (see EP274234B1, example 35) (27.52 g, 113.6 mmol) in THF (50 ml) and the reaction was then stirred at −10 to −15° C. for 1 h. To the reaction mixture was then added a solution of methyl methoxyacetate (18.0 ml) in THF (20 ml), and the resultant mixture was then allowed to warm to room temperature and then stirred for 19 hours. To the reaction mixture was added tert-butyl methyl ether (300 ml) and deionised water (300 ml), and the aqueous phase was then acidified with 2M hydrochloric acid to pH 3 with stirring. The phases were separated and the aqueous phase was then extracted with tert-butyl methyl ether (250 ml). The combined organic phases were then washed with water (250 ml) and then brine (250 ml), dried over magnesium sulfate, and the solvent was then removed under reduced pressure. The crude title compound was then purified by flash chromatography on silica gel using ethyl acetate/heptane (1:2 to 1:1) as the eluent to give the title compound (17.35 g, 55.2 mmol, 49% yield);

$^1$H NMR (400 MHz, CDCl$_3$) δ: 1.43 (s, 9H), 1.69–1.47 (m, 6H), 2.17–2.05 (m, 2H), 2.18 (dd, 1H), 2.32 (dd, 1H), 3.42 (s, 3H), 3.59 (t, 1H), 4.17 (q, 2H); $^{13}$C NMR (100 MHz, CDCl$_3$) δ:24.7, 27.8, 34.9, 35.8, 36.7, 53.2, 53.3, 59.2, 82.3, 168.3, 183.4, 203.2.

b) 8-Methoxymethyl-6-oxo-7-oxa-spiro[4.5]decane-9-carboxylic acid tert-butyl ester A solution of the product from stage a) above (10.50 g, 33.4 mmol) in methanol (100 ml) was cooled to 0 to −5° C. under nitrogen. To the resultant solution was then added sodium borohydride (2.02 g, 53.4 mmol) in portions, keeping the temperature below 0° C. The reaction was then stirred for 1 hour. Ethyl acetate (150 ml) and water (150 ml) were then added, and the aqueous phase was acidified by adding hydrochloric acid (50 ml of a 2 M solution) with stirring. The phases were then separated and the aqueous phase was extracted with ethyl acetate (100 ml). The combined organic phases were then washed with water (50 ml) and then brine (50 ml). The combined aqueous washings were then extracted with ethyl acetate (100 ml). The combined ethyl acetate extracts were then dried over magnesium sulfate and the solvent was then removed under reduced pressure to give a pale yellow oil (11.29 g), that was used in the next step without further purification. A portion of this oil (10.89 g, 34.4 mmol) was dissolved in THF (100 ml) under nitrogen, and to the resultant solution was added dicyclohexylcarbodiimide (7.10 g, 34.4 mmol). The mixture was then stirred at room temperature for 19 hours. To the reaction was then added methanol (5 ml) and acetic acid (2 ml) and the mixture was then stirred for 30 minutes. The solvent was then removed under reduced pressure. The crude product was then suspended in ethyl acetate (50 ml) and the reaction by-products were removed by filtration. The filter cake was washed with ethyl acetate (50 ml) and the filtrate was then concentrated under reduced pressure. The crude title compound was then purified by flash chromatography on silica gel using ethyl acetate/heptane (1:3 to 2:3) as the eluent to give the title compound as a 2:1 mixture of diastereoisomers (8.19 g, 27.4 mmol, 80%); For analytical purposes a sample was purified by flash chromatography on silica gel using EtOAc/heptane (1:2) as the eluent; i) Higher rf spot (single diastereoisomer); $^1$H NMR (400 MHz, CDCl$_3$) δ: 1.47 (s, 9H), 1.50–2.15 (m, 9H), 2.30 (m, 1H), 2.90 (td, 1H), 3.38 (s, 3H), 3.58 (d, 2H), 4.62 (dt, 1H); $^{13}$C NMR (100 MHz, CDCl$_3$) δ ppm 25.5, 25.8, 28.0, 36.9, 38.3, 39.6, 40.4, 47.8, 59.5, 73.1, 79.5, 81.8, 171.3, 176.5; ii) Lower rf spot (not completely separated, 3.5:1 mixture of diastereoisomers); $^1$H NMR (400 MHz, CDCl$_3$) δ: (major isomer) 1.47 (s, 9H), 1.49–2.10 (m, 8H), 2.18 (dd, 1H), 2.43 (m, 1H), 3.03 (m, 1H), 3.35 (s, 3H), 3.60–3.67 (m, 2H), 4.72 (q, 1H).

c) 1-(2-tert-Butoxycarbonyl-4-methoxy-but-2E-enyl)-cyclopentane carboxylic acid

To a solution of the product from stage b) above (6.11 g, 20.49 mmol) in toluene (50 ml) was added 1,8-diazabicyclo[5.4.0]undec-7-ene (3.7 ml, 24.58 mmol), and the resultant solution was then heated at reflux under nitrogen for 5 h. The solution was then cooled to room temperature and the solvent was removed under reduced pressure. To the resultant residue was then added deionised water (100 ml) and the mixture was then extracted with tert-butyl methyl ether (30 ml). The phases were then separated and the aqueous phase was acidified to pH 2 with hydrochloric acid (15 ml of a 2 M solution) and then extracted with tert-butyl methyl ether (2×30 ml). The combined organic extracts were then washed with water (30 ml) and then brine (30 ml) and dried over magnesium sulfate. The solvent was then removed under reduced pressure to give the crude title compound (6.29 g), which was then crystallised from heptane (15 ml) at 0° C. The resultant solid was collected by filtration was then washed with ice-cold heptane (2×5 ml) to give the title compound as a white solid (1.79 g, 6.0 mmol, 29%, E-isomer assigned on basis of chemical shifts); $^1$H NMR (400 MHz, CDCl$_3$), δ: 1.47 (s, 9H), 1.45–1.70 (m, 6H), 2.05–2.10 (m, 2H), 2.74 (s, 2H), 3.36 (s, 3H), 4.09 (d, 2H), 6.75 (t, 1H); $^{13}$C NMR (100 MHz, CDCl$_3$) δ: 23.9, 28.0, 34.1, 35.0, 55.0, 58.6, 69.2, 80.8, 132.7, 139.1, 167.1, 183.3.

The filtration liquors were concentrated to give a yellow oil (4.02 g). This mixture was purified by flash chromatography on silica gel using ethyl acetate/heptane (1:2+0.5% acetic acid) as the eluent to give more of the title compound and a colourless oil (2.43 g, 1.1:1 E/Z ratio); 1-(2-tert-Butoxycarbonyl-4-methoxy-but-2Z-enyl)-cyclopentane carboxylic acid: $^1$H NMR (400 MHz, CDCl$_3$) δ: (key signals) 1.48 (s, 9H), 2.65 (s, 2H), 3.33 (s, 3H), 4.29 (d, 2H), 5.99 (t, 1H).

A sample of the vinyl ether 1-[(3E)-2-(tert-butoxycarbonyl)-4-methoxy-3-butenyl]cyclopentanecarboxylic acid was also isolated by flash chromatography (E geometry assigned on basis of coupling constant); $^1$H NMR (400 MHz, CDCl$_3$) δ: 1.42 (s, 9H), 1.40–1.70 (m, 6H), 2.03 (d, 2H), 2.06 (m, 1H), 2.17 (m, 1H), 2.83 (s, 1H), 3.49 (s, 3H), 4.66 (dd, 1H), 6.35 (d, 1H); $^{13}$C NMR (100 MHz, CDCl$_3$) δ: 24.9, 25.2, 28.4, 34.7, 38.8, 41.7, 44.3, 53.5, 56.1, 80.9, 101.9, 149.2, 174.5, 184.5.

d) 1-Benzyl 3-tert-butyl 2-(2-methoxyethyl)malonate

To a stirred suspension of sodium hydride (14.4 g of a 60% dispersion in mineral oil, 360 mmol) in THF (300 ml) was cooled to 0° C. under nitrogen. To the resultant slurry was added, over a period of 45 minutes, a solution of benzyl-tert-butyl malonate (90.0 g, 360 mmol) in THF (500 ml). The reaction mixture was allowed to warm to room temperature and was then stirred for 1 hour. The reaction mixture was then cooled to 0° C. again, and a solution of 2-bromoethyl methyl ether (50.0 g, 360 mmol) in THF (100 ml) was then added over a period of 0.5 hours. The reaction was then allowed to warm to room temperature and left to stir for 19 hours. The reaction was then brought to reflux for 24 hours before cooling to room temperature. To the reaction mixture was added deionised water (500 ml) and the product was then extracted with ethyl acetate (3×500 ml). The organic phases were combined, dried over magnesium sulfate and were then concentrated by distillation under reduced pressure to give the product as a crude oil (100 g). The product was then purified by column chromatography on silica gel using 10% diethyl ether in heptane then 20% diethyl ether in heptane as the eluent, to give the title compound as an oil (37.1 g, 120 mmol, 33% yield); TLC (diethyl ether/heptane 3:7, visualised with Dragendorff's dip) R$_f$ 0.25; $^1$H NMR (300 MHz, CDCl$_3$) δ: 1.4 (s, 9H), 2.13 (dt, 2H), 3.30 (s, 3H), 3.43 (t, 2H), 3.51 (t, 1H), 5.20 (d, 2H), 7.29–7.40 (m, 5H).

e) 2-(tert-Butoxycarbonyl)-4-methoxybutanoic acid

To a solution of the product from stage d) above (37.1 g, 120 mmol) in dioxane (740 ml) and water (111 ml) was added potassium hydroxide (6.73 g, 120 mmol) with stirring. The resultant solution was then stirred at room temperature for 19 hours. The solvent was then removed by distillation under reduced pressure and the resulting concentrate was diluted with deionised water (300 ml). The aqueous solution was then washed with diethyl ether (3×400 ml). To the aqueous phase was then added 1 M hydrochloric acid until the pH was 2. The acidified solution was then extracted with ethyl acetate (3×400 ml) and the combined organic layers were then dried over magnesium sulfate. The solvent was removed by distillation under reduced pressure to give the title compound as an oil (14.7 g, 67.4 mmol, 56% yield); TLC (diethyl ether/heptane 3:7, visualised with Dragendorff's dip) R$_f$ 0.20; $^1$H NMR (300 MHz, CDCl$_3$) δ: 1.48 (s, 9H), 2.16 (dt, 2H), 3.16 (s, 3H), 3.27–3.51 (m, 3H).

f) tert-Butyl 2-(2-methoxyethyl)acrylate

To a solution of the product from stage e) above (20.8 g, 95.3 mmol) in pyridine (170 ml) was added piperidine (1.70 ml, 19.1 mmol), followed by paraformaldehyde (3.89 g, 130 mmol). The resultant mixture was then heated at 63° C. for 3.5 hours. The reaction mixture was then allowed to cool to room temperature and stirred for 19 hours. The solvent was then removed by distillation under reduced pressure. To the concentrate was then added deionised water (250 ml) followed by hydrochloric acid (200 ml of a 2 M solution). The aqueous phase was then extracted with diethyl ether (1×350 ml, followed by 2×400 ml). The combined organic extracts were then washed with hydrochloric acid (400 ml of a 2 M solution) and dried over magnesium sulfate. Removal of the solvent under reduced pressure gave the title compound as an oil. $^1$H NMR (300 MHz, CDCl$_3$) δ: 1.50 (s, 9H), 2.56 (t, 2H), 3.35 (s, 3H), 3.46–3.53 (m, 2H), 5.54 (s, 1H), 6.13 (s, 1H); LRMS (EI): m/z 130 [M−C$_4$H$_8$]$^+$, 113 [M−C$_4$H$_9$O]$^+$.

g) tert-Butyl (2E)-2-(2-methoxyethyl)-3-[(4-methylphenyl)sulfonyl]-2-propenoate

To a stirred solution of para-toluenesulfonyl iodide (J. Chem. Soc. Perkin Trans. 1, 1988, 1029) (11.4 g, 40.2 mmol) in dichloromethane (25.0 ml) was added a solution of the product from stage f) above (5.0 g, 26.8 mmol) in dichloromethane (10 ml) at room temperature under nitrogen. The resultant solution was then stirred for 60 hours. The reaction mixture was then cooled to 0° C. and triethylamine (5.4 g, 53.4 mmol) was then added over a period of 15–20 minutes whilst maintaining the temperature at 0° C. The resultant mixture was then stirred at 0° C. for 0.5 hours before then warming to room temperature and stirring for a further 5 hours. The reaction was then quenched by the addition of deionised water (100 ml) and the layers were then separated. The aqueous phase was then extracted with dichloromethane (100 ml) and the organic extracts were combined and washed with hydrochloric acid (50 ml of a 1 M solution). The organic layer was then washed with aqueous sodium thiosulfate (100 ml of a 5% w/v solution) and then with deionised water (100 ml). The organic layer was then dried over magnesium sulfate and the solvent was removed under reduced pressure to give the crude product as a dark oil (7.5 g, 22.0 mmol, 82% yield). This reaction was repeated twice more using the same conditions and the combined crude products (74.6 g) were then purified by flash chromatography on silica gel using heptane/ethyl acetate (4:1) as the eluent to give the title compound as a white crystalline solid (48.0 g); m.p. (heptane/ethyl acetate) 84–86° C.; TLC (ethyl acetate/heptane 1:4, visualised with UV @ 254 nm) $R_f$ 0.20: $^1$H NMR (300 MHz, CDCl$_3$) δ ppm 1.45 (s, 9H), 2.48 (s, 3H), 3.14 (t, 2H), 3.30 (s, 3H), 3.51 (t, 2H), 7.10 (s, 1H), 7.35 (d, 2H), 7.83 (d, 2H).

h) 1-[(1E)-2-(tert-Butoxycarbonyl)-4-methoxy-1-butenyl]cyclopentane carboxylic acid To a stirred solution of lithium diisopropylamide (64.6 ml of a 2 M solution in THF/heptane/ethyl benzene) in anhydrous THF (200 ml) at 0° C. was added a solution of cyclopentane carboxylic acid (7.0 ml, 58.7 mmol) in anhydrous THF (100 ml) over a period of 10 minutes under nitrogen. The reaction was then allowed to warm to room temperature whilst stirring for 2.5 hours. The resultant slurry was then cooled to 0° C. and zinc chloride (38.2 ml of a 1 M solution in diethyl ether) was then added over a period of 1 minute. The reaction mixture was then stirred for 10 minutes, and to the resultant solution was added a solution of the product from stage g) above (20.0 g, 58.7 mmol) in anhydrous THF (160 ml) over a period of 5 minutes). The reaction mixture was then stirred for 2 hours whilst maintaining the temperature between 0 to 5° C. The reaction was then allowed to warm to room temperature and stirred for 19 hours. The reaction was then quenched by the addition of isopropanol (120 ml) and the mixture was then stirred for 1 hour. The reaction mixture was filtered, and the solid by-products were then washed with THF (10 ml). To the filtrate was then added deionised water (400 ml), aqueous sodium hydroxide (200 of a 1 M solution) and ethyl acetate (600 ml). More deionised water was added (600 ml), and the resultant solid was removed by filtration. The layers were then separated, and to the aqueous phase was then added hydrochloric acid (1 M solution) until the pH was 2. The aqueous phase was then extracted with ethyl acetate (2×700 ml), the organic layers were combined, dried over magnesium sulfate and then the solvent was removed by distillation under reduced pressure to give the crude product as a yellow oil (16.7 g). The product was then purified by flash chromatography on silica gel using dichloromethane/methanol (9:1) as the eluent to give the title compound as a yellow oil (15.2 g, 50.9 mmol, 87% yield); TLC (dichloromethane/methanol 9:1, visualised with UV @ 254 nm) $R_f$ 0.70; $^1$H NMR (300 MHz, CDCl$_3$) δ ppm 1.48 (s, 9H), 1.67–1.90 (m, 6H), 2.37–2.48 (m, 2H), 2.58 (t, 2H), 3.32 (s, 3H), 3.48 (t, 2H), 6.83 (s, 1H); LRMS (ES negative): m/z 253 [M−CO$_2$H]$^−$.

i) Sodium 1-[(1E)-2-(tert-butoxycarbonyl)-4-methoxy-1-butenyl]cyclopentane carboxylate To a stirred solution of the product from stage h) above (15.0 g, 50.3 mmol) in isopropyl acetate (300 ml) was added sodium methoxide (3.0 g, 55.6 mmol). The resultant suspension was then stirred for 19 hours at room temperature. The solid was collected by filtration under vacuum and washed with isopropyl acetate before drying in a vacuum oven at 50° C. for 19 hours to give the title compound as a white solid (10.0 g, 31.2 mmol, 62% yield); m.p. (isopropyl acetate) 195–198° C.; $^1$H NMR (300 MHz, CDCl$_3$) δ ppm 1.48 (s, 9H), 1.51–1.72 (m, 6H), 2.21–2.37 (m, 2H), 2.61 (t, 2H), 3.34 (s, 3H), 3.51 (t, 2H), 6.86 (s, 1H); LRMS (ES negative): m/z 253 [M−CO$_2$Na]$^−$.

Preparation 70

1-[(2R)-3-tert-Butoxy-2-methyl-3-oxopropyl]cyclopentanecarboxylic acid

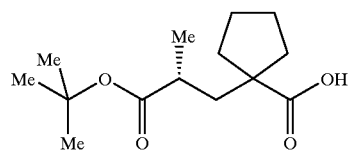

The title compound was prepared according to similar methods to Preparations 68 and 69, using methyl iodide in place of 2-bromoethylmethyl ether. Its (+)-pseudoephedrine salt was recrystalised three times from hexane. The title compound was obtained in 28% yield as a pale yellow oil in >95% ee by NMR analysis of the δ 1.4 peak of the (+)-pseudoephedrine salt; $^1$H NMR (CDCl$_3$ 400 MHz) δ: 1.13 (d, 3H), 1.40–1.60 (m, 11H), 1.60–1.78 (m, 5H), 2.14 (m, 3H), 2.38 (m, 1H); $[α]_D$ −24.2 (EtOH, c 1.2).

Preparation 71

1-[(2R)-2-(tert-Butoxycarbonyl)-4-pentyl]-cyclopentane carboxylic acid

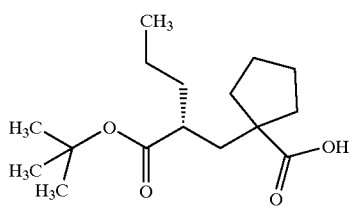

A mixture of (R)-1-[2-(tert-butoxycarbonyl)-4-pentenyl]-cyclopentane carboxylic acid (WO 9113054, Example 10) (10 g, 35.4 mmol) and 10% palladium on charcoal (600 mg) in dry ethanol (25 ml) was hydrogenated at 1 atm. and room temperature for 18 hours. The reaction mixture was filtered through Arbocel®, and the filtrate evaporated under reduced pressure to give the title compound as a yellow oil, 9.6 g, 95%; $^1$H NMR (CDCl$_3$), 0.86 (t, 3H), 1.22–1.58 (m, 15H), 1.64 (m, 4H), 1.78 (dd, 1H), 2.00–2.18 (m, 3H), 2.24 (m, 1H); $[α]_D$=−3.3° (c=0.09, ethanol).

Preparation 72
3-(4-Methoxyphenyl)-2-propenenitrile

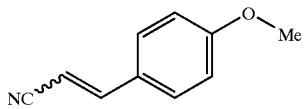

A solution of 4-iodoanisole (1 g, 4.2 mmol), acrylonitrile (0.3 ml, 4.7 mmol), tri-o-tolylphosphine (243 mg, 0.4 mmol), palladium (II) acetate (90 mg, 0.4 mmol) and triethylamine (1.78 ml, 12 mmol) in acetonitrile (20 ml) was refluxed under nitrogen for 14 hours. The reaction mixture was diluted with EtOAc (50 ml) and washed with 2M sodium hydrogen carbonate (100 ml), the organic layer was dried over magnessium sulphate and filtered. The filtrate was evaporated in vacuo and purified by column chromatography using pentane, then 95:5 pentane:ethyl acetate, then 90:10 pentane:ethyl acetate to give the title compound (414 mg, 2.5 mmol) as a mixture of cis and trans isomers as yellow crystals, $^1$H NMR (CDCl$_3$ 400 MHz) δ: 3.8 (s, 3H), 5.7 (d, 1H), 6.9 (d, 1H), 7.2 (d, 1H), 7.4 (d, 2H); LRMS: m/z 176 (M+NH$_4^+$); Anal. Found C, 74.44; H, 5.66; N, 8.36. C$_{10}$H$_{39}$NO.0.1H$_2$O requires C, 74.42; H, 5.65; N, 8.41%.

Preparation 73
3-(4-Methoxyphenyl)-1-propanamine

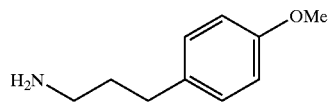

A solution of the product from preparation 72 (414 mg, 2.6 mmol) in ammonium hydroxide solution (10 ml) and ethanol (10 ml) was shaken under hydrogen at 40 p.s.i. with Ra-Ni (100 mg) for 12 hours. The reaction mixture was filtered through arbocel and washed with ethanol (20 ml), the filtrate was evaporated in vacuo to give the title compound (183 mg, 1.1 mmol) as a yellow oil; $^1$H NMR (CDCl$_3$ 400 MHz) δ: 1.7 (bs, 2H), 2.0 (bs, 2H), 2.5 (t, 2H), 2.7 (bs, 2H), 3.7 (s, 3H), 6.7 (d, 2H), 7.0 (d, 2H); LRMS: m/z 376 (M+H$^+$).

The following compounds of formula (IIIa), i.e. compounds of general formula III where X is —(CH$_2$)$_3$—, were prepared by methods similar to those described in Preparations 72 and 73 from the precursors indicated.

TABLE 3

(IIIa)

H$_2$N—⌒⌒—Y

| Prep | Prec | Y | Analytical Data |
|------|------|---|-----------------|
| 74 | 1-bromo-4-ethyl benzene (Aldrich Chemical Co) | 4-ethylphenyl | $^1$H NMR (CD$_3$OD, 400 MHz) δ: 1.1 (bs, 3H), 1.7 (bs, 2H), 2.6 (bs, 5H), 3.4 (bs, 1H), 7.1 (bs, 4H). LRMS: m/z 164 (M + H$^+$). |
| 75 | 4-bromo-3-methyl-anisole (Lancaster) | 4-methoxy-2-methylphenyl | $^1$H NMR (CDCl$_3$, 400 MHz) δ: 1.7 (m, 2H), 2.25 (s, 3H), 2.58 (m, 2H), 2.7 (m, 2H), 3.72 (d, 3H), 6.65 (m, 2H), 7.01 (m, 1H). LRMS: m/z 180 (M + H$^+$). |
| 76 | 5-iodo-2,3-dihydrobenzofuran (Maybridge Chemicals) | 2,3-dihydrobenzofuran-5-yl | $^1$H NMR (CDCl$_3$, 400 MHz) δ: 1.8 (m, 2H), 2.6 (t, 2H), 2.7 (t, 2H), 3.1 (m, 2H), 3.3 (t, 2H), 4.5 (t, 1H), 6.6 (d, 1H), 6.9 (d, 1H), 7.1 (s, 1H). |
| 77 | 2,4-difluoro-iodobenzene (Aldrich Chemical Co.) | 2,4-difluorophenyl | $^1$H NMR (CDCl$_3$, 400 MHz) δ: 1.64 (m, 2H), 2.6 (t, 2H), 2.7 (t, 2H), 6.7 (m, 2H), 7.1 (m, 1H). LRMS: m/z 172.1 (M + H). |
| 78 | 2-bromonaphthalene (Aldrich Chemical Co.) | naphthalen-2-yl | $^1$H NMR (MeOD, 400 MHz) δ: 2.0 (m, 2H), 2.9 (m, 4H), 7.4 (m, 3H), 7.6 (m, 1H), 7.7 (m, 3H). LRMS: m/z (ES$^+$) 186 (M + H). |
| 79 | 1-bromonaphthalene (Aldrich Chemical Co.) | naphthalen-1-yl | $^1$H NMR (CDCl$_3$, 400 MHz) δ: 2.1 (m, 2H), 3.0 (m, 2H), 3.1 (m, 2H), 7.3 (m, 2H), 7.5 (m, 2H), 7.7 (m, 1H), 7.8 (m, 1H). LRMS: m/z (ES$^+$) 186 (M + H). |

TABLE 3-continued (IIIa) H2N~~~Y

| Prep | Prec | Y | Analytical Data |
|---|---|---|---|
| 80 | Prep 114 | 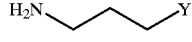 | $^1$H NMR (CDCl$_3$, 400 MHz) δ: 1.78–1.88 (m, 2H), 2.68–2.83 (m, 4H), 7.19–7.36 (m, 3H), 7.70–7.77 (m, 2H), 7.92 (d, 2H), 8.69 (d, 1H). |
| 81 | 3,4-ethylenedioxy-bromobenzene (Lancaster Synthesis) | 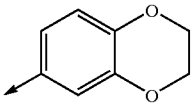 | The crude amine was used with no purification. Data for the cis and trans mixture of vinyl nitriles. $^1$HNMR (300 MHz, CDCl$_3$) δ: 4.25–4.39 (m, 4H), 5.30 and 5.70 (d, 1H), 6.83–7.00 (m, 3H), 7.21–7.40 (m, 1H). |
| 82 | 2-bromoanisole (Lancaster Synthesis) | 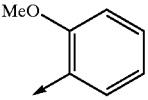 | $^1$H NMR (MeOD, 400 MHz) δ: 1.9 (m, 2H), 2.6 (t, 2H), 2.8 (q, 2H), 3.8 (s, 3H), 6.8 (t, 1H), 6.9 (d, 1H), 7.1 (d, 1H), 7.2 (t, 1H). LRMS: m/z (TS$^+$) 166 (M + H). |
| 83 | 4-bromotoluene (Aldrich Chemical Co.) | 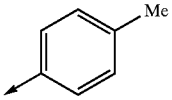 | $^1$H NMR (MeOD, 400 MHz) δ: 1.9 (m, 2H), 2.2 (s, 3H), 2.6 (t, 2H), 2.8 (t, 2H), 7.0 (s, 4H). LRMS: m/z (TS$^+$) 150 (M + H). |
| 84 | 3-iodobenzyloxy-benzene (Aldrich chemical Co.) | 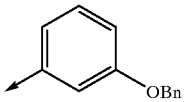 | $^1$H NMR (MeOD, 400 MHz) δ:1.8 (bs, 2H), 2.6 (bm, 4H), 5.0 (bs, 2H), 6.9 (d, 3H), 7.1 (m, 2H), 7.3 (m, 3H). LRMS: m/z (TS$^+$) 242 (M + H). |
| 85 | 3-bromoanisole (Lancaster Synthesis) | 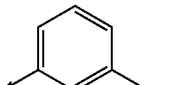 | $^1$H NMR (CDCl$_3$, 400 MHz) δ: 1.7 (m, 2H), 2.6 (t, 2H), 2.7 (t, 2H), 3.8 (d, 3H), 6.3–6.4 (dd, 1H), 6.7 (dd, 1H), 6.9 (d, 1H), 7.1 (m, 1H). |
| 86 | 2,4-dimethoxybromo-benzene (Aldrich Chemical Co.) | 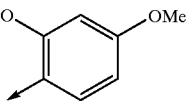 | LRMS: m/z (TS$^+$) 196 (M + H). |
| 87 | 5-Bromo-2,2-dimethyl-2,3-dihydrobenzo[b]furan (Preparation 126) | 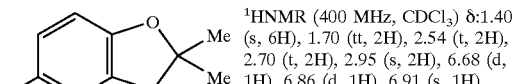 | $^1$HNMR (400 MHz, CDCl$_3$) δ:1.40 (s, 6H), 1.70 (tt, 2H), 2.54 (t, 2H), 2.70 (t, 2H), 2.95 (s, 2H), 6.68 (d, 1H), 6.86 (d, 1H), 6.91 (s, 1H). LRMS: M + H, 206. (TS$^+$). |
| 88 | 6-Bromo-tetrahydrobenzopyran (Preparation 125) | 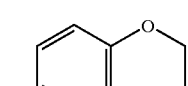 | $^1$HNMR (400 MHz, CDCl$_3$) δ: 1.62–1.78 (m, 2H), 1.84–2.03 (m, 2H), 2.44–2.58 (m, 2H), 2.61–2.78 (m, 4H), 4.03–4.18 (m, 2H), 6.67 (d, 1H), 6.79–6.93 (m, 2H). LRMS: m/z (M + H) 192, ES$^+$. |
| 89 | 5-bromo-2,2-difluoro-benzodioxolane (Fluorochem) | 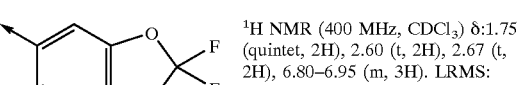 | $^1$H NMR (400 MHz, CDCl$_3$) δ:1.75 (quintet, 2H), 2.60 (t, 2H), 2.67 (t, 2H), 6.80–6.95 (m, 3H). LRMS: M + H, 216. (ES$^+$). |
| 90 | 5-bromo-1-methyl-[1H]-indazole (Preparation 111) | 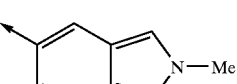 | Used crude with no purification or characterisation. |

TABLE 3-continued (IIIa)

H₂N—⁀—Y

| Prep | Prec | Y | Analytical Data |
|---|---|---|---|
| 90a | 5-Bromo-7-methyl-2,3-dihydrobenzo[b]furan (Preparation 136) | ![structure with Me] | ¹HNMR (400 MHz, CDCl₃) δ: 1.9 (m, 2H), 2.1 (s, 3H), 2.55 (t, 2H), 2.85 (t, 2H), 3.10 (t, 2H), 4.45 (t, 2H), 6.70 (s, 1H), 6.80 (s, 1H). LRMS: M + H, 192 (ES⁺). |
| 91 | 5-Bromo-6-methyl-2,3-dihydrobenzo[b]furan (Preparation 138) | ![structure with Me] | ¹HNMR (400 MHz, CDCl₃) δ: 1.8 (m, 2H), 2.2 (m; 3H), 2.6 (m, 2H), 2.9 (m, 2H), 3.1 (m, 2H), 4.4 (m, 2H), 6.5 (m, 1H), 6.6 (m, 1H). LRMS: M + H, 192 (ES⁺). |
| 92 | 5-Bromo-2-methyl-2,3-dihydro-1-benzo[b]furan (Preparation 127) | ![structure with Me] | ¹HNMR (400 MHz, CDCl₃) 1.45 (d, 3H), 1.90–2.10 (m, 2H), 2.50–2.63 (m, 2H), 2.88 (dd, 1H), 3.27 (dd, 1H), 4.90 (m, 1H), 6.66 (d, 1H), 6.90 (d, 1H), 6.95 (s, 1H). LRMS: M + H, 192. (ES⁺). |

Preparation 93

3-(4-Chloro-3-fluorophenyl)-2-propenenitrile

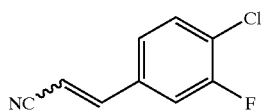

Diethylcyanomethyl phosphonate (3.2 ml, 18.9 mmol) was taken up in dry THF (20 ml) at 0° C. under nitrogen, and stirred as a 60% oil dispersion of NaH (756 mg, 18.9 mmol) was added portionwise over ca. 10 min. The resulting grey suspension was then stirred at 0° C. for 1 h, before a solution of 4-chloro-3-fluoro benzaldehyde (Lancaster Synthesis) (3 g, 18.9 mmol) in 5 ml THF was added dropwise. The whole reaction was then allowed to warm to room temperature over 60 h. Water (5 ml) was added, and the mixture extracted with EtOAc (3×50 ml). The combined organics were were dried (MgSO₄) and evaporated to a yellow oil which was purified by column chromatography using 5% EtOAc in pentane as eluant to provide the title product as a mixture of geometric isomers (2.4 g, 70%); ¹HNMR (400 MHz, CDCl₃) δ: 5.82 (d, 1H), 7.19 (d, 1H), 7.23 (d, 1H), 7.30 (d, 1H), 7.42 (app.t, 1H); LRMS TS⁺ 199.1 (M+NH₄⁺).

Preparation 94

3-(4-Chloro-3-fluorophenyl)-1-propylamine

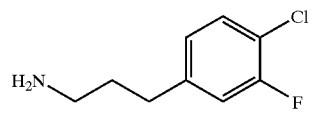

The vinyl cyanide from Preparation 93 (500 mg, 2.75 mmol) was taken up in ethanol (36 ml) and 0.88 NH₃ solution (18 ml) and shaken with 150 mg of 30% w/w RaNi under 15 psi H₂ pressure overnight. The catalyst was filtered through a short plug of Arbocel and the filtrate was evaporated in vacuo and then purified by column chromatography using 90:10:1 (DCM, MeOH, NH₃) as eluant to give the title product (320 mg, 62%);

¹HNMR (400 MHz, CDCl₃), 1.65–1.78 (m, 2H), 2.53–2.70 (m, 4H), 6.85 (d, 1H), 6.90 (d, 1H), 7.22 (s, 1H); LRMS: m/z (TS⁺) 188 (M+H).

The following compounds of formula (IIIa), i.e. compounds of general formula III where X is —(CH₂)₃—, were prepared by methods similar to those described in Preparations 93 and 94 from the precursors indicated.

(IIIa)

H₂N~~~Y

| Prep | Prec. aldehyde | Y | Analytical data |
|---|---|---|---|
| 95 | 3-chloro-4-fluoro benzaldehyde (Lancaster Synthesis) | ![F,Cl-phenyl] | ¹HNMR (400 MHz, CDCl₃) δ:1.62–1.77 (m, 2H), 2.55 (t, 2H), 2.64 (t, 2H), 6.97–6.99 (m, 2H), 7.14 (d, 1H). LRMS: m/z TS⁺188.1 (MH⁺). |
| 96 | 2,3-difluoro benzaldehyde (Lancaster Synthesis) | ![2,3-diF-phenyl] | ¹HNMR (400 MHz, CDCl₃) δ:1.66–1.78 (m, 2H), 2.58–2.75 (m, 4H), 6.83–6.98 (m, 3H). LRMS: m/z TS⁺ 343.1 (2 MH⁺). |
| 97 | 2,6-difluoro benzaldehyde (Lancaster Synthesis) | ![2,6-diF-phenyl] | ¹HNMR (400 MHz, CDCl₃) δ: 1.68–1.83 (m, 2H), 2.57–2.83 (m, 4H), 6.70–6.92 (m, 2H), 7.01–7.22 (m, 1H). LRMS: m/z TS⁺172.1 (MH⁺). |
| 98 | 4-trifluoro-methoxy benzaldehyde (Aldrich Chemical Co. | ![OCF3-phenyl] | ¹HNMR (400 MHz, CDCl₃) δ: 1.70–1.82 (m, 2H), 2.60 (t, 2H), 2.73 (t, 2H), 7.07 (d, 2H), 7.18 (d, 2H). LRMS: m/z ES⁺220 (MH⁺). |
| 99 | Preparation 102 | ![quinoline] | ¹HNMR (400 MHz, CDCl₃) δ: 1.66 (m, 2H), 1.89 (m, 2H), 2.42 (m, 2H), 7.36 (m, 1H), 7.50–7.62 (m, 2H), 8.02 (m, 2H), 8.93 (d, 1H). |
| 100 | 4-(methylthio)-benzaldehyde (Aldrich Chemical Co.) | ![SMe-phenyl] | ¹HNMR (400 MHz, CDCl₃) δ:1.68–1.75 (m, 2H), 1.42 (s, 3H), 2.59 (t, 2H), 2.70 (t, 2H), 7.07 (d, 2H), 7.16 (d, 2H). LRMS: M + H, 182. (TS⁺). |
| 101 | 2,3-dihydrobenzo[b]furan-7-carboxaldehyde (Preparation 128) | ![dihydrobenzofuran] | ¹HNMR (300 MHz, CDCl₃) δ: 1.78 (tt, 2H), 2.64 (t, 2H), 2.73 (t, 2H), 3.22 (t, 2H), 4.55 (t, 2H), 6.78 (dd, 1H), 6.95 (d, 1H), 7.05 (d, 1H). LRMS: M + H, 178. (TS⁺). |

Preparation 102

Quinoline-6-carboxaldehyde

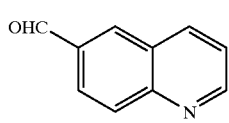

6-Methyl-quinoline (Aldrich Chemical Co.) (1 g, 7.0 mmol) and selenium dioxide (2.32 g, 21.0 mmol) were combined in the absence of solvent and heated at 100° C. under a nitrogen atmosphere for 16 h. The reaction mixture was allowed to cool to room temperature, taken up in MeOH and presorbed onto silica gel. Chromatography using a 3:1 mixture of pentane: EtOAc provided the title product (236 mg, 21%); ¹HNMR (400 MHz, CDCl₃) δ: 7.46–7.52 (m, 2H), 7.98 (d, 1H), 8.33–8.37 (m, 2H), 9.03 (d, 1H), 10.18 (s, 1H); m/z (ES⁺) 315 (2MH⁺).

Preparation 103

4-(4-Methoxyphenyl)-butyramide

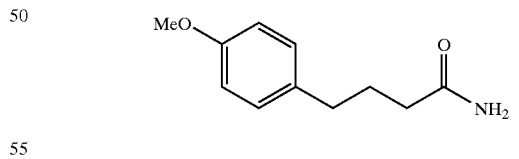

4-(4-Methoxyphenyl)-butyric acid (Aldrich Chemical Co.) (2 g, 10.4 mmol) was dissolved in 50 ml DCM and thionyl chloride (1.85 g, 15.5 mmol) added dropwise with stirring. After the addition was complete, the mixture was then refluxed for 4 h. The solvent was removed in vacuo, more was added and then evaporated off and this cycle of addition/evaporation continued until all the thionyl chloride had been removed from the crude mixture. This mixture was dissolved in 20 ml DCM and added dropwise to a stirred solution of 0.88NH₃ at 0° C. After the addition was complete, the whole was stirred for 4 h, the organic layer separated, dried (Na₂CO₃) and evaporated to give the title product as a white solid of the amide (1.5 g), which was used with no further purification.

Preparation 104
4-(4-Hydroxyphenyl)-butyramine

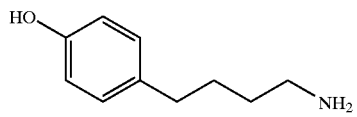

The product from Preparation 103 (38 g, 0.20 moles) was added portionwise to a stirred solution of LiAlH$_4$ (15 g, 0.40 moles) in 1 L of THF, and the whole then refluxed for 16 h. The excess hydride was destroyed by addition of EtOAc (400 ml), and most of the solvents were then removed under reduced pressure. Addition of 30 ml of 2N NaOH solution (CAUTION!) completed the decomposition of the hydride, and the resulting solution was then acidified with 1N HCl and taken up by extraction into water (2×200 ml). Basification of the aqueous extracts with 2N NaOH, extraction with EtOAc, drying (MgSO$_4$) and evaporation led to a yellow oil of crude amine. This oil was refluxed in 160 ml aqueous HBr for 4 h, and was then poured onto 100 ml water. Solid Na$_2$CO$_3$ was then added until a pH of 9–10 was obtained. The mixture was thoroughly extracted with DCM (3×100 ml), dried (MgSO$_4$) and evaporated to a white solid which was recrystallised from benzene to give the title product (6.4 g, 35%); m.p. 114–116° C.

Preparation 105
Tert-Butyl-4-(4-hydroxyphenyl)butylcarbamate

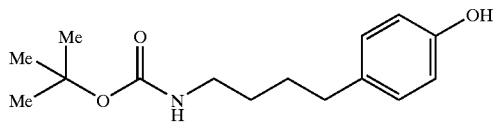

Di-tert-butyl dicarbonate (1.06 g, 4.8 mmol) was added in one portion to a stirred solution of the product from Preparation 104 (400 mg, 2.4 mmol) in a mixture of water (10 ml) and dioxan (10 ml) under nitrogen. The reaction was stirred for 72 h, after which time potassium carbonate (2.0 g, 14.4 mmol) was added in one portion and the mixture stirred for a further 23 h to completely hydrolyse any ester formed during the reaction. The mixture was transferred to a separating funnel, and the organic layer separated, dried over MgSO$_4$ and evaporated to a yellow oil. The oil was chromatographed using a 2:1 mixture of pentane:EtOAc as eluant to give the title product (555 mg, 86%); $^1$HNMR (400 MHz, CDCl$_3$) δ: 1.41–1.62 (m, 13H), 2.53 (t, 2H), 3.12 (m, 2H), 4.48 (1H, brs), 4.80 (s, 1H), 6.74 (d, 2H), 7.01 (d, 2H).

Preparation 106
Tert-Butyl-(4–4-methoxyphenyl)butylcarbamate

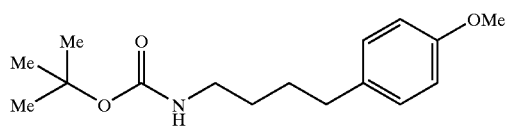

A 60% dispersion of NaH in mineral oil (88 mg, 2.2 mmol) was added to a stirred solution of the product from Preparation 105 (555 mg, 2.1 mmol) in THF (7 ml) at room temperature under nitrogen. The mixture was stirred for 15 min, before adding MeI (0.14 ml, 2.2 mmol) in one portion and stirring at room temperature for a further 16 h. The reaction was diluted with EtOAc (20 ml) and washed with 3% NaHCO$_3$ solution (15 ml). The organic layer was dried over MgSO$_4$ and purified by chromatography using DCM as eluant to provide the title compound (500 mg, 85%); $^1$HNMR (400 MHz, CDCl$_3$) δ: 1.40–1.63 (m, 13H), 2.57 (t, 2H), 3.13 (m, 2H), 3.78 (s, 3H), 4.46 (1H, brs), 6.82 (d, 2H), 7.06 (d, 2H).

Preparation 107
4-(4-Methoxyphenyl)butylamine

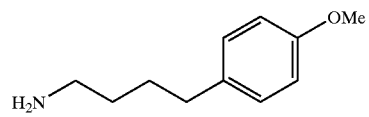

The product from Preparation 106 (500 mg, 1.8 mmol) was taken up in 3 ml of DCM and 3 ml of TFA, and stirred under nitrogen for 16 h. The mixture was then poured onto 50 ml of a 10% aqueous solution of Na$_2$CO$_3$ and the organics extracted with EtOAc (2×50 ml). The combined organic layers were dried (MgSO$_4$) and evaporated to provide the title product (300 mg, 94%), which was used with no further purification.

Preparation 108
3-(2-pyridinyl)-1-propanamine

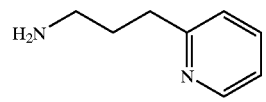

2-Vinyl pyridine (105 g) and acetic anhydride (204 g) were combined at room temperature, and a solution of KCN (130 g) in 250 ml of water was added dropwise to the stirring solution. The rate of addition was adjusted to maintain a gentle reflux. After the addition was complete, the mixture was refluxed for 22 h, and the pH of the solution then adjusted to 8 with aqueous Na$_2$CO$_3$ solution. The mixture was extracted with DCM (600 ml), the extracts dried over MgSO$_4$ and then evaporated to a brown oil. The oil was then vacuum distilled at approximately 0.6 mmHg pressure. The product distilled over as a clear oil at 100–107° C. in 56% yield. The oil of 2-(2-cyanoethyl)-pyridine (200 mg, 1.5 mmol) was taken up in 6 ml of EtOH and treated with 2 ml of 0.88NH$_3$ solution and 50 mg of RaNi. The mixture was hydrogenated at 30 psi H$_2$ pressure for 16 h, and was then filtered and evaporated to give the title product (ca. 200 mg) which was used with no further purification.

Preparation 109
2-Acetyl-2H-indazole

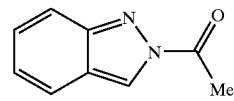

Indazole (3.5 g, 29.6 mmol) and acetic anhydride (35 ml) were heated at 60° C. under nitrogen for 3 h. Excess acetic anhydride was evaporated and the remaining oily residue partitioned between 3% aqueous NaHCO$_3$ (20 ml) and EtOAc (30 ml). The organic layer was separated, dried (MgSO$_4$) and evaporated to provide the title product (4.5 g, 96%); ¹HNMR (400 MHz, CDCl₃) δ: 2.80 (s, 3H), 7.37 (t, 1H), 7.58 (t, 1H), 7.75 (d, 1H), 8.46 (d, 1H).

Preparation 110
5-Bromo-2H-indazole and 5-bromo-1H-indazole

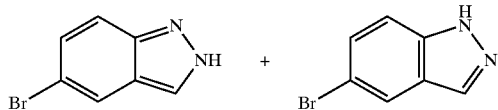

The product from Preparation 109 (450 mg, 2.8 mmol) was taken up in acetic acid (0.5 ml) and stirred at room temperature under nitrogen. Bromine (0.5 ml) was added over about 1 min, and the reaction then stirred for a further 16 h. Excess bromine was removed by bubbling nitrogen gas through the solution for 30 min, whereupon a thick solid was produced in the flask. 5 ml of toluene was added, and the whole evaporated in vacuo and the residue triturated with pentane (5 ml). The remaining solid was filtered off and dried under vacuum before treating with 6 ml each of 1M NaOH and EtOH. The mixture was heated to 50° C. for 1 h and then allowed to cool to room temperature. The EtOH was evaporated, and the residue extracted with DCM (2×10 ml), which was then dried (MgSO₄) and evaporated to give 400 mg of a 3:1 inseparable mixture of the title 1-H:2-H indazole isomers; ¹HNMR (400 MHz, CDCl₃) δ: 7.41 (d, 1H), 7.49 (d, 1H), 7.92 (s, 1H), 8.02 (s, 1H).

Preparation 111
2-Methyl-5-bromo-2H-indazole and 1-Methyl-5-bromo-1H-indazole

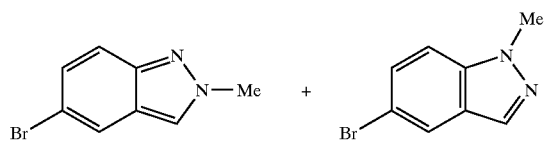

The mixture of isomers from Preparation 110 (400 mg, 2.0 mmol) was taken up in MeOH (8 ml) at room temperature under nitrogen and NaOMe (223 mg, 4.0 mmol) added in one portion. MeI (0.32 ml, 5 mmol) was added dropwise and the mixture heated at reflux for 4 h. The reaction was allowed to cool to room temperature and then concentrated to low volume (ca. 3 ml) before partitioning between EtOAc (20 ml) and 3% aqueous NaHCO₃ solution. The organic layer was separated, dried (MgSO₄) and purified by chromatography using 99:1 DCM:MeOH as eluant to provide the 1-Me isomer (100 mg, 23%) and the 2-Me isomer and (112 mg, 26%); 1-Methyl isomer; ¹HNMR (400 MHz, CDCl₃) δ: 4.08 (s, 3H), 7.30–7.50 (m, 2H), 7.82 (s, 1H), 7.92 (s, 1H); 2-Methyl isomer; ¹HNMR (400 MHz, CDCl₃) δ: 4.13 (s, 3H), 7.35 (d, 1H), 7.59 (d, 1H), 7.81 (s, 1H), 7.85 (s, 1H).

Preparation 112
3-(1-Methyl-1H-indazol-5-yl)-2-propenenitrile

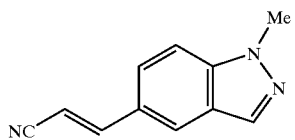

The 1-methyl isomer from Preparation 111 (100 mg, 0.47 mmol) was taken up in dioxan (6 ml), and potassium carbonate (72 mg, 0.52 mmol), acrylonitrile (0.035 ml, 0.52 mmol), Pd₂(dba)₃ (43 mg, 0.047 mmol) and PtertBu₃ (0.038 ml, 0.16 mmol) were added in sequence. The reaction was then refluxed for 3 h under a nitrogen atmosphere before cooling to room temperature, filtering through a short plug of arbocel and evaporation of the filtrate in vacuo. The residue was then chromatographed using 99:1 DCM:MeOH to give the title product (57 mg, 66%) as a mixture of cis and trans geometric isomers; ¹HNMR (300 MHz, CDCl₃) δ: 4.11 (s, 3H), 5.40 and 5.84 (d, 1H), 7.37–8.18 (m, 5H).

Preparation 113

3-(1-Methyl-1H-indazol-5-yl)-1-propanamine

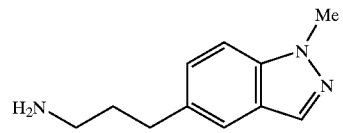

The product from Preparation 112 (55 mg, 0.29 mmol) was taken up in ethanol (4 ml) and 0.88NH₃ solution (1 ml) and subjected to hydrogenation at 30 psi and room temperature under 10 mg of 30% w/w RaNi for 2 h. The mixture was filtered through a short plug of Arbocel and the filtrate evaporated to give the title product which was used with no further purification.

Preparation 114

2-(4-Bromophenyl)-pyridine

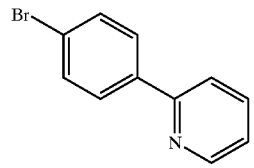

ⁿBuLi (1.6M in hexanes, 34.4 mls, 55 mmol) was added dropwise to a stirred solution of 1,4-dibromobenzene (11.8 g, 50 mmol) in 100 ml of dry THF at −60° C. The mixture was stirred for 15 min at this temperature before a solution of ZnCl₂ (0.5M in THF, 100 ml, 50 mmol) in THF was added dropwise. The mixture was allowed to warm to room temperature over 90 min, and then Pd(PPh₃)₄ (200 mg) was added, followed immediately by 2-bromopyridine (4.8 ml, 50 mmol). The whole was stirred at room temperature overnight, then evaporated to low (10 ml) volume and diluted with EtOAc (400 ml). The solution was washed with a solution of 32 g of EDTA in 200 ml water and brine (200 ml), dried (MgSO₄) and evaporated to a yellow/green solid. This solid was purified by column chromatography using 1:1 hexane:DCM as eluant to provide the title product (8.3 g; 71%); m/z MH⁺ 234 (TS⁺); Found C, 56.61%, H, 3.37%, N, 5.90%; Calcd. C, 56.44%, H, 3.44%, N, 5.98%.

Preparation 115
3-(2,3-Dihydro-1H-inden-5-yl)-pronanoic acid

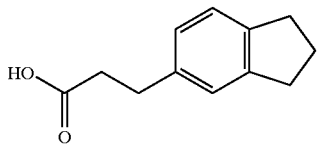

3-(2,3-Dihydro-1H-inden-5-yl)-propenoic acid (500 mg, 2.66 mmol) (available from Aldrich) was taken up in ethanol (40 ml) and hydrogenated at 15 psi $H_2$ pressure with 40 mg of 10% Pd/C for 4 h. The mixture was filtered through a short plug of Arbocel and the filtrate evaporated to give the title product (560 mg, approx. quantitative) which was used with no further purification; $^1$HNMR (400 MHz, $CDCl_3$) δ: 1.98–2.07 (m, 2H), 2.75 (t, 2H), 2.80–2.90 (m, 6H), 6.95 (d, 1H), 7.03 (s, 1H), 7.08 (d, 1H); LRMS: m/z ES$^-$189 (M–H).

Preparation 116
3-(2,3-Dihydro-1H-inden-5-yl)-propanamide

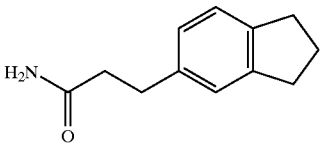

The product from preparation 115 (190 mg, 1 mmol) was dissolved in DCM (2 ml) at room temperature under nitrogen, and firstly 132 μl (1.5 mmol) of oxalyl chloride, and then 1 drop of DMF were added. After the effervescence had subsided, the mixture was stirred at room temperature for 3 h and then concentrated in vacuo. The residue was redissolved in 2 ml of THF and 0.6 ml of 0.88$NH_3$ solution added, and the whole stirred for 4 days. The reaction was quenched with water and extracted into EtOAc (2×10 ml). The combined organics were dried ($MgSO_4$) and evaporated to give the title product (190 mg, 99%); $^1$HNMR (400 MHz, $CDCl_3$) δ: 1.96–2.05 (m, 2H), 2.49 (t, 2H), 2.81–2.92 (m, 6H), 5.32 (brs, 2H), 6.93 (d, 1H), 7.05 (s, 1H), 7.08 (d, 1H); LRMS: m/z (ES$^-$) 189 (M–H).

Preparation 117
3-(2,3-Dihydro-1H-inden-5-yl)-propylamine

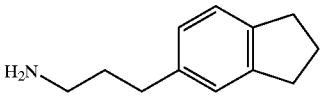

The amide from Preparation 116 (170 mg, 0.9 mmol) was dissolved in dry THF (3 ml) at 0° C. under nitrogen and stirred as a solution of $LiAlH_4$ in THF (1M, 0.9 ml, 0.9 mmol) was added dropwise with considerable effervescence. The reaction was warmed to 60° C. and stirred at this temperature overnight. The mixture was quenched with water (1 ml), 1N NaOH solution was added (1 ml) and the solution extracted with EtOAc (2×50 ml), dried ($MgSO_4$), filtered and concentrated to a pale yellow oil. This oil was purified by column chromatography using 90:10:1 (DCM, MeOH, $NH_3$) as eluant to give the title product (30 mg, 35%); $^1$HNMR (400 MHz, $CDCl_3$) δ: 1.72–1.77 (m, 2H), 1.96–2.03 (m, 4H), 2.57 (t, 2H), 2.70 (t, 2H), 2.80–2.85 (m, 4H), 6.90 (d, 1H), 7.02 (s, 1H), 7.09 (d, 1H); LRMS: m/z (TS$^+$) 176 (M+H).

Preparation 118
3-(4-Bromophenyl)-2-propenenitrile

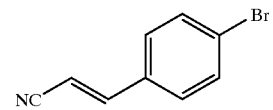

A 60% suspension of NaH in mineral oil (2.16 g, 54.1 mmol) was suspended in THF (50 ml) and cooled to 0° C. under nitrogen. Diethyl-cyanomethyl phosphonate (8.74 ml, 54.1 mmol) was added dropwise and the whole stirred at 0° C. for 30 min. 4-bromobenzaldehyde (10 g, 54.1 mmol) was then added dropwise as a solution in 20 ml THF, and the mixture allowed to warm to room temperature overnight. The reaction was quenched with water, extracted with EtOAc (3×50 ml), dried ($MgSO_4$) and then filtered and evaporated to a yellow oil. This oil was taken up in a 9:1 mixture of pentane:EtOAc from which the title product crystallised (5.8 g, 52%); $^1$HNMR (400 MHz, $CDCl_3$) δ: 5.82 (d, 1H), 7.21–7.28 (m, 3H), 7.50 (d, 2H).

Preparation 119
3-(4-Bromophenyl)-1-propanamine

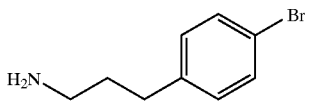

The title compound was prepared by a modified procedure of that described by Iddon et al. (*J. C. S. Perkin I*, 1977, 2357). Solid $LiAlH_4$ (1.2 g, 31.6 mmol) was suspended in diethyl ether (35 ml) and stirred under nitrogen as the suspension was heated to ca. 50° C. A solution of the vinyl cyanide from Preparation 118 (2.06 g, 9.88 mmol) was added dropwise as a solution in ether (20 ml) and the mixture then heated for 90 min. After this time, the heating was stopped, and the reaction was stirred at room temperature for 16 h. Water was added, followed by 1N NaOH (30 ml) and EtOAc (60 ml) and the whole stirred vigorously for 30 min. The organic layer was separated, dried ($MgSO_4$) and evaporated to a yellow oil which was purified by column chromatography using 90:10:1 (DCM, MeOH, $NH_3$) as eluant to provide the title product (740 mg, 35%); $^1$HNMR (400 MHz, $CDCl_3$) δ: 1.65–1.74 (m, 2H), 2.52 (t, 2H), 2.66 (t, 2H), 7.02 (d, 2H), 7.35 (d, 2H); LRMS: m/z (TS$^+$) 214 (M+H).

Preparation 120
1-(2-Chlorophenoxy)-2-propanamine

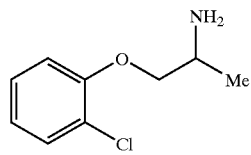

The product from preparation 121 (11 g, 55.2 mmol) in diethyl ether (41 ml) was added dropwise to a suspension of lithium aluminium hydride (4.1 g, 108 mmol) in diethyl ether (110 ml) under nitrogen. The reaction mixture was refluxed for 4 hours before the addition of ethyl acetate then water. The aqueous layer was acidified with 4N hydrochloric acid shaken and then separated before been made alkaline with 40% sodium hydroxide solution. The aqueous layer was then extracted with diethyl ether (3×100 ml) and the combined organic extracts were dried over magnesium sulphate. The diethyl ether extracts were acidified with hydrogen chloride and the resulting precipitate filtered. The solid was recrystallised from ethanol/petroleum ether (b.p. 60–80 degC.) to give the title product (2.5 g, 20%), m.p. 126–127° C.; $^1$H NMR (CDCl$_3$ 400 MHz) δ: 1.55 (d, 3H), 3.80 (q, 1H), 4.20 (d, 2H), 6.90–7.00 (m, 2H), 7.15 (t, 1H), 7.30 (d, 1), 8.60 (bs, 3H); Anal. Found C, 48.9; H, 6.0; N, 6.5. C$_9$H$_{13}$NOCl$_2$ requires C, 48.7; H, 5.9; N, 6.3%.

Preparation 121
1-(2-Chlorophenoxy)-2-propanone oxime

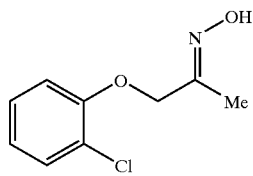

1-(2-Chlorophenoxy)acetone (106.6 g, 0.58 mol) (*J. Am. Chem. Soc.*, 75, 1953, 1134) was added to a solution of hydroxylamine hydrochloride (27.8 g, 4 mol) in 2N sodium hydroxide solution (420 ml) and sufficient ethanol to give a clear solution. The reaction mixture was refluxed for 30 minutes then concentrated in vacuo, the crude residue was extracted with diethyl ether (3×200 ml). The combined organic layers were dried over magnesium sulphate and concentrated in vacuo. The residue was distilled to give the title product (134–136° C./1.35 mmHg) (4.5 g, 3.9%); $^1$H NMR (CDCl$_3$ 400 MHz) δ: 2.05 (s, 3H), 5.00 (s, 2H), 6.90–7.00 (m, 2H), 7.10 (t, 1H), 7.30 (d, 1H), 7.60 (s, 1H). Anal. Found C, 54.95; H, 5.05. C$_9$H$_{10}$NO$_2$Cl requires C, 54.15; H, 5.05%.

Preparation 122
3-(4-Methoxy-3-chlorophenyl)-1-propylamine

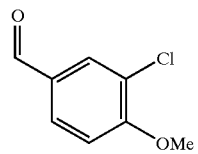

4-Methoxy-benzaldehyde (Aldrich) (42 g, 0.31 mole) and pyridine (0.6 ml, catalytic) were stirred together under nitrogen and sulfuryl chloride (51 g, 0.37 mole) added over 30 min, maintaining the internal temperature of the reaction at between 25 and 30° C. There was a vigorous evolution of gas. The mixture was stirred at room temperature for a further 30 min, and then warmed to 70° C. for 4 h. Excess reagents were removed by evaporation in vacuo and the residue taken up in 50 ml diisopropyl ether and poured onto 500 ml hexane with vigorous stirring, from which the product precipitates. The solid was filtered off and washed with hexane and then dried in vacuo to give the title product (40.3 g, 77%), m.p. 55–56° C.; $^1$HNMR (400 MHz, CDCl$_3$) δ: 3.99 (s, 3H), 7.05 (dd, 1H), 7.91 (d, 1H), 9.86 (s, 1H); Anal. Found: C, 56.13; H, 4.14%. C$_8$H$_7$ClO$_2$ requires C, 56.33; H, 4.14%.

Preparation 123
3-(4-Methoxy-3-chlorophenyl)-1-propylamine

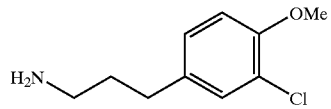

The product from Preparation 122 was converted to a diastereomeric mixture of the corresponding vinyl nitriles according to Preparation 93. This mixture (300 mg, 1.55 mmol) was taken up in DCM (6 ml) at room temperature under nitrogen and tetra-"butyl-ammonium borohydride (1.6 g, 6.2 mmol) added portionwise over 5 min. The mixture was then refluxed for 4 h and then evaporated to dryness. The residue was taken up in approx. 6 ml of 10% HCl (aq.) and then refluxed for a further 1 h. The reaction was cooled, extracted with EtOAc (3×30 ml), dried (MgSO$_4$) and evaporated to a yellow oil. This oil was columned in 95/5/0.5, then 95/5/1 DCM/MeOH/NH$_3$ to give the title product (75 mg, 24%); $^1$HNMR (400 MHz, CDCl$_3$) δ: 1.60–1.74 (m, 2H), 2.56 (t, 2H), 2.67 (t, 2H), 3.82 (s, 3H), 6.79 (d, 1H), 6.98 (d, 1H), 7.15 (s, 1H).

Preparation 124
Chroman

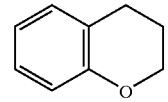

4-Chromanol (Aldrich) (2.77 g, 18.4 mmol) was taken up in acetic anhydride (3.5 ml, 36.9 mmol) and acetic acid (30 ml) and refluxed for 3 h, and then allowed to cool to room temperature over 16 h. 10% w/w Pd/C was then added to the solution and the whole hydrogenated at 40 p.s.i. hydrogen pressure for 16 h. The catalyst was filtered through a pad of Arbocel and the filtrate evaporated to low (5 ml) volume. The remaining liquid was dissolved in EtOAc (30 ml) and washed with water, then NaHCO$_3$ solution (100 ml of each). The organic layer was dried over MgSO$_4$ and evaporated to a pale yellow oil. This oil was columned in 10% EtOAc/pentane to give the title product (2.1 g, 85%);
$^1$HNMR (400 MHz, CDCl$_3$) δ: 1.93–2.04 (m, 2H), 2.79 (t, 2H), 4.18 (t, 2H), 6.78–6.83 (m, 2H), 7.00–7.10 (m, 2H).

Preparation 125
6-Bromochroman

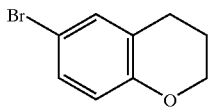

The product from Preparation 124 (1 g, 7.5 mmol) was taken up in DCM (10 ml) and bromine (403 µl, 7.8 mmol) was added as a solution in DCM (3 ml) over several minutes. Towards the end of the addition, a brown colour persisted in the solution. The mixture was stirred at room temperature for 3 h and then washed with water (20 ml) and brine (20 ml) and the organic layer separated, dried (MgSO$_4$) and evaporated to a thick yellow oil, which was purified by column chromatography using 5% EtOAc in pentane to give the title product (1.3 g, 82%); $^1$HNMR (400 MHz, CDCl$_3$) δ: 1.90–1.98 (m, 2H), 2.73 (t, 2H), 4.14 (t, 2H), 6.61 (d, 1H), 7.08–7.15 (m, 2H).

Preparation 126

5-Bromo-2,2-dimethyl-2,3-dihydrobenzo[b]furan

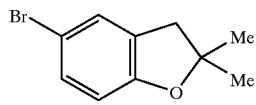

2,2-Dimethyl-2,3-dihydrobenzo[b]furan (prepared according to the method of Baker and Shulgin, *J. Org. Chem.*, 28, 1963, 2468) (500 mg, 3.38 mmol) was taken up in dichloroethane (5.5 ml) and stirred at room temperature under nitrogen, and N-bromosuccinimide (661 mg, 3.72 mmol) added in one portion. The reaction was then refluxed for 2 h, ether was added (10 ml) and a white precipitate of succinimide filtered off. The filtrate was evaporated to dryness, and then purified by column chromatography using 5% ether in pentane as eluant to give the title product (604 mg, 79%); $^1$HNMR (400 MHz, CDCl$_3$) δ: 1.43 (s, 6H), 2.92 (s, 2H), 6.54 (d, 1H), 7.16 (d, 1H), 7.19 (s, 1H); LRMS: M+H, 227. (TS$^+$).

Preparation 127

5-Bromo-2-methyl-2,3-dihydro-1-benzo[b]furan

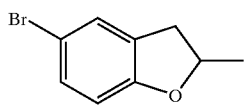

The title product was prepared from 2-methyl-2,3-dihydro-1-benzo[b]furan (commercially available from TCI, Japan) using an identical procedure to that used for Preparation 126 (87%); $^1$HNMR (400 MHz, CDCl$_3$) δ: 1.43 (d, 3H), 2.80 (dd, 1H), 3.29 (dd, 1H), 4.94 (m, 1H), 6.61 (d, 1H), 7.18 (d, 1H), 7.22 (s, 1H).

Preparation 128

2,3-Dihydrobenzo[b]furan-7-carboxaldehyde

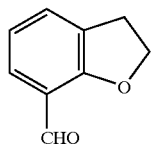

2,3-Dihydrobenzo[b]furan (Maybridge Chemicals) (25 g, 0.21 mole) was taken up in DCM (500 ml) and stirred under nitrogen at 0° C. SnCl$_4$ (36.5 ml, 0.3 mole) was added in one portion to produce a pale yellow solution. Dichloromethyl methyl ether (18.8 ml, 0.21 mole) was then added and the solution stirred for 30 min, after which time the cooling bath was removed and the reaction poured onto ice-water (1000 ml). The organic layer was separated, washed with water (2×100 ml), 2N HCl (100 ml) and brine (50 ml), and then charcoal (30 g) and Na$_2$SO$_4$ were added to the solution. Filtration through Celite and evaporation gave a black oil, which was subjected to flash chromatography using 7–10% EtOAc in pentane to give the title product (190 mg, 0.01%); $^1$HNMR (400 MHz, CDCl$_3$) δ: 3.24 (t, 2H), 4.75 (t, 2H), 6.93 (t, 1H), 7.40 (d, 1H), 7.59 (d, 1H), 10.2 (s, 1H); LRMS: (M+H) 149, TS$^+$. Anal. Found: C, 72.98; H, 5.46%. C$_9$H$_8$O$_2$ requires C, 72.96; H, 5.44%.

Preparation 129

1-Benzofuran-3-ylacetonitrile

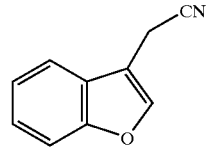

Sodium hydride (268 mg, 6.7 mmol) was slurried in dry THF (10 ml) at 0° C. under nitrogen and diethyl cyanomethyl phosphonate (1.1 ml, 6.7 mmol) added dropwise and the whole stirred for 45 min. 3-Coumaranone (Lancaster) (900 mg, 6.7 mmol) was then added dropwise and the whole stirred at room temperature for 45 min. The reaction was diluted with EtOAc (15 ml) and water (15 ml), and the organic layer was then separated, dried (MgSO$_4$) and evaporated and the residue flash chromatographed using 0–5% EtOAc in pentane to give the title product (940 mg, 91%); $^1$HNMR (400 MHz, CDCl$_3$) δ: 3.77 (s, 2H), 7.25–7.40 (m, 2H), 7.52 (dd, 1H), 7.58 (dd, 1H), 7.67 (s, 1H); LRMS: M+NH$_4^+$, 175. (TS$^+$).

Preparation 130

2-(1-Benzofuran-3-yl)-ethylamine

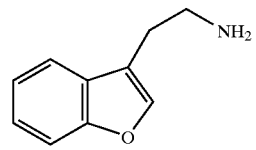

The product from Preparation 129 (400 mg, 2.55 mmol) was combined with ammonium hydroxide solution (10 ml), ethanol (20 ml) and 30 wt % Ra-Ni (120 mg, cat.) and hydrogenated at 30 p.s.i. hydrogen pressure at room temperature for 16 h. The catalyst was filtered through a plug of Arbocel and the yellow-brown filtrate chromatographed using 0–5% MeOH in DCM to provide the title product (380 mg, 93%); $^1$HNMR (400 MHz, CDCl$_3$) δ: 1.20 (brs., 2H), 2.80 (t, 2H), 3.02 (t, 2H), 7.15–7.25 (m, 2H), 7.43 (dd, 2H), 7.55 (dd, 1H); LRMS: M+H, 162. (ES$^+$).

Preparation 131

2-(2,3-Dihydro-1-benzofuran-3-yl)-ethylamine

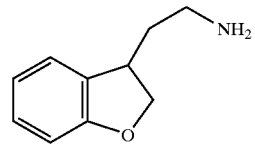

The product from Preparation 130 (200 mg, 1.24 mmol) was mixed with ethanol (20 ml) and 20 mg of 10 wt % Pd/C and hydrogenated at 40 p.s.i. hydrogen pressure for 48 h. A further 20 mg of catalyst was added, and the whole hydrogenated at 60 p.s.i. and 40° C. for a further 72 h. The catalyst was filtered through a short plug of Arbocel, and the filtrate evaporated to dryness. The residue was purified by column chromatography using 90/10/1 DCM/MeOH/NH$_3$ as eluant to provide the title product (11 mg, 55%);
$^1$HNMR (400 MHz, CDCl$_3$) δ: 1.81 (m, 1H), 1.98 (m, 1H), 2.75–2.83 (m, 2H), 3.50 (m, 1H), 4.22 (t, 1H), 4.60 (t, 1H), 6.72 (d, 1H), 6.85 (t, 1H), 7.10 (t, 1H), 7.20 (d, 1H); LRMS: M+H, 164. (ES$^+$).

Preparation 132
(2E and 2Z)-3-(2,3-Dihydro-1-benzofuran-5-yl)-2-butenenitrile

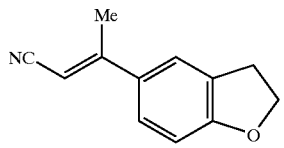

To a stirred suspension of sodium hydride (247 mg, 6.16 mmol) in dry THF (6 ml) at 0° C. under nitrogen was added a solution of diethylcyanomethyl phosphonate (0.98 ml, 6.16 mmol) in 2 ml THF and the whole stirred at 0° C. for 1 h. 5-Acetyl-2,3-dihydro[b]benzofuran (Aldrich) (1 g, 6.16 mmol) in THF (2 ml) was added dropwise and the whole stirred at room temperature for 16 h. Water (20 ml) and EtOAc (20 ml) were added, the organic layer separated, and the aqueous layer extracted with EtOAc (2×20 ml). The combined organics were dried over MgSO$_4$, filtered and evaporated to afford a pale brown oil which solidified on standing. This solid was purified by column chromatography using 20–30% EtOAc in pentane as eluant to give the title product (789 mg, 69%); $^1$HNMR (400 MHz, CDCl$_3$) δ: 2.4 (s, 3H), 3.2 (t, 2H), 4.6 (t, 2H), 5.5 (s, 1H), 6.7 (d, 1H), 7.2 (d, 1H), 7.3 (s, 1H); LRMS: M+NH$_4$ 203 (ES$^+$).

Preparation 133
3-(2,3-Dihydro-1-benzofuran-5-yl)-butylamine

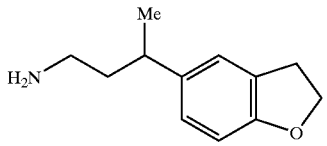

The product from Preparation 132 was dissolved in ethanol (20 ml) and ammonium hydroxide solution (5 ml), and the whole hydrogenated at 30 p.s.i. hydrogen pressure over 200 mg of 30 wt % Ra-Ni for 16 h. A further 100 mg of catalyst was then added and the hydrogenation continued for a further 16 h. The reaction mixture was filtered through a short plug of Arbocel, and the filtrate evaporated in vacuo to low volume. The residue was then co-evaporated from toluene (2×20 ml) to remove last traces of water to provide the title product (780 mg, 96%), which was used with no further purification;
$^1$HNMR (400 MHz, CDCl$_3$) δ: 1.2 (d, 3H), 1.7 (q, 2H), 2.5 (m, 2H), 2.65 (m, 1H), 3.1 (t, 2H), 4.45 (t, 2H), 6.6 (d, 1H), 6.9 (d, 1H), 7.0 (s, 1H; LRMS: M+H 192. (ES$^+$).

Preparation 134
7-Methyl-2,3-dihydro-1-benzofuran-3-ol

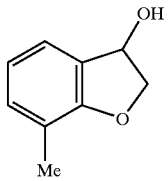

To a stirred suspension of trimethyl sulfoxonium chloride (3.78 g, 0.03 mole) in dry THF (60 ml) was added sodium hydride (1.16 g, 0.03 mole) and the whole warmed to reflux for 1 h. 2-Hydroxy-3-methyl-benzaldehyde (Lancaster) (4 g, 0.03 mole) was added in 30 ml THF via syringe and the resulting orange suspension stirred at reflux for 5 h. Water (50 ml) was added, and the organics were extracted with ether (3×50 ml). The combined organics were dried (MgSO$_4$), filtered and evaporated in vacuo to an orange oil which was purified by column chromatography using 15–25% EtOAc in pentane to give the title product (2 g, 45%); $^1$HNMR (400 MHz, CDCl$_3$) δ: 2.2 (s, 3H), 4.45 (m, 2H), 5.3 (m, 1H), 6.8 (t, 1H), 7.1 (d, 1H), 7.2 (d, 1H); LRMS: M+H, 151. (ES$^+$).

Preparation 135
7-Methyl-2,3-Dihydro-1-benzofuran

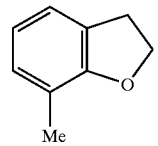

To a stirred solution of the product from Preparation 134 (500 mg, 3.3 mmol) in acetic acid (5 ml) was added acetic anhydride (0.63 ml, 6.7 mmol) and the whole stirred at reflux under nitrogen for 2 h, then allowed to warm to room temperature over 16 h. 10 wt % Pd/C (30 mg) was added directly to the solution and hydrogenated at 40 p.s.i. hydrogen pressure for 16 h at room temperature. The catalyst was filtered through a plug of Arbocel and the filtrate concentrated in vacuo to a pale yellow residue, which was dissolved in EtOAc (20 ml), washed with water (3×20 ml), NaHCO$_3$ (20 ml), dried (MgSO$_4$) and evaporated to a pale yellow oil. This oil was purified by column chromatography using 3% EtOAc in pentane as eluant to provide the title product (261 mg, 58%); $^1$HNMR (400 MHz, CDCl$_3$) δ: 2.2 (s, 3H), 3.2 (t, 2H), 4.55 (t, 2H), 6.75 (t, 1H), 6.9 (d, 1H), 7.05 (d, 1H).

Preparation 136
5-Bromo-7-methyl-2,3-dihydro-1-benzofuran

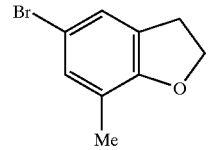

To a stirred solution of the product from Preparation 135 (200 mg, 1.49 mmol) in dichloroethane (2.5 ml) was added N-bromosuccinimide (318 mg, 1.79 mmol) and the whole stirred at reflux for 16 h under nitrogen. The mixture was concentrated in vacuo to afford a pale orange-brown solid which was purified by column chromatography using 1% EtOAc in pentane as eluant to afford the title product (112 mg, 35%); $^1$HNMR (400 MHz, CDCl$_3$) δ: 2.1 (s, 3H), 3.15 (t, 2H), 4.5 (t, 2H), 7.0 (s, 1H), 7.1 (s, 1H).

Preparation 137
2-Hydroxy-4-methyl-benzaldehyde

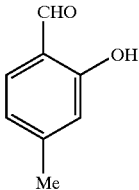

To a stirred solution of 3-methyl-phenol (1 g, 9.2 mmol) in toluene (5 ml) at room temperature under nitrogen was added SnCl$_4$ (241 mg, 0.92 mmol) and tri-$^n$butylamine (0.6 ml, 2.77 mmol). After 20 min, paraformaldehyde (611 mg, 20.3 mmol) was added and the whole stirred at 100° C. for 16 h. The reaction mixture was diluted with water (20 ml) and acidified with 2N HCl to pH2. The solution was extracted with ether (25 ml), washed with brine (20 ml), dried (MgSO$_4$) filtered and evaporated to a brown oil. This oil was purified by column chromatography using 5% EtOAc in pentane as eluant to provide the title product (319 mg, 25%); $^1$HNMR (400 MHz, CDCl$_3$) δ: 2.3 (s, 3H), 6.75 (m, 2H), 7.35 (d, 1H), 9.75 (s, 1H), 11.00 (s, 1H).

Preparation 138
5-Bromo-6-methyl-2,3-dihydrobenzofuran

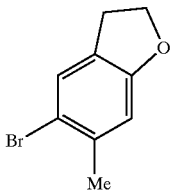

The product from Preparation 137 was taken through to the title compound by an identical 3-step sequence as detailed in Preparations 134–136; $^1$HNMR (400 MHz, CDCl$_3$) δ: 2.3 (s, 3H), 3.55 (t, 2H), 4.5 (t, 2H), 6.7 (s, 1H), 7.3 (s, 1H); LRMS: M+H, 214. (ES$^+$).

Preparation 139
(3E)-4-(2,3-Dihydro-1-benzofuran-5-yl)-3-buten-2-one

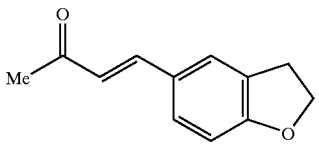

2,3-Dihydrobenzo[b]furan-5-carboxaldehyde (Aldrich Chemicals) (2 g, 13.5 mmol), acetone (2.73 ml, 37.1 mmol), water (1.35 ml) and 10% NaOH (aq.) (0.34 ml) were added together and the whole stirred at room temperature for 16 h. The yellow solid was redissolved in approx. 15 ml DCM and 2N HCl added to achieve a solution of pH2. Water (10 ml) was added and the organic layer was extracted with DCM (2×20 ml). The aqueous layers were separated, and re-extracted with DCM (2×15 ml). The combined organics were dried (MgSO$_4$) and concentrated in vacuo to a yellow solid which was purified by column chromatography using 15–30% EtOAc in pentane as eluant to provide the title product (2.13 g, 84%); $^1$HNMR (400 MHz, CDCl$_3$) δ: 2.3 (s, 3H), 3.2 (t, 2H), 4.6 (t, 2H), 6.5 (d, 1H), 6.75 (d, 1H), 7.3 (d, 1H), 7.4 (s, 1H), 7.45 (d, 1H); LRMS: M+H, 189. (ES$^+$).

Preparation 140
4-(2,3-Dihydro-1-benzofuran-5-yl)-2-butanone

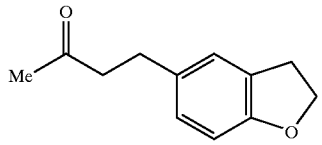

The product from Preparation 139 (2.12 g, 11.3 mmol) was taken up in ethanol (40 ml) and hydrogenated at 15 p.s.i. hydrogen pressure over 200 mg 10 wt % Pd/C for 4 h. The mixture was filtered through a short plug of Arbocel and the filtrate evaporated in vacuo to a colourless oil which was purified by column chromatography using 15–25% EtOAc in pentane to provide the title product (1.53 g, 71%); $^1$HNMR (400 MHz, CDCl$_3$) δ: 2.1, (s, 3H), 2.7 (t, 2H), 2.8 (t, 2H), 3.1 (t, 2H), 4.5 (t, 2H), 6.65 (d, 1H), 6.9 (d, 1H), 7.0 (s, 1H); LRMS: M+NH$_4$, 208. (ES$^+$).

Preparation 141
4-(2,3-Dihydro-1-benzofuran-5-yl)-2-butanamine

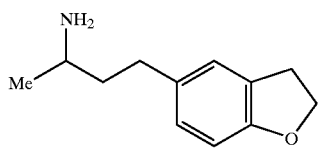

To a stirred solution of the product from Preparation 140 (500 mg, 2.6 mmol) in methanol (25 ml) was added ammonium acetate (4.05 g, 52.6 mmol) and sodium cyanoborohydride (661 mg, 10.5 mmol) and the whole was stirred at room temperature overnight. The reaction mixture was concentrated in vacuo and then partitioned between EtOAc (20 ml) and water (20 ml). The organics were extracted and washed with water (2×20 ml), dried (MgSO$_4$) and evaporated to a clear oil. This oil was purified by column chromatography using 5% MeOH in DCM as eluant to give the title product (187 mg, 37%); $^1$HNMR (400 MHz, CDCl$_3$) δ: 1.3 (d, 3H), 1.8 (m, 2H), 2.6 (m, 2H), 3.1 (t, 2H), 3.2 (m, 1H), 4.45 (t, 2H), 6.6 (d, 1H), 6.9 (d, 1H), 7.05 (s, 1H); LRMS: M+H, 192. (ES$^+$).

Preparation 142
Methyl-(2E)-2-cyano-3-(2,3-dihydro-1-benzofuran-5-yl)-2-butenoate

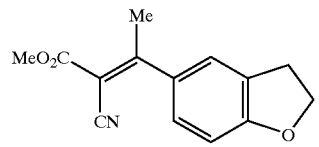

To a stirred solution of 5-acetyl-2,3-dihydrobenzo[b]furan (Aldrich) (1 g, 6.17 mmol) in toluene (60 ml) was added methyl cyanoacetate (0.60 ml, 6.78 mmol), benzylamine (0.07 ml, 0.61 mmol) and acetic acid (0.3 ml, 5.3 mmol) and the whole refluxed in a Dean-Stark apparatus for 16 h. The reaction mixture was cooled, washed with 2N HCl (30 ml), NaHCO$_3$ (30 ml), brine (30 ml), dried (MgSO$_4$) and evaporated to a yellow residue. This residue was purified by column chromatography using 15–20% EtOAc in pentane as eluant to provide the title product (902 mg, 60%); $^1$HNMR (400 MHz, CDCl$_3$) δ: 2.65 (s, 3H), 3.25 (t, 2H), 3.9 (s, 3H), 4.6 (t, 2H), 6.8 (d, 1H), 7.25 (d, 1H), 7.8 (s, 1H); LRMS: M+NH$_4^+$, 261. (ES$^+$).

Preparation 143

Methyl-2-cyano-3-(2,3-dihydro-1-benzofuran-5-yl)-3-methyl-butanoate

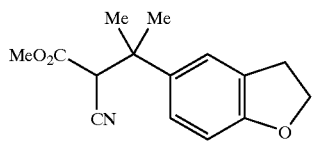

Copper (I) iodide (109 mg, 0.57 mmol) was added to a stirred mixture of MeLi (1.4M in ether, 0.76 ml, 1.07 mmol) in ether (2 ml) at −25° C. under nitrogen. After stirring for 10 min, a solution of the product from Preparation 142 (100 mg, 0.41 mmol) in ether (2 ml) was added dropwise and the whole then stirred at −25° C. for 2 h, and the for a further 2 h while warming to 0° C. Brine (10 ml) was added, and the organics were extracted with EtOAc (10 ml), dried (MgSO$_4$), filtered and evaporated. The residue was then purified by column chromatography using 20% EtOAc in pentane to provide the title product (92 mg, 86%); $^1$HNMR (400 MHz, CDCl$_3$) δ: 1.55 (d, 6H), 3.2 (m, 2H), 3.59 (s, 3H), 3.62 (s, 1H), 4.5 (t, 2H), 6.7 (d, 1H), 7.1 (d, 1H), 7.2 (s, 1H); LRMS: M+NH$_4^+$, 277. (ES$^+$).

Preparation 144

3-(2,3-Dihydro-1-benzofuran-5-yl)-3-methylbutanenitrile

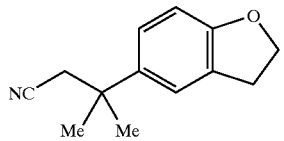

To a stirred solution of the product from Preparation 143 (400 mg, 1.54 mmol) in ethanol (1.5 ml) and dioxan (1.5 ml) was added solid KOH (87 mg, 1.54 mmol) and the whole stirred at reflux for 6 h. The reaction mixture was concentrated in vacuo and dissolved in water (15 ml). The aqueous layer was washed with toluene (15 ml) and then acidified to pH1 with 2N HCl from which the product was extracted with EtOAc (2×20 ml). The organic layers were combined, washed with brine (20 ml), dried (MgSO$_4$), filtered and concentrated in vacuo to afford an orange oil, which was used with no further purification; $^1$HNMR (400 MHz, CDCl$_3$) δ: 1.6 (d, 6H), 3.15 (t, 2H), 3.7 (s, 1H), 4.5 (t, 2H), 6.7 (d, 1H), 7.1 (d, 1H), 7.22 (s, 1H); LRMS: M+NH$_4^+$, 263. (ES$^+$). This oil was taken up in DMA (2 ml) and heated at 150° C. for 2 h and then allowed to cool to room temperature and stirred overnight. The reaction mixture was concentrated in vacuo and then dissolved in EtOAc (10 ml). The organics were washed with brine (10 ml), dried over MgSO$_4$, filtered and concentrated in vacuo to afford an orange oil. This was purified by column chromatography using 15% EtOAc in pentane as eluant to give the title product (100 mg, 32%); $^1$HNMR (400 MHz, CDCl$_3$) δ: 1.45 (s, 6H), 2.55 (s, 2H), 3.2 (t, 2H), 4.5 (t, 2H), 6.7 (d, 1H), 7.1 (d, 1H), 7.2 (s, 1H); LRMS: M+NH$_4^+$, 219. (ES$^+$).

Preparation 145 tert-Butyl-3-(2,3-dihydro-1-benzofuran-5-yl)-3-methylbutylcarbamate

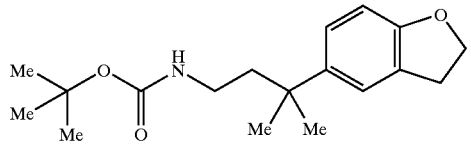

The product from Preparation 144 (250 mg, 1.24 mmol) was taken up in methanol (12 ml) at 0° C. under nitrogen and stirred with di-tert-butyl dicarbonate (542 mg, 2.48 mmol), NiCl$_2$ (161 mg, 1.24 mmol) and then NaBH$_4$ (329 mg, 8.69 mmol) were added portionwise. The black solution was allowed to warm to room temperature overnight and then was concentrated in vacuo. The residue was partitioned between EtOAc (20 ml) and NaHCO$_3$ solution (20 ml), the mixture filtered to remove all solids, and the filtrate extracted with EtOAc (2×20 ml). The combined organics were dried over MgSO$_4$, filtered and evaporated to give the title product (366 mg, 96%) which was used with no further purification; $^1$HNMR (400 MHz, CDCl$_3$) δ: 1.25 (s, 6H), 1.35 (s, 9H), 1.7 (t, 2H), 2.9 (brs., 2H), 3.1 (t, 2H), 4.2 (brs., 1H), 4.5 (t, 2H), 6.65 (d, 1H), 7.0 (d, 1H), 7.1 (s, 1H); LRMS: M−BOC, 206. (ES$^+$).

Preparation 146

3-(2,3-Dihydro-1-benzofuran-5-yl)-3-methylbutylamine

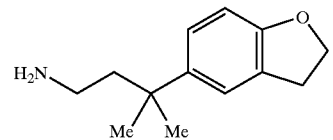

The product from Preparation 145 (366 mg, 1.20 mmol) was taken up in DCM (15 ml) at 0° C. and stirred as hydrogen chloride gas was bubbled through the solution for 15 min. The flow of HCl was stopped, and the reaction mixture was allowed to warm to room temperature and stirred for 2 h. The solution was flooded with ether (20 ml), which caused a white precipitate to form. This solid was filtered off, washed with ether and dried under vacuum to give the title product (177 mg, 61%); $^1$HNMR (400 MHz, MeOD) δ: 1.3 (s, 6H), 1.9 (m, 2H), 2.6 (m, 2H), 3.1 (m, 2H), 4.5 (m, 2H), 6.6 (s, 1H), 7.01 (s, 1H), 7.2 (s, 1H); LRMS: M+H, 207. (ES$^+$).

Preparation 147

Methyl-2-(4-chlorophenyl)-3-cyanopropanoate

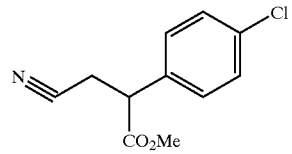

To a stirred solution of diisopropylamine (8.65 ml, 61.8 mmol) in dry THF (100 ml) at −20° C. under nitrogen was added a 2.5M solution of "BuLi in hexanes (23.7 ml, 59.2 mmol) dropwise. The solution was allowed to warm to 0° C. over 20 min, and then cooled to −70° C. A solution of methyl-2-(4-chlorophenyl)acetate (9.5 g, 51.5 mmol) in THF (5 ml) was added dropwise over 5 min, and the whole then stirred for 30 min. Iodoacetonitrile (5.03 ml, 69.5 mmol) was then added slowly, and the combined solution allowed to warm to room temperature over 72 h. Saturated aq. NaHCO$_3$ solution (20 ml) was added, the mixture was concentrated to about 50 ml under vacuum, and then treated with 1N HCl (100 ml). The mixture was extracted with EtOAc (120 ml) which was dried (MgSO$_4$) and evaporated to give a dark brown oil, which was purified by column chromatography using 2:1 DCM:pentane as eluant to give the title product (8.6 g, 75%); $^1$HNMR (400 MHz, CDCl$_3$) δ: 2.80 (dd, 1H), 3.00 (d, 1H), 3.73 (s, 3H), 3.92 (dd, 1H), 7.22 (d, 2H), 7.37 (d, 2H).

Preparation 148

4-Amino-2-(4-chlorophenyl)butanol

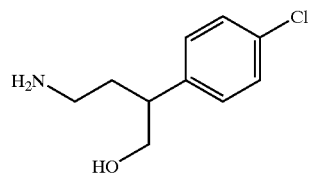

The product from Preparation 147 (235 mg, 1.05 mmol) was taken up in 1 ml THF and added dropwise to a stirred solution of LiAlH$_4$ (2.1 ml, 1M solution in THF, 2.1 mmol) in THF at 0° C. under nitrogen. The mixture was then stirred at room temperature for 2 h, and cooled to 0° C. Water (0.08 ml) was added, followed by 3N aqueous solution of NaOH (0.08 ml) and the whole then diluted with THF (2 ml) and water (0.24 ml). The suspension was stirred for 5 min, and then filtered and the filtrate evaporated to a yellow gum. This was taken up in EtOAc (5 ml) and extracted with 0.5N HCl solution (0.3 ml), which was then basified with Na$_2$CO$_3$ solution to pH10 and extracted with EtOAc (5×3 ml). The combined organics were dried (MgSO$_4$) and evaporated to give the title product (60 mg, 29%); $^1$HNMR (400 MHz, CDCl$_3$) δ: 1.62–1.95 (m, 2H), 2.58–3.00 (m, 3H), 3.58–3.80 (m, 2H), 7.02–7.39 (m, 4H).

Preparation 149 tert-Butyl-(4-chlorophenyl)acetate

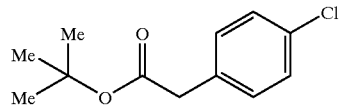

To a suspension of N,N-dimethyl-formamide-di-tert-butyl acetal (25 ml, 104.4 mmol) in dry toluene (90 ml) was added p-chlorophenyl acetic acid (5.94 g, 34.8 mmol) and the whole heated at 80° C. for 1 h. The mixture was diluted with EtOAc (50 ml) and washed with water (50 ml), 3% aqueous NaHCO$_3$ solution (50 ml) and brine (20 ml) and then dried over MgSO$_4$ and evaporated to give an oil. This oil was purified using 35%, then 50% DCM in pentane to give the title product (2.4 g, 30%); $^1$HNMR (400 MHz, CDCl$_3$) δ: 1.42 (s, 9H), 3.44 (s, 2H), 7.20 (d, 2H), 7.28 (d, 2H).

Preparation 150 tert-Butyl-2-(4-chlorophenyl)propanoate

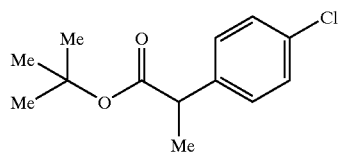

The product from Preparation 149 was alkylated according to an identical procedure to that described in Preparation 147, using methyl iodide as the alkylating agent. The title product was obtained in 95% yield after purification by column chromatography using 25% DCM in pentane as eluant; $^1$HNMR (400 MHz, CDCl$_3$) δ: 1.39 (s, 9H), 1.41 (d, 3H), 3.59 (q, 1H), 7.20 (d, 2H), 7.25 (d, 2H).

Preparation 151

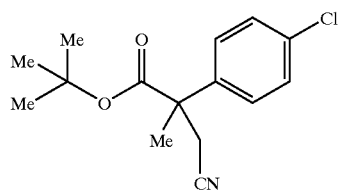

The product from Preparation 150 was alkylated according to an identical procedure to that described in Preparation 137. The title product was obtained in 82% yield after purification by column chromatography, using 35%, then 70% DCM in pentane as eluant; $^1$HNMR (400 MHz, CDCl$_3$) δ: 1.40 (s, 9H), 1.74 (s, 3H), 2.80 (d, 1H), 2.95 (d, 1H), 7.24 (d, 2H), 7.35 (d, 2H).

Preparation 152

4-Amino-2-(4-chlorophenyl)-2-methylbutanol

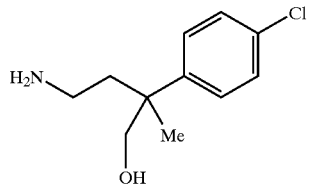

The product from Preparation 151 was reduced with LiAlH$_4$ according to the procedure of Preparation 148 to provide the title product (35%). The product of this reduction was sufficiently pure that it warranted no further purification; $^1$HNMR (400 MHz, CDCl$_3$) δ: 1.22 (s, 3H), 1.71 (ddd, 1H), 2.01 (ddd, 1H), 2.60 (ddd, 1H), 2.83 (ddd, 1H), 3.60 (d, 1H), 3.82 (d, 1H), 7.27 (d, 2H), 7.38 (d, 2H).

Biological Assays

IC50 values of the compounds of the invention against NEP and ACE were determined using methods described in published patent application EP1097719-A1, paragraphs [0368] to [0376]. The IC50 values presented below were determined using NEP from canine kidney. In addition, the IC50 value of some compounds of the invention were determined using NEP from human kidney; these values were similar to the values determined using canine NEP.

The compounds of the invention are potent inhibitors of NEP and are selective against ACE.

The title compounds of Examples herein showed an IC50 against NEP of less than 400 nM.

The title compounds of Examples 1–25, 27–37, 39–41, 43–48, 50–53 and 55–67 showed an IC50 against NEP of less than or equal to 150 nM and a selectivity over ACE of greater than 300 fold.

In particular, the title compound of Example 3 showed an IC50 against NEP of 22 nM; the title compound of Example 4 showed an IC50 against NEP of 4 nM; the title compound of Example 21 showed an IC50 against NEP of 3 nM; the title compound of Example 33 showed an IC50 against NEP of 47 nM; the title compound of Example 43 showed an IC50 against NEP of 29 nM; and the title compound of Example 51 showed an IC50 against NEP of 9 nM. The title compounds of Examples 3, 4, 21, 33, 43 and 51 were all greater than 300 fold selective against ACE.

Animal Model of Female Sexual Arousal Response

The title compound from Example 22 (herein after referred to as "the selected compound") was administered according to the protocol described in EP1097719-A1, paragraphs [0495] to [0499]. The selected compound was made up in 5% saline. The selected compound and vehicle controls were infused using a Harvard 22 pump, infusing at 500 $\mu$l/min via a 3-way tap into the femoral vein. After the infusion, the catheter was flushed with heparinised saline (Hepsaline) so that none of the selected compound was left in the catheter.

The selected compound, tested at clinically relevant doses, significantly enhanced pelvic nerve stimulated increases in genital blood flow (See FIG. 1). The selected compound enhanced the peak increase in vaginal blood flow by up to 56% (n=3) and clitoral blood flow by 50% (n=3) compared to time matched control increases.

FIG. 1 shows the effect of administering the selected compound on the genital blood flow in a rabbit. The selected compound enhanced pelvic nerve stimulated (PNS) increases in genital blood flow in the anaesthetised rabbit model of sexual arousal. Repetitive PNS at 15 minute intervals induced reproducible increases in genital blood flow (Hatched Bars). Administration of the elected compound (Grey bar) enhanced the peak increase in clitoral and vaginal blood flow induced by submaximal stimulation frequencies (eg 4 Hz) compared to increases observed during time matched control stimulations or vehicle controls (Hatched bar). The following simultaneous enhancements were observed following an approximate 0.5 mg/kg iv bolus—a 50% increase in clitoral and a 56% increase in vaginal blood flow (n=3). Data expressed as mean±sem; all changes were monitored using laser Doppler technologies.

There were no major effects of NEP inhibition or on basal/un-stimulated genital blood flow.

Female New Zealand rabbits (~2.5 kg) were pre-medicated with a combination of Medetomidine (Domitor®) 0.5 ml/kg i.m., and Ketamine (Vetalar®) 0.25 ml/kg i.m. whilst maintaining oxygen intake via a face mask. The rabbits were tracheotomised using a Portex™ uncuffed endotracheal tube 3 ID., connected to ventilator and maintained at a ventilation rate of 30–40 breaths per minute, with an approximate tidal volume of 18–20 ml, and a maximum airway pressure of 10 cm $H_2O$. Anaesthesia was then switched to Isoflurane and ventilation continued with $O_2$ at 2 l/min. The right marginal ear vein was cannulated using a 23G or 24G catheter, and Lactated Ringer solution perfused at 0.5 ml/min. The rabbit was maintained at 3% Isoflurane during invasive surgery, dropping to 2% for maintenance anaesthesia.

The left groin area of the rabbit was shaved and a vertical incision was made approximately 5 cm in length along the thigh. The femoral vein and artery were exposed, isolated and then cannulated with a PVC catheter (17G) for the infusion of drugs and compounds. Cannulation was repeated for the femoral artery, inserting the catheter to a depth of 10 cm to ensure that the catheter reached the abdominal aorta. This arterial catheter was linked to a Gould system to record blood pressure. Samples for blood gas analysis were also taken via the arterial catheter. Systolic and diastolic pressures were measured, and the mean arterial pressure calculated using the formula (diastolic ×2+systolic) ÷3. Heart rate was measured via the pulse oxymeter and Po-ne-mah data acquisition software system (Ponemah Physiology Platform, Gould Instrument Systems Inc).

A ventral midline incision was made into the abdominal cavity. The incision was about 5 cm in length just above the pubis. The fat and muscle was bluntly dissected away to reveal the hypogastric nerve which runs down the body cavity. It was essential to keep close to the side curve of the pubis wall in order to avoid damaging the femoral vein and artery which lie above the pubis. The sciatic and pelvic nerves lie deeper and were located after further dissection on the dorsal side of the rabbit. Once the sciatic nerve is identified, the pelvic nerve was easily located. The term pelvic nerve is loosely applied; anatomy books on the subject fail to identify the nerves in sufficient detail. However, stimulation of the nerve causes an increase in vaginal and clitoral blood flow, and innervation of the pelvic region. The pelvic nerve was freed away from surrounding tissue and a Harvard bipolar stimulating electrode was placed around the nerve. The nerve was slightly lifted to give some tension, then the electrode was secured in position. Approximately 1 ml of light paraffin oil was placed around the nerve and electrode. This acts as a protective lubricant to the nerve and prevents blood contamination of the electrode. The electrode was connected to a Grass S88 Stimulator. The pelvic nerve was stimulated using the following parameters:- 0.5–5V, pulse width 0.5 ms, duration of stimulus 10 seconds and a frequency range of 2 to 16 Hz. Reproducible responses were obtained when the nerve was stimulated every 15–20 minutes. A frequency response curve was determined at the start of each experiment in order to determine the optimum frequency to use as a submaximal response, normally 4 Hz. The compound(s) to be tested were infused, via the femoral vein, using a Harvard 22 infusion pump allowing a continuous 15 minute stimulation cycle.

A ventral midline incision was made, at the caudal end of the pubis, to expose the pubic area. Connective tissue was removed to expose the tunica of the clitoris, ensuring that the wall was free from small blood vessels. The external vaginal wall was also exposed by removing any connective tissue. One laser Doppler flow probe was inserted 3 cm into the vagina, so that half the probe shaft was still visible. A second probe was positioned so that it lay just above the external clitoral wall. The position of these probes was then adjusted until a signal was obtained. A second probe was placed just above the surface of a blood vessel on the external vaginal wall. Both probes were clamped in position. Vaginal and clitoral blood flow was recorded either as numbers directly from the Flowmeter using Po-ne-mah data acquisition software (Ponemah Physiology Platform, Gould Instrument Systems Inc), or indirectly from Gould chart recorder trace. Calibration was set at the beginning of the experiment (0–125 ml/min/100 g tissue).

Animal Model of Male Erectile Response

Anaesthetised Rabbit Methodology

The title compound from Example 22 ("the selected compound") alone and in combination with the selective and potent PDE5 inhibitor 3-ethyl-5-[5-(4-ethylpiperazin-1-ylsulfonyl)-2-n-propoxyphenyl]-2-(pyridin-2-yl)methyl-2,6-dihydro-7H-pyrazolo[4,3-d]pyrimidin-7-one were administered in accordance with the following protocol. The selected compound was made up in saline+5% 1M NaOH. The selected compound and vehicle controls were infused using a Harvard 22 pump, infusing at 500 μl/min via a 3-way tap into the femoral vein. After the infusion, the catheter was flushed with heparinised saline (Hepsaline) so that none of the selected compound was left in the catheter. The PDE5 inhibitor was made up in saline+5% 1M HCl, the compounds and vehicle controls were infused at a rate of 0.1 ml/second and left for 15 minutes prior to pelvic nerve stimulation.

Figure 2:
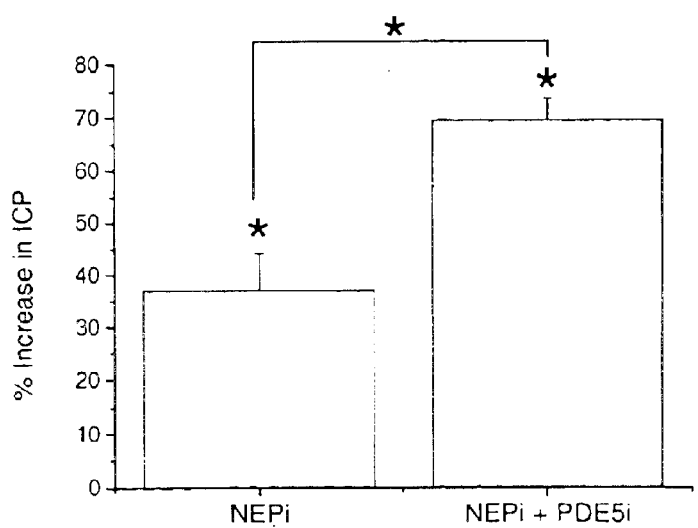
FIG. 2 describes the effect of administering a NEP inhibitor on intracavernosal Pressure ("ICP") and the effect of administering the combination of a NEP inhibitor with a PDE5 inhibitor.

Two experiments were performed: the effect on Intracavernosal pressure (ICP) of administering a) the selected compound alone, and b) in combination with a PDE5 inhibitor. The effect on ICP is shown in FIG. 2. Data is expressed as the mean percentage (%) increase ±s.e.mean. *P<0.01, Students t-test unpaired compared with control increases.

Administration of the selected compound alone resulted in a 37±7% potentiation of submaximally stimulated intracavernosal pressure was observed (see FIG. 2, light grey column; n=4).

Administration of a combination of the selected compound with a selective PDE5 inhibitor (1 mg/kg iv bolus) resulted in a 70±4% potentiation of submaximally stimulated intracavernosal pressure (see FIG. 2, dark grey column; n=3).

There were no major effects of NEP inhibition or concomitant NEP/PDE5 inhibition on basal/un-stimulated intracavernosal pressure.

Male New Zealand rabbits (~2.5 kg) were pre-medicated with a combination of Medetomidine (Domitor®) 0.5 ml/kg i.m., and Ketamine (Vetalar®) 0.25 ml/kg i.m. whilst maintaining oxygen intake via a face mask. The rabbits were tracheotomised using a Portex™ uncuffed endotracheal tube 3 ID., connected to ventilator and maintained at a ventilation rate of 30–40 breaths per minute, with an approximate tidal volume of 18–20 ml, and a maximum airway pressure of 10 cm $H_2O$. Anaesthesia was then switched to Isoflurane and ventilation continued with $O_2$ at 2 l/min. The right marginal ear vein was cannulated using a 23G or 24G catheter, and Lactated Ringer solution perfused at 0.5 ml/min. The rabbit was maintained at 3% Isoflurane during invasive surgery, dropping to 2% for maintenance anaesthesia. The left jugular vein was exposed, isolated and then cannulated with a PVC catheter (17G) for the infusion of the selected compound or combination thereof.

The left groin area of the rabbit was shaved and a vertical incision was made approximately 5 cm in length along the thigh. The femoral vein and artery were exposed, isolated and then cannulated with a PVC catheter (17G) for infusion of the selected compound or combination thereof. Cannulation was repeated for the femoral artery, inserting the catheter to a depth of 10 cm to ensure that the catheter reached the abdominal aorta. This arterial catheter was linked to a Gould system to record blood pressure. Samples for blood gas analysis were also taken via the arterial catheter. Systolic and diastolic pressures were measured, and the mean arterial pressure calculated using the formula (diastolic ×2+systolic) ÷3. Heart rate was measured via the pulse oxymeter and Po-ne-mah data acquisition software system (Ponemah Physiology Platform, Gould Instrument Systems Inc).

A ventral midline incision was made into the abdominal cavity. The incision was about 5 cm in length just above the pubis. The fat and muscle was bluntly dissected away to reveal the hypogastric nerve which runs down the body cavity. It was essential to keep close to the side curve of the pubis wall in order to avoid damaging the femoral vein and artery which lie above the pubis. The sciatic and pelvic nerves lie deeper and were located after further dissection on the dorsal side of the rabbit. Once the sciatic nerve is identified, the pelvic nerve was easily located. The term pelvic nerve is loosely applied; anatomy books on the subject fail to identify the nerves in sufficient detail. However, stimulation of the nerve causes an increase in intracavernosal pressure and cavernosal blood flow, and innervation of the pelvic region. The pelvic nerve was freed away from surrounding tissue and a Harvard bipolar stimulating electrode was placed around the nerve. The nerve was slightly lifted to give some tension, then the electrode was secured in position. Approximately 1 ml of light paraffin oil was placed around the nerve and electrode. This acts as a protective lubricant to the nerve and prevents blood contamination of the electrode. The electrode was connected to a Grass S88 Stimulator. The pelvic nerve was stimulated using the following parameters:-0.5–5V, pulse width 0.5 ms, duration of stimulus 20 seconds with a frequency of 2–16 Hz. Reproducible responses were obtained when the nerve was stimulated every 15–20 minutes. Several stimulations using the above parameters were performed to establish a mean control response. The selected compound or combination thereof was infused, via the jugular vein, using a Harvard 22 infusion pump allowing a continuous 15 minute stimulation cycle. The skin and connective tissue around the penis was removed to expose the penis. A catheter set (Insyte-W, Becton-Dickinson 20 Gauge 1.1×48 mm) was inserted through the tunica albica into the left corpus cavernosal space and the needle removed, leaving a flexible catheter. This catheter was linked via a pressure transducer (Ohmeda 5299-04) to a Gould system to record intracavernosal pressure. Once an intracavernosal pressure was established, the catheter was sealed in place using Vetbond (tissue adhesive, 3M). Heart rate was measured via the pulse oxymeter and Po-ne-mah data acquisition software system (Ponemah Physiology Platform, Gould Instrument Systems Inc).

Intracavernosal blood flow was recorded either as numbers directly from the Flowmeter using Po-ne-mah data acquisition software (Ponemah Physiology Platform, Gould Instrument Systems Inc), or indirectly from Gould chart recorder trace. Calibration was set at the beginning of the experiment (0–125 ml/min/100 g tissue).

What is claimed is:

1. A process for the preparation of a compound of general formula I

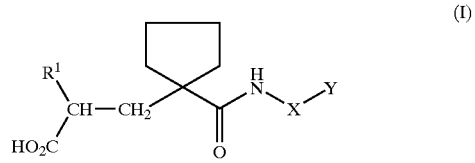

(I)

wherein $R^1$, X and Y are as defined below comprising the steps of:

a) reacting a compound of formula II

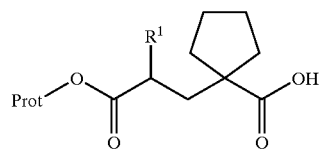
(II)

wherein Prot is a suitable protecting group, with a compound of formula III

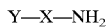
Y—X—NH$_2$ (III)

to give a compound of formula IV;

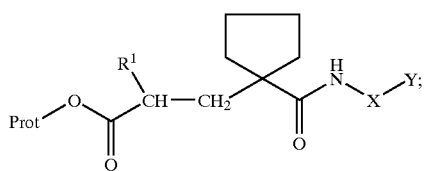
(IV)

then b) reacting compound of formula IV under suitable deprotecting conditions to give the compound of formula I

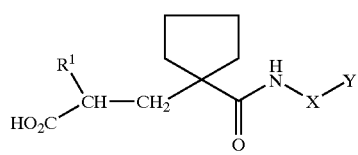
(I)

wherein

R$^1$ is C$_{1-6}$alkyl which may be substituted by one or more substituents, which may be the same or different, selected from the list: halo, hydroxy, C$_{1-6}$alkoxy, hydroxyC$_{1-6}$alkoxy, C$_{1-6}$alkoxyC$_{1-6}$alkoxy, carbocyclyl, carbocyclyloxy, C$_{1-4}$alkoxycarbocyclyloxy, heterocyclyl, heterocyclyloxy, —NR$^2$R$^3$, —NR$^4$COR$^5$, —NR$^4$SO$_2$R$^5$, —CONR$^2$R$^3$, —S(O)$_p$R$^6$, —COR$^7$ and —CO$_2$(C$_{1-4}$alkyl); or R$^1$ is carbocyclyl or heterocyclyl, each of which may be substituted by one or more substituents from said list, which substituents may be the same or different, which list further includes C$_{1-6}$alkyl; or R$^1$ is hydrogen, C$_{1-6}$alkoxy, —NR$^2$R$^3$ or —NR$^4$SO$_2$R$^5$;

wherein

R$^2$ and R$^3$, which may be the same or different, are carbocyclyl or heterocyclyl (each of which may be substituted by C$_{1-4}$alkyl, hydroxy or C$_{1-4}$alkoxy); or are hydrogen or C$_{1-4}$alkyl; or R$^2$ and R$^3$ together with the nitrogen to which they are attached form a pyrrolidinyl, piperidino, morpholino, piperazinyl or N—(C$_{1-4}$alkyl)piperazinyl group;

R$^4$ is hydrogen or C$_{1-4}$alkyl;

R$^5$ is C$_{1-4}$alkyl, CF$_3$, carbocyclyl, C$_{1-4}$alkylcarbocyclyl, C$_{1-4}$alkoxycarbocyclyl, heterocyclyl, C$_{1-4}$alkoxy or —NR$^2$R$^3$;

R$^6$ is C$_{1-4}$alkyl, carbocyclyl, heterocyclyl or NR$^2$R$^3$; and

R$^7$ is C$_{1-4}$alkyl, carbocyclyl or heterocyclyl;

p is 0, 1, 2 or 3;

X is the linkage —(CH$_2$)$_n$— or —(CH$_2$)$_q$—O— (wherein Y is attached to the oxygen); wherein one or more hydrogen atoms in linkage X may be replaced independently by C$_{1-4}$alkoxy; hydroxy; hydroxyC$_{1-3}$alkyl; C$_{3-7}$cycloalkyl; carbocyclyl; heterocyclyl; or by C$_{1-4}$alkyl optionally substituted by one or more fluoro or phenyl groups; n is 3, 4, 5, 6 or 7; and q is 2, 3, 4, 5 or 6; and Y is phenyl or pyridyl, each of which may be substituted by one or more groups R$^8$ which may be the same or different, wherein R$^8$ is hydroxy; mercapto; halogen; cyano; acyl; amino; mono(C$_{1-4}$alkyl)amino; di(C$_{1-4}$alkyl)amino; carbocyclyl or heterocyclyl (either of which is optionally substituted by C$_{1-6}$alkyl, haloC$_{1-6}$alkyl, C$_{1-6}$alkoxy, haloC$_{1-6}$alkoxy, C$_{1-6}$alkylthio or halogen); C$_{1-6}$alkoxy; phenoxy; C$_{1-6}$alkylthio; phenylthio; or alkyl optionally substituted by C$_{1-6}$alkoxy, haloC$_{1-6}$alkoxy, C$_{1-6}$alkylthio, halogen or phenyl; or two R$^8$ groups on adjacent carbon atoms together with the interconnecting carbon atoms may form a fused 5- or 6-membered carbocyclic or heterocyclyic ring, optionally substituted by C$_{1-6}$alkyl, haloC$_{1-6}$alkyl, C$_{1-6}$alkoxy, haloC$_{1-6}$alkoxy, C$_{1-6}$alkylthio or halogen; then c) optionally forming a salt.

2. A process according to claim 1 further comprising asymmetric hydrogenation of any one of compounds of formula XI, XII or XIII

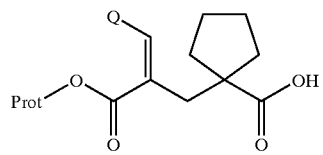
(XI)

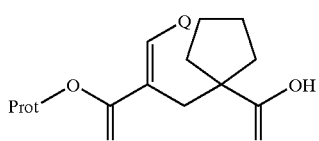
(XII)

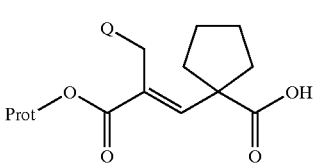
(XIII)

where Q is the substituent on the C$_{1-6}$alkyl group defined for R$^1$ in claim 25, to give a compound of formula IIa

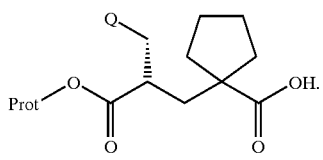
(IIa)

3. A process comprising asymmetric hydrogenation of any one of compounds of formula XI, or XII

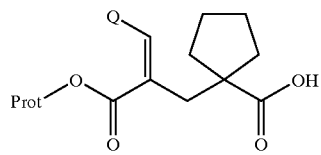
(XI)

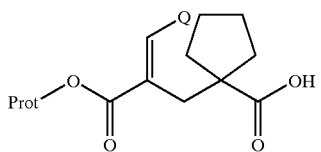
(XII)

where Q is halo, hydroxy, $C_{1-6}$alkoxy, hydroxy$C_{1-6}$alkoxy, $C_{1-6}$alkoxy$C_{1-6}$alkoxy, carbocyclyl, carbocyclyloxy, $C_{1-4}$alkoxycarbocyclyloxy, heterocyclyl, heterocyclyloxy, —NR$^2$R$^3$, —NR$^4$COR$^5$, —NR$^4$SO$_2$R$^5$, —CONR$^2$R$^3$, —S(O)$_p$R$^6$, —COR$^7$ and —CO$_2$(C$_{1-4}$alkyl); wherein
R$^2$ and R$^3$, which may be the same or different, are carbocyclyl or heterocyclyl (each of which may be substituted by C$_{1-4}$alkyl, hydroxy or C$_{1-4}$alkoxy); or are hydrogen or C$_{1-4}$alkyl; or R$^2$ and R$^3$ together with the nitrogen to which they are attached form a pyrrolidinyl, piperidino, morpholino, piperazinyl or N—(C$_{1-4}$alkyl) piperazinyl group;

R$^4$ is hydrogen or C$_{1-4}$alkyl;

R$^5$ is C$_{1-4}$alkyl, CF$_3$, carbocyclyl, C$_{1-4}$alkylcarbocyclyl, C$_{1-4}$alkoxycarbocyclyl, heterocyclyl, C$_{1-4}$alkoxy or —NR$^2$R$^3$;

R$^6$ is C$_{1-4}$alkyl, carbocyclyl, heterocyclyl or NR$^2$R$^3$; and

R$^7$ is C$_{1-4}$alkyl, carbocyclyl or heterocyclyl;

and Prot is a suitable protecting group, to give a compound of formula IIa

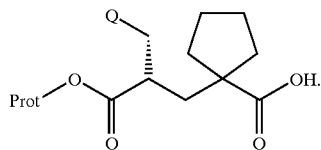
(IIa)

* * * * *